US010845367B2

(12) United States Patent
Mileni et al.

(10) Patent No.: US 10,845,367 B2
(45) Date of Patent: *Nov. 24, 2020

(54) MODIFIED MULTISPANNING MEMBRANE POLYPEPTIDES AND METHODS OF USE THEREOF TO SCREEN THERAPEUTIC AGENTS

(71) Applicant: Abilita Bio, Inc., San Diego, CA (US)

(72) Inventors: Mauro Mileni, San Diego, CA (US); Rosario Billetta, Del Mar, CA (US)

(73) Assignee: Abilita Bio, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/098,821

(22) PCT Filed: May 3, 2017

(86) PCT No.: PCT/US2017/030874
§ 371 (c)(1),
(2) Date: Nov. 2, 2018

(87) PCT Pub. No.: WO2017/192743
PCT Pub. Date: Nov. 9, 2017

(65) Prior Publication Data
US 2019/0137496 A1 May 9, 2019

Related U.S. Application Data

(60) Provisional application No. 62/331,628, filed on May 4, 2016.

(51) Int. Cl.
| | | |
|---|---|---|
| *G01N 33/577* | (2006.01) | |
| *C12N 1/16* | (2006.01) | |
| *C07K 14/705* | (2006.01) | |
| *C12N 15/10* | (2006.01) | |
| *G01N 33/543* | (2006.01) | |
| *G01N 33/68* | (2006.01) | |
| *C12N 15/62* | (2006.01) | |
| *G01N 33/50* | (2006.01) | |
| *C07K 17/00* | (2006.01) | |
| *C07K 17/02* | (2006.01) | |

(52) U.S. Cl.
CPC ......... *G01N 33/577* (2013.01); *C07K 14/705* (2013.01); *C07K 17/00* (2013.01); *C07K 17/02* (2013.01); *C12N 1/16* (2013.01); *C12N 15/1034* (2013.01); *C12N 15/1058* (2013.01); *C12N 15/62* (2013.01); *G01N 33/5041* (2013.01); *G01N 33/5076* (2013.01); *G01N 33/54346* (2013.01); *G01N 33/68* (2013.01)

(58) Field of Classification Search
CPC .......... G01N 33/5041; G01N 33/5076; G01N 33/54346; G01N 33/577; G01N 33/68; C12N 15/1034; C12N 15/1058; C12N 15/62; C12N 1/16; C07K 17/00; C07K 17/02; C07K 14/705
See application file for complete search history.

(56) References Cited

U.S. PATENT DOCUMENTS

| | | | |
|---|---|---|---|
| 3,625,214 A | 12/1971 | Higuchi et al. | |
| 4,469,863 A | 9/1984 | Ts et al. | |
| 4,789,734 A | 12/1988 | Ruoslahti et al. | |
| 4,897,268 A | 1/1990 | Tice et al. | |
| 4,906,474 A | 3/1990 | Langer et al. | |
| 4,925,673 A | 5/1990 | Steiner et al. | |
| 5,034,506 A | 7/1991 | Summerton et al. | |
| 5,075,109 A | 12/1991 | Tice et al. | |
| 5,190,029 A | 3/1993 | Byron et al. | |
| 5,216,141 A | 6/1993 | Benner et al. | |
| 5,235,033 A | 8/1993 | Summerton et al. | |
| 5,376,359 A | 12/1994 | Johnson et al. | |
| 5,386,023 A | 1/1995 | Sanghvi et al. | |
| 5,580,563 A | 12/1996 | Tam et al. | |
| 5,602,240 A | 2/1997 | De Mesmaeker et al. | |
| 5,637,684 A | 6/1997 | Cook et al. | |
| 5,644,048 A | 7/1997 | Yau et al. | |
| 5,776,434 A | 7/1998 | Purewal et al. | |
| 5,811,128 A | 9/1998 | Tice et al. | |
| 5,814,344 A | 9/1998 | Tice et al. | |
| 5,820,883 A | 10/1998 | Tice et al. | |
| 5,853,763 A | 12/1998 | Tice et al. | |

(Continued)

FOREIGN PATENT DOCUMENTS

| | | |
|---|---|---|
| EP | 2450445 A1 | 5/2012 |
| WO | WO-2008068534 A2 | 6/2008 |

(Continued)

OTHER PUBLICATIONS

Klenk C, et al. (Feb. 2016) Scientific Reports. 6:21294 (9 pages). (DOI: 10.1038/srep21294) (nature.com/scientificreports).*
Beaucage et al. The Functionalization of Oligonucleotides Via Phosphoramidite Derivative. Tetrahedron Report No. 329. 49(10):1925-1963 (1993).
Brill et al. Synthesis of Oligodeoxynucleoside Phosphorodithioates via Thioamidites. J. Am. Chem. Soc. 111:2321-2322 (1989).
Brown et al. Pharmacology of GPR55 in Yeast and Identification of GSK494581A as a Mixed-Activity Glycine Transporter Subtype 1 Inhibitor and GPR55 Agonist. J Pharmacol Exp Ther 337:236-246 (2011).
Carlsson et al. Screening for genetic mutations. Nature 380:207 (1996).
Chothia et al. Canonical structures for the hypervariable regions of immunoglobulins. J Mol Biol. 196(4):901-917 (1987).

(Continued)

*Primary Examiner* — Robert S Landsman
(74) *Attorney, Agent, or Firm* — Wilson Sonsini Goodrich & Rosati

(57) ABSTRACT

Disclosed herein are methods, platform, antibodies, vaccines, constructs, and kits for generating a modified multispanning membrane polypeptide. In some instances, also disclosed herein are methods, platform, antibodies, vaccines, constructs, and kits for generating a modified ion channel polypeptide. In some cases, further disclosed herein are methods, platform, antibodies, vaccines, constructs, and kits for generating a modified GPCR.

30 Claims, 13 Drawing Sheets

Specification includes a Sequence Listing.

(56) References Cited

U.S. PATENT DOCUMENTS

| | | | |
|---|---|---|---|
| 5,928,647 | A | 7/1999 | Rock et al. |
| 5,942,252 | A | 8/1999 | Tice et al. |
| 6,379,679 | B1 | 4/2002 | Mabrouk et al. |
| 7,912,654 | B2 | 3/2011 | Kobilka et al. |
| 9,127,287 | B2 | 9/2015 | Hall et al. |
| 2002/0045234 | A1 | 4/2002 | Squirrell et al. |
| 2004/0091975 | A1 | 5/2004 | Midoh et al. |
| 2004/0214317 | A1 | 10/2004 | Battaglino et al. |
| 2004/0265274 | A1 | 12/2004 | Wei et al. |
| 2006/0275288 | A1 | 12/2006 | Grihalde et al. |
| 2010/0099169 | A1 | 4/2010 | Bowie et al. |
| 2010/0304432 | A1 | 12/2010 | O'Keefe et al. |
| 2011/0028700 | A1 | 2/2011 | Heal et al. |
| 2011/0046351 | A1 | 2/2011 | Weir et al. |
| 2012/0270230 | A1 | 10/2012 | Henderson et al. |
| 2012/0302461 | A1 | 11/2012 | Camps et al. |
| 2013/0052646 | A1 | 2/2013 | Tripathi et al. |
| 2014/0256918 | A1 | 9/2014 | Chu et al. |
| 2015/0057166 | A1 | 2/2015 | Kobilka et al. |
| 2016/0123956 | A1 | 5/2016 | Mileni |
| 2019/0263902 | A1 | 8/2019 | Mileni |

FOREIGN PATENT DOCUMENTS

| | | |
|---|---|---|
| WO | WO-2009081136 A2 | 7/2009 |
| WO | WO-2010078290 A2 | 7/2010 |
| WO | WO-2010149964 A2 | 12/2010 |
| WO | WO-2011033322 A2 | 3/2011 |
| WO | WO-2012022928 A2 | 2/2012 |
| WO | WO-2012098413 A1 | 7/2012 |
| WO | WO-2012120315 A2 | 9/2012 |
| WO | WO-2012137012 A1 | 10/2012 |
| WO | WO-2013021206 A2 | 2/2013 |
| WO | WO-2014026136 A2 | 2/2014 |
| WO | WO-2016070022 A1 | 5/2016 |
| WO | WO-2017192743 A1 | 11/2017 |

OTHER PUBLICATIONS

De Mesmaeker et al. Comparison of Rigid and Flexible Backbones in Antisense Oligonucleotides Bioorg Med Chem Lett 4(3):395-398 (1994).

Dempcy et al. Synthesis of a thymidyl pentamer of deoxyribonucleic guanidine and binding studies with DNA homopolynucleotides. PNAS USA 92:6097-6101 (1995).

Egholm et al. Peptide Nucleic Acids (PNA) Oligonucleotide Analogues with an Achiral Peptide Backbone. J Am Chem Soc 114:1895-1897 (1992).

Egholm et al. PNA hybridizes to complementary oligonucleotides obeying the Watson-Crick hydrogen-bonding rules. Letter to Nature 365:566-568 (1993).

Feldhaus et al. Flow-cytometric isolation of human antibodies form a nonimmune *Saccharomyces cerevisiae* surface display library. Nat Biotech 21(2):163-170 (2003).

Gao et al. Unusual conformation of a 3'-thioformacetal linkage in a DNA duplex. Journal of Biomolecular NMR 4:17-34 (1994).

Gregoriadis. Chapter 14: Liposomes. Drug Carriers in Biology and Medicine (57 pgs) (Academic Press, 1979).

Hibbert et al. Directed evolution strategies for improved enzymatic performance. Microb Cell Fact 4:29 (6 pgs.) (2005).

Horn et al. Oligonucleotides with Alternating Anionic and Cationic Phosphoramidate Linkages: Synthesis and Hybridization of Sterouniform Isomers. Tetrahedron Letters 37(6):743-746 (1996).

Hu et al. The immunostimulating complex (ISCOM) is an efficient mucosal delivery system for respiratory syncytial virus (RSV) envelope antigens inducing high local and systemic antibody responses. Clin Exp Immunol 113(2):235-43 (1998).

Hutchings et al. Monoclonal anti-β1-adrenergic receptor antibodies activate G protein signaling in the absence of β-arrestin recruitment. mAbs 6(1):246-261 (2014).

Jain. Strategies and technologies for drug delivery systems. Trends in Pharmacological Sciences 19:155-157 (1998).

Jiang et al. Lengthening and shortening of Plasma DNA in hepatocellular carcinoma patients. PNAS 112(11):E1317:1325 (Jan. 6, 2015).

Jenkins et al. The Biosynthesis of Carbocyclic Nucleosides. Chemical society reviews 24:169-176 (1995).

Jones et al. Long-term storage of DNA-free RNA for use in vaccine studies. BioTechniques 43(5):675-681 (2007).

Jung et al. Hybridization of Alternating Cationic/Anionic Oligonucleotides to RNA Segments. Nucleosides & Nucleotides 13(6-7):1597-1605 (1994).

Kabat et al. Sequences of proteins of immunological interest. NIH Publ. No. 91-3242 1:647-669 (1991).

Koshkin et al. LNA (Locked Nucleic Acid): An RNA Mimic Forming Exceedingly Stable LNA:LNA Duplexes. J Am Chem Soc 120:13252-13253 (1998).

Letsinger et al. Cationic Oligonucleotides. J Am Chem Soc 110:4470-4471 (1988).

Letsinger et al. Effects of pendant groups at phosphorus on binding properties of d-ApA analogues. Nucleic Acids Research 14(8):3487-3499 (1986).

Letsinger et al. Phosphoramidate Analogs of Oligonucleotides. J Org Chem 35(11):3800-3803 (1970).

Mag et al. Synthesis and selective cleavage of an oligodeoxynucleotide containing a bridged internucleotide 5'-phosphorothioate linkage. Nucleic Acids Research 19(7):1437-1441 (1991).

Meier et al. Peptide Nucleic Acids (PNAs)-Unusual Properties of Nonionic Oligonucleotide Analogues. Chem Int Ed Engl 31(8):1008-1010 (1992).

Myers et al. A Yeast Genetic Screen Reveals a Critical Role for the Pore Helix Domain in TRP Channel Gating. Neuron 58:362-373 (2008).

Pauwels et al. Biological activity of new 2-5A analogues. Chemica scripta 26:141-145 (1986).

PCT/US2015/58280 International Preliminary Report on Patentability dated May 11, 2017.

PCT/US2015/58280 International Search Report and Written Opinion dated Mar. 30, 2016.

PCT/US2015/58280 Invitation to pay additional fees and, where applicable, protest fees and partial search report dated Jan. 28, 2016.

PCT/US2017/030874 International Search Report and Written Opinion dated Jul. 27, 2017.

Rawls. Optimistic About Antisense. C&E News Washington (pp. 35-39) (Jun. 2, 1997).

Sarkar et al. Directed evolution of a G protein-coupled receptor for expression, stability, and binding selectivity. PNAS USA 105:14808-14813 (2008).

Sawai. Synthesis and properties of oligoadenylic acids containing 2-5-phosphoramide linkage. The chemical society of Japan pp. 805-808 (1984).

Scarselli et al. Multiple Residues in the Second Extracellular Loop Are Critical for M3 Muscarinic Acetylcholine Receptor Activation. J Bio Chem 282:7385-7396 (2007).

Scherphof et al. Uptake and intracellular processing of targeted and nontargeted liposomes by rat Kupffer cells in viov and in vitro. Annals New York Academy of Sciences 369-385 (1985).

Schofield et al. Application of phage display to high throughput antibody generation and characterization. Genome Biology 8:R254 (2007).

Seitz et al. Enhancing the stability and solubility of the glucocorticoid receptor ligand-binding domain by high-throughput library screening. J Mol Biol 403:562-577 (2010).

Shibata et al. Thermostabilization of the neurotensin receptor NTS1. J Mol Biol 390:262-277 (2009).

Sprinzl et al. Enzymatic Incorporation of ATP and CTP Analogues into the 3' End of tRNA. Eur J Biochem 81:579-589 (1977).

Standfuss et al. Crystal structure of a thermally stable rhodopsin mutant. J Mol Biol 372:1179-1188 (2007).

Tam. Recent advances in multiple antigen peptides. J Immunol Methods 196(1):17-32 (1996).

Tam. Synthetic peptide vaccine design: synthesis and properties of a high-density multiple antigenic peptide system. PNAS USA 85(15):5409-5413 (1988).

(56) References Cited

OTHER PUBLICATIONS

U.S. Appl. No. 14/928,128 Office Action dated May 31, 2018.
U.S. Appl. No. 14/928,128 Office Action dated Nov. 1, 2017.
Vitiello et al. Development of a lipopeptide-based therapeutic vaccine to treat chronic HBV infection. I. Induction of a primary cytotoxic T lymphocyte response in humans. J Clin Invest 95:341-349 (1995).
Von Kiedrowski et al. Parabolic Growth of a Self-Replicating Hexadeoxynucleotide Bearing a 3'-5'-Phosphoamidate Linkage. Angew Chem Int Ed Engl 30(4):423-426 (1991).
Weaver-Feldhaus et al. Yeast mating for combinatorial Fab library generation and surface display. FEBS Letters 564(1-2):24-34 (2004).
Zapata et al. Engineering linear F(ab')2 fragments for efficient production in *Escherichia coli* and enhanced antiproliferative activity. Protein Eng. 8(10):1057-1062 (1995).
Schlegel et al. Bacterial-based membrane protein production. Biochim Biophys Acta 1843(8):1739-1749 (2013).
Schlegel et al. Revolutionizing membrane protein overexpression in bacteria : Revolutionizing membrane protein overexpression in bacteria. Microbial Biotechnology 3(4):403-411 (2009).

* cited by examiner

FIG. 9

>GPR55-WT
MSQQNTSGDCLFDGVNELMKTLQFAVHIPTFVLGLLLNLLAIHGFSTFLKNRWPDYAA
TSIYMINLAVFDLLLVLSLPFKMVLSQVQSPFPSLCTLVECLYFVSMYGSVFTICFISMDR
FLAIRYPLLVSHLRSPRKIFGICCTIWVLVWTGSIPIYSFHGKVEKYMCFHNMSDDTWSA
KVFFPLEVFGFLLPMGIMGFCCSRSIHILLGRRDHTQDWVQQKACIYSIAASLAVFVVSF
LPVHLGFFLQFLVRNSFIVECRAKQSISFFLQLSMCFSNVNCCLDVFCYYFVIKEFRMNIR
AHRPSRVQLVLQDTTISRGAG
(SEQ ID NO: 1)

FIG. 10

>GPR55-EMP-012
MSQQNTSGNCLFDGMNELMKTLQFAVHIPTFVLGLLLNLLAIHGFSTFLKNRWPDYAA
TSIYMINLAVFDLLLVLSLPFKIVLSQVQSPFPSLCTLVECLYFVSMYGSVFTICFISMDRF
LAIRYPLLVSHLRSPRKIFGICCTIWVLVWTGSIPIYSFHGKVEKYMCFHNMSDDTWSAK
VFFPLEVFGFLLPMGIMGFCCSRSIHILLGRRDHTQDWVQQKACIYSIAASLAVFVVSFL
PVHLGFFLQFLVRNSFIVECRAKQSISFFLQLSKCFSNVNCCLDVFCYYFVIKEFRMNIRA
HRPSRVQLVLQDTTISRGAG
(SEQ ID NO: 2)

US 10,845,367 B2

MODIFIED MULTISPANNING MEMBRANE POLYPEPTIDES AND METHODS OF USE THEREOF TO SCREEN THERAPEUTIC AGENTS

CROSS-REFERENCE

This application claims the benefit of U.S. Provisional Application No. 62/331,628, filed May 4, 2016, which application is incorporated herein by reference.

SEQUENCE LISTING

The instant application contains a Sequence Listing which has been submitted electronically in ASCII format and is hereby incorporated by reference in its entirety. Said ASCII copy, created on May 3, 2017, is named 50247-702_601_SL.txt and is 5,882 bytes in size.

BACKGROUND OF THE DISCLOSURE

G-Protein Coupled Receptor (GPCR) is a member of the multispanning membrane proteins and the GPCR superfamily comprises about 800 human GPCR members. The activation of GPCRs by their respective ligands initiates a cascade of multiple signaling processes within the cell, such as for example, regulating cell growth, metabolism, and other essential cellular functions. Dysregulation and aberrant expression of these GPCRs and their subsequent signaling cascades are associated with many different types of disease pathologies.

SUMMARY OF THE DISCLOSURE

In certain embodiments, disclosed herein include methods, platform, antibodies, vaccines, constructs, and kits comprising a modified multispanning membrane polypeptide. In some instances, the modified multispanning membrane polypeptide is an ion channel polypeptide. In some cases, the modified multispanning membrane polypeptide is a GPCR. In some instances, described herein include methods, platform, antibodies, vaccines, constructs, and kits comprising a modified ion channel polypeptide. In additional instances, described herein include methods, platform, antibodies, vaccines, constructs, and kits comprising a modified GPCR.

Disclosed herein, in certain embodiments, is a method of screening a therapeutic agent against a modified multispanning membrane polypeptide, comprising (a) generating a modified multispanning membrane polypeptide library by a random mutagenesis method; (b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; (c) expressing the first set of expression vectors in a first plurality of host cells in the presence or absence of at least one selection agent to select for a set of stably folded multispanning membrane polypeptides; (d) generating a production vector comprising a second polynucleotide encoding a stably folded multispanning membrane polypeptide from the set of stably folded multispanning membrane polypeptide identified in step c); (e) expressing the production vector in a second plurality of host cells, wherein the host cells are production host cells; (0 incubating a multispanning membrane polypeptide product generated from the production vector of step e) with a therapeutic agent; and (g) detecting a binding between the multispanning membrane polypeptide product and the therapeutic agent. In some embodiments, the therapeutic agent is a small molecule or a polypeptide. In some embodiments, the small molecule is a drug or a small molecule fragment. In some embodiments, the polypeptide is an antibody or its binding fragment thereof. In some embodiments, the antibody or its binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, the antibody or its binding fragment thereof is produced through a phage display or yeast display method. In some embodiments, incubating in step f) further comprises immobilizing the multispanning membrane polypeptide product on a nanoparticle prior to incubating with the therapeutic agent. In some embodiments, the nanoparticle comprises a paramagnetic nanoparticle, a superparamagnetic nanoparticle, a metal nanoparticle, or an inorganic nanotube. In some embodiments, the first selection marker gene selects against premature truncations of the multispanning membrane polypeptide and/or facilitates stable and correct folding of the multispanning membrane polypeptide. In some embodiments, the second selection marker gene facilitates stable and correct folding of the multispanning membrane polypeptide. In some embodiments, the modified multispanning membrane polypeptide comprises a plasma membrane protein, a nuclear membrane protein, a peripheral membrane protein, an intracellular-membrane protein, a transporter, a channel protein, an adhesin, a translocase, or a receptor. In some embodiments, the modified multispanning membrane polypeptide is a modified ion channel protein. In some embodiments, the modified ion channel protein is a modified TRPV3, KCa3.1, or TRPC6. In some embodiments, the modified multispanning membrane polypeptide is a modified G protein coupled receptor (GPCR). In some embodiments, the modified GPCR is a modified CCR7, CCR10, GPR55, NTR1, EP2 or EP4 receptor. In some embodiments, the modified GPCR comprises about 1, 2, 3, 4, 5, 6, 7, 8, 9, 10, 15, 20, 25, 30, 35, 40, 45, 50, or more modified amino acid residues. In some embodiments, the modified GPCR comprises about 0.5%, 1%, 2%, 3%, 4%, 5%, 6%, 7%, 8%, 9%, 10%, 11%, 12%, 13%, 14%, 15%, 20%, 25%, 30%, or more modifications. In some embodiments, the modification comprises an insertion, a deletion, or a mutation. In some embodiments, the mutation comprises a nonsense mutation or a missense mutation. In some embodiments, the modification comprises an N-terminal truncation, a C-terminal truncation, or a combination thereof. In some embodiments, the modified GPCR is a mammalian GPCR. In some embodiments, the modified GPCR is a human GPCR. In some embodiments, the first selection marker gene and the second selection marker gene are the same. In some embodiments, the first selection marker gene and the second selection marker gene are different. In some embodiments, the first selection marker gene comprises an antibiotic resistance gene, an auxotrophic gene, or a transcriptional activator or repressor. In some embodiments, the first selection marker gene does not encode a reporter protein. In some embodiments, the first selection marker gene comprises an ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene. In some embodiments, the second selection marker gene comprises an antibiotic resistance gene, an auxotrophic gene, or a transcriptional activator or repressor. In some embodiments, the second selection marker gene does not encode a reporter protein. In some embodiments, the second selection marker gene comprises an ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene. In some embodiments, the first selection marker gene encodes a first selection polypeptide. In some embodiments, the second selection marker gene encodes a second selection polypeptide. In some embodiments, the at least one selection agent is rendered non-toxic to the first plurality of host cells by interaction with the first selection polypeptide and optionally with the second selection polypeptide when the first selection polypeptide is properly displayed on the C-terminal portion of the modified multispanning membrane polypeptide and optionally the second selection polypeptide is properly displayed on the N-terminal portion of the modified multispanning membrane polypeptide. In some embodiments, the at least one selection agent comprises a first selection agent and a second selection agent. In some embodiments, the first selection agent comprises an antibiotic or a toxic metabolite. In some embodiments, the second selection agent comprises an antibiotic or a toxic metabolite. In some embodiments, the antibiotic comprises ampicillin, carbenicillin, gentamicin, chloramphenicol, neomycin, kanamycin, erythromycin, streptomycin, or tetracycline. In some embodiments, the toxic metabolite comprises 5-fluoroorotic acid or 3-amino-1,2,4-triazole. In some embodiments, the first selection agent comprises elevated temperature, reduced temperature, a lack of nutrient, or a lack of co-factor. In some embodiments, the second selection agent comprises elevated temperature, reduced temperature, a lack of nutrient, or a lack of co-factor. In some embodiments, the production vector of step d) does not comprise the first selection marker gene or the second selection marker gene. In some embodiments, the first set of expression vectors and the production vector further independently comprise a polynucleotide encoding a tag. In some embodiments, the tag is linked to the N-terminus of the modified multispanning membrane polypeptide, the C-terminus of the modified multispanning membrane polypeptide, or a combination thereof. In some embodiments, the tag comprises MBP, TrxA, FLAG-tag, AVI-tag, or HisTag. In some embodiments, the method further comprises: (a) generating a second set of production vectors in which each production vector comprises a third polynucleotide encoding a stably folded multispanning membrane polypeptide from the set of stably folded multispanning membrane polypeptides identified in step c) of the method discussed above; (b) expressing the second set of production vectors in a third plurality of host cells, wherein the host cells are production host cells; and (c) analyzing a set of multispanning membrane polypeptide products of step b) by an analytical method to determine a multispanning membrane polypeptide product from the set with an enhanced or improved physicochemical property for screening against the therapeutic agent of step f) of the method discussed above, wherein the enhanced or improved physicochemical property is relative to a control multispanning membrane polypeptide. In some embodiments, the enhanced or improved physicochemical property comprises expression level, stability, conformational selectivity, homogeneity, protein crystallization, antigenicity, immunogenicity, or pathway activation selectivity. In some embodiments, the control comprises a wild-type multispanning membrane polypeptide or a modified multispanning membrane polypeptide with a different modification. In some embodiments, the binding in step g) is detected by a flow cytometry method or by enzyme-linked immunosorbent assay (ELISA). In some embodiments, the flow cytometry method comprises magnetic-activated cell sorting (MACS) or fluorescence-activated cell sorting (FACS). In some embodiments, the host cell is a prokaryotic host cell, a mammalian host cell, or an insect host cell. In some embodiments, the first plurality of host cells comprises prokaryotic host cells. In some embodiments, the prokaryotic host cells are E. coli cells. In some embodiments, the second plurality of host cells comprises mammalian host cells or insect host cells.

Disclosed herein, in certain embodiments, is a method of screening an antibody or its binding fragment thereof against a modified multispanning membrane polypeptide, comprising: (a) generating a modified multispanning membrane polypeptide library by a random mutagenesis method; (b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; (c) expressing the first set of expression vectors in a first plurality of host cells in the presence or absence of at least one selection agent to select for a set of stably folded multispanning membrane polypeptides; (d) generating a production vector comprising a second polynucleotide encoding a stably folded multispanning membrane polypeptide from the set of stably folded multispanning membrane polypeptide identified in step c); (e) expressing the production vector in a second plurality of host cells, wherein the host cells are production host cells; (f) incubating a multispanning membrane polypeptide product generated from the production vector of step e) with an antibody or its binding fragment thereof; and (g) detecting a binding between the multispanning membrane polypeptide product and the antibody or its binding fragment thereof. In some embodiments, incubating in step f) further comprises immobilizing the multispanning membrane polypeptide product on a nanoparticle prior to incubating with the therapeutic agent. In some embodiments, the nanoparticle comprises a paramagnetic nanoparticle, a superparamagnetic nanoparticle, a metal nanoparticle, or an inorganic nanotube. In some embodiments, the first selection marker gene selects against premature truncations of the multispanning membrane polypeptide and/or facilitates stable and correct folding of the multispanning membrane polypeptide. In some embodiments, the second selection marker gene facilitates stable and correct folding of the multispanning membrane polypeptide. In some embodiments, the modified multispanning membrane polypeptide comprises a plasma membrane protein, a nuclear membrane protein, a peripheral membrane protein, an intracellular-membrane protein, a transporter, a channel protein, an adhesin, a translocase, or a receptor. In some embodiments, the antibody or its binding fragment thereof is produced through a phage display or a yeast display method. In some embodiments, the antibody or its binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, the modified multispanning membrane polypeptide is a modified ion channel protein. In some embodiments, the modified ion channel protein is a modified TRPV3, KCa3.1, or TRPC6. In some embodiments, the modified multispanning membrane polypeptide is a modified G protein coupled receptor (GPCR). In some embodiments, the modified GPCR is a modified CCR7, CCR10, GPR55, NTR1, EP2, or EP4 receptor. In some embodiments, the modified GPCR comprises about 1, 2, 3, 4, 5, 6, 7, 8, 9, 10, 15, 20, 25, 30, 35, 40, 45, 50, or more modified amino acid residues. In some embodiments, the modified GPCR comprises about 0.5%, 1%, 2%, 3%, 4%, 5%, 6%, 7%, 8%, 9%, 10%, 11%, 12%, 13%, 14%, 15%, 20%, 25%, 30%, or more modifications. In some embodiments, the modification comprises an insertion, a deletion, or a mutation. In some embodiments, the mutation comprises a nonsense mutation or a missense mutation. In some embodiments, the modification comprises an N-terminal truncation, a C-terminal truncation, or a combination thereof. In some embodiments, the modified GPCR is a mammalian GPCR. In some embodiments, the modified GPCR is a human GPCR. In some embodiments, the first selection marker gene and the second selection marker gene are the same. In some embodiments, the first selection marker gene and the second selection marker gene are different. In some embodiments, the first selection marker gene comprises an antibiotic resistance gene, an auxotrophic gene, or a transcriptional activator or repressor. In some embodiments, the first selection marker gene does not encode a reporter protein. In some embodiments, the first selection marker gene comprises an ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene. In some embodiments, the second selection marker gene comprises an antibiotic resistance gene, an auxotrophic gene, or a transcriptional activator or repressor. In some embodiments, the second selection marker gene does not encode a reporter protein. In some embodiments, the second selection marker gene comprises an ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene. In some embodiments, the first selection marker gene encodes a first selection polypeptide. In some embodiments, the second selection marker gene encodes a second selection polypeptide. In some embodiments, the at least one selection agent is rendered non-toxic to the first plurality of host cells by interaction with the first selection polypeptide and optionally with the second selection polypeptide when the first selection polypeptide is properly displayed on the C-terminal portion of the modified multispanning membrane polypeptide and optionally the second selection polypeptide is properly displayed on the N-terminal portion of the modified multispanning membrane polypeptide. In some embodiments, the at least one selection agent comprises a first selection agent and a second selection agent. In some embodiments, the first selection agent comprises an antibiotic or a toxic metabolite. In some embodiments, the second selection agent comprises an antibiotic or a toxic metabolite. In some embodiments, the antibiotic comprises ampicillin, carbenicillin, gentamicin, chloramphenicol, neomycin, kanamycin, erythromycin, streptomycin, or tetracycline. In some embodiments, the toxic metabolite comprises 5-fluoroorotic acid or 3-amino-1,2,4-triazole. In some embodiments, the first selection agent comprises elevated temperature, reduced temperature, a lack of nutrient, or a lack of co-factor. In some embodiments, the second selection agent comprises elevated temperature, reduced temperature, a lack of nutrient, or a lack of co-factor. In some embodiments, the expression vector of step d) does not comprise the first selection marker gene or the second selection marker gene. In some embodiments, the first set of expression vectors and the expression vector further independently comprise a polynucleotide encoding a tag. In some embodiments, the tag is linked to the N-terminus of the modified multispanning membrane polypeptide, the C-terminus of the modified multispanning membrane polypeptide, or a combination thereof. In some embodiments, the tag comprises MBP, TrxA, FLAG-tag, AVI-tag, or HisTag. In some embodiments, the method further comprises: (a) generating a second set of production vectors in which each production vector comprises a third polynucleotide encoding a stably folded multispanning membrane polypeptide from the set of stably folded multispanning membrane polypeptides identified in step c) of the method discussed above; (b) expressing the second set of production vectors in a third plurality of host cells, wherein the host cells are production host cells; and (c) analyzing a set of multispanning membrane polypeptide products of step b) by an analytical method to determine a multispanning membrane polypeptide product from the set with an enhanced or improved physicochemical property for screening against the therapeutic agent of step f) of the method discussed above, wherein the enhanced or improved physicochemical property is relative to a control multispanning membrane polypeptide. In some embodiments, the enhanced or improved physicochemical property comprises expression level, stability, conformational selectivity, homogeneity, protein crystallization, antigenicity, immunogenicity or pathway activation selectivity. In some embodiments, the control comprises a wild-type multispanning membrane polypeptide or a modified multispanning membrane polypeptide with a different modification. In some embodiments, the binding in step g) is detected by a flow cytometry method or by enzyme-linked immunosorbent assay (ELISA). In some embodiments, the flow cytometry method comprises magnetic-activated cell sorting (MACS) or fluorescence-activated cell sorting (FACS). In some embodiments, the host cell is a prokaryotic host cell, a mammalian host cell, or an insect host cell. In some embodiments, the first plurality of host cells comprises prokaryotic host cells. In some embodiments, the prokaryotic host cells are E. coli cells. In some embodiments, the second plurality of host cells comprises mammalian host cells or insect host cells.

Disclosed herein, in certain embodiments, is an isolated and purified antibody or its binding fragment thereof comprising a heavy chain CDR1, CDR2, and CDR3 sequence and a light chain CDR1, CDR2, and CDR3 sequence, wherein the heavy chain and light chain CDRs interact with a modified multispanning membrane polypeptide and wherein the antibody or its binding fragment thereof is produced by the process of: (a) generating a modified multispanning membrane polypeptide library by a random mutagenesis method; (b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; (c) expressing the first set of expression vectors in a first plurality of host cells in the presence or absence of at least one selection agent to select for a set of stably folded multispanning membrane polypeptides; (d) generating a production vector comprising a second polynucleotide encoding a stably folded multispanning membrane polypeptide from the set of stably folded multispanning membrane polypeptides identified in step c); (e) expressing the production vector in a second plurality of host cells, wherein the host cells are production host cells; (f) incubating a multispanning membrane polypeptide product generated from the production vector of step e) with a set of antibodies or their binding fragments thereof; and (g) selecting an antibody or its binding fragment thereof that binds specifically with the multispanning membrane polypeptide product. In some embodiments, the antibody or its binding fragment thereof is produced through a phage display or a yeast display method. In some embodiments, the antibody or its binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some embodiments, the modified multispanning membrane polypeptide is a modified ion channel protein. In some embodiments, the modified ion channel protein is a modified TRPV3, KCa3.1, or TRPC6. In some embodiments, the modified multispanning membrane polypeptide is a modified G protein coupled receptor (GPCR). In some embodiments, the modified GPCR is a modified CCR7, CCR10, GPR55, NTR1, EP2, or EP4 receptor.

Disclosed herein, in certain embodiments, is a vaccine comprising an isolated and purified antibody or its binding fragment thereof described above. In some embodiments, the vaccine further comprises an adjuvant. In some embodiments, the adjuvant comprises granulocyte-macrophage colony-stimulating factor (GM-CSF).

Disclosed herein, in certain embodiments, is a vaccine comprising a modified multispanning membrane polypeptide or a polynucleotide encoding the modified multispanning membrane polypeptide, wherein the modified multispanning membrane polypeptide is produced by the process of: (a) generating a modified multispanning membrane polypeptide library by a random mutagenesis method; (b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; (c) expressing the first set of expression vectors in a first plurality of host cells in the presence or absence of at least one selection agent to select for a set of stably folded multispanning membrane polypeptides; (d) generating a second set of production vectors in which each production vector comprises a third polynucleotide encoding a stably folded multispanning membrane polypeptide from the set of stably folded multispanning membrane polypeptides identified in step c); (e) expressing the second set of production vectors in a second plurality of host cells, wherein the host cells are production host cells; and (f) analyzing a set of multispanning membrane polypeptide products generated from the second set of expression vectors of step e) with an analytical method to determine a stably folded multispanning membrane polypeptide with an enhanced or improved physicochemical property for generation of a vaccine, wherein the enhanced or improved physicochemical property is relative to a control multispanning membrane polypeptide. In some embodiments, the enhanced or improved physicochemical property comprises expression level, stability, conformational selectivity, homogeneity, protein crystallization, antigenicity, immunogenicity, or pathway activation selectivity. In some embodiments, the control comprises a wild-type multispanning membrane polypeptide or a modified multispanning membrane polypeptide with a different modification. In some embodiments, the modified multispanning membrane polypeptide is a modified ion channel protein. In some embodiments, the modified ion channel protein is a modified TRPV3, KCa3.1, or TRPC6. In some embodiments, the modified multispanning membrane polypeptide is a modified G protein coupled receptor (GPCR). In some embodiments, the modified GPCR is a modified CCR7, CCR10, GPR55, NTR1, EP2, or EP4 receptor. In some embodiments, the vaccine further comprises an adjuvant. In some embodiments, the adjuvant comprises granulocyte-macrophage colony-stimulating factor (GM-CSF).

Disclosed herein, in certain embodiments, is a modified multispanning membrane polypeptide of Formula (I):

$$SP2_x\text{-}L2_m\text{-}MSMP_y\text{-}L1_n\text{-}SP1_z \qquad \text{Formula I}$$

wherein:
MSMP is a multispanning membrane polypeptide comprising at least one modification;
SP1 is a first selection polypeptide linked to the C-terminus of MSMP, wherein SP1 is resistant against a first selection agent;
SP2 is a second selection polypeptide linked to the N-terminus of MSMP, wherein SP2 is resistant against a second selection agent;
L1 is a first linker;
L2 is a second linker;
x is independently 0-3;
y is independently 1-5;
z is independently 1-3; and
m and n are each independently 0-60 amino acid residues.

In some embodiments, the modified multispanning membrane polypeptide comprises a plasma membrane protein, a nuclear membrane protein, a peripheral membrane protein, an intracellular-membrane protein, a transporter, a channel protein, an adhesin, a translocase, or a receptor. In some embodiments, the modified multispanning membrane polypeptide is a modified ion channel protein. In some embodiments, the modified ion channel protein is a modified TRPV3, KCa3.1, or TRPC6. In some embodiments, the modified multispanning membrane polypeptide is a modified G protein coupled receptor (GPCR). In some embodiments, the modified GPCR is a modified CCR7, CCR10, GPR55, NTR1, EP2, or EP4 receptor. In some embodiments, the modified GPCR comprises about 1, 2, 3, 4, 5, 6, 7, 8, 9, 10, 15, 20, 25, 30, 35, 40, 45, 50, or more modified amino acid residues. In some embodiments, the modified GPCR comprises about 0.5%, 1%, 2%, 3%, 4%, 5%, 6%, 7%, 8%, 9%, 10%, 11%, 12%, 13%, 14%, 15%, 20%, 25%, 30%, or more modifications. In some embodiments, the at least one modification is generated through a random mutagenesis method. In some embodiments, the at least one modification comprises an insertion, a deletion, or a mutation. In some embodiments, the mutation comprises a nonsense mutation or a missense mutation. In some embodiments, the at least one modification comprises an N-terminal truncation, a C-terminal truncation, or a combination thereof. In some embodiments, the modified GPCR is a mammalian GPCR. In some embodiments, the modified GPCR is a human GPCR. In some embodiments, SP1, when expressed in a host cell, is located in an intracellular portion or an extracellular portion of the host cell. In some embodiments, SP2, when expressed in a host cell, is located in an intracellular portion or an extracellular portion of the host cell. In some embodiments, SP1, when expressed in a host cell, is located in an intracellular portion of the host cell. In some embodiments, SP2, when expressed in a host cell, is located in an extracellular portion of the host cell. In some embodiments, SP1, when expressed in a host cell, is located in an intracellular portion of the host cell and SP2, when expressed in a host cell, is located in an extracellular portion of the host cell. In some embodiments, the first selection polypeptide is encoded by an antibiotic resistance gene, an auxotrophic gene, or a transcriptional activator or repressor. In some embodiments, the first selection polypeptide is not a reporter protein. In some embodiments, the first selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene. In some embodiments, the second selection polypeptide is encoded by an antibiotic resistance gene, an auxotrophic gene, or a transcriptional activator or repressor. In some embodiments, the second selection polypeptide is not a reporter protein. In some embodiments, the second selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene. In some embodiments, $SP1_z$ is $SP1_{2-3}$ and each SP1 is different from the other. In some embodiments, $SP2_x$ is $SP2_{2-3}$ and each SP2 is different from the other. In some embodiments, the first selection agent comprises an antibiotic or a toxic metabolite. In some embodiments, the second selection agent comprises an antibiotic or a toxic metabolite. In some embodiments, the antibiotic comprises ampicillin, carbenicillin, gentamicin, chloramphenicol, neomycin, kanamycin, streptomycin, or tetracycline. In some embodiments, the toxic metabolite comprises 5-fluoroorotic acid or 3-amino-1,2,4-triazole. In some embodiments, the first selection agent comprises elevated temperature, reduced temperature, a lack of nutrient, or a lack of co-factor. In some embodiments, the second selection agent comprises elevated temperature, reduced temperature, a lack of nutrient, or a lack of co-factor. In some embodiments, the modified multispanning membrane polypeptide further comprises a tag. In some embodiments, the tag is linked to the N-terminus of the modified multispanning membrane polypeptide, the C-terminus of the modified multispanning membrane polypeptide, or a combination thereof. In some embodiments, the tag comprises MBP, TrxA, FLAG-tag, AVI-tag, or HisTag.

In some embodiments, the modified multispanning membrane polypeptide further comprises a modified multispanning membrane polypeptide of Formula (Ia):

$$SP2\text{-}L2_m\text{-}MSMP\text{-}L1_n\text{-}SP1 \qquad \text{Formula Ia}$$

wherein:
MSMP is a multispanning membrane polypeptide comprising at least one modification;
SP1 is a first selection polypeptide linked to the C-terminus of MSMP, wherein SP1 is resistant against a first selection agent;
SP2 is a second selection polypeptide linked to the N-terminus of MSMP, wherein SP2 is resistant against a second selection agent;
L1 is a first linker;
L2 is a second linker; and
m and n are each independently 0-60 amino acid residues.

In some embodiments, the modified multispanning membrane polypeptide further comprises a modified receptor polypeptide of Formula (II):

$$SP2_x\text{-}L2_m\text{-}RP_y\text{-}L1_n\text{-}SP1_z \qquad \text{Formula II}$$

wherein:
RP is a receptor polypeptide selected from an ion channel polypeptide or a GPCR, wherein RP comprises at least one modification;
SP1 is a first selection polypeptide linked to the C-terminus of RP, wherein SP1 is resistant against a first selection agent;
SP2 is a second selection polypeptide linked to the N-terminus of RP, wherein SP2 is resistant against a second selection agent;
L1 is a first linker;
L2 is a second linker;
x is independently 0-3;
y is independently 1-5;
z is independently 1-3; and
m and n are each independently 0-60 amino acid residues.

In some embodiments, the ion channel polypeptide is a voltage-gated ion channel polypeptide or a transient receptor potential channel polypeptide. In some embodiments, the ion channel polypeptide comprises TRPV3, KCa3.1, or TRPC6. In some embodiments, GPCR comprises CCR7, CCR10, GPR55, NTR1, EP2, or EP4 receptor.

In some embodiments, the modified multispanning membrane polypeptide further comprises a modified receptor polypeptide of Formula (III):

$$SP2_x\text{-}L2_m\text{-}GPCR_y\text{-}L1_n\text{-}SP1_z \qquad \text{Formula III}$$

wherein:
GPCR is a GPCR comprising at least one modification;
SP1 is a first selection polypeptide linked to the C-terminus of GPCR, wherein SP1, when expressed in a host cell, is located in the intracellular portion of the host cell and is resistant against a first selection agent;
SP2 is a second selection polypeptide linked to the N-terminus of GPCR, wherein SP2, when expressed in a host cell, is located in the extracellular portion of the host cell and is resistant against a second selection agent;
L1 is a first linker;
L2 is a second linker;
x is independently 0-3;

y is independently 1-5;
z is independently 1-3; and
m and n are each independently 0-60 amino acid residues.

In some embodiments, GPCR is a mammalian GPCR. In some embodiments, GPCR is a human GPCR. In some embodiments, GPCR comprises CCR7, CCR10, GPR55, NTR1, EP2, or EP4 receptor.

In some embodiments, the modified multispanning membrane polypeptide further comprises a modified receptor polypeptide of Formula (IV):

wherein:
ICP is an ion channel polypeptide comprising at least one modification;
SP1 is a first selection polypeptide linked to the C-terminus of ICP, wherein SP1 is resistant against a first selection agent;
SP2 is a second selection polypeptide linked to the N-terminus of ICP, wherein SP2 is resistant against a second selection agent;
L1 is a first linker;
L2 is a second linker;
x is independently 0-3;
y is independently 1-5;
z is independently 1-3; and
m and n are each independently 0-60 amino acid residues.

In some embodiments, the ion channel polypeptide comprises TRPV3, KCa3.1, or TRPC6.

Disclosed herein, in certain embodiments, is a vector encoding a modified multispanning membrane polypeptide described above.

Disclosed herein, in certain embodiments, is a cell culture composition comprising a host cell expressing a modified multispanning membrane polypeptide described above; and a cell culture media.

BRIEF DESCRIPTION OF THE DRAWINGS

Various aspects of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9 shows primary amino acid sequence of GPCR-GPR55 WT (SEQ ID NO: 1).

FIG. 10 shows primary amino acid sequence of GPCR-GPR55-EMP-012 (SEQ ID NO: 2). The underlined residues denote mutation positions relative to the wild-type GPR55 sequence.

DETAILED DESCRIPTION OF THE DISCLOSURE

Figure 1:
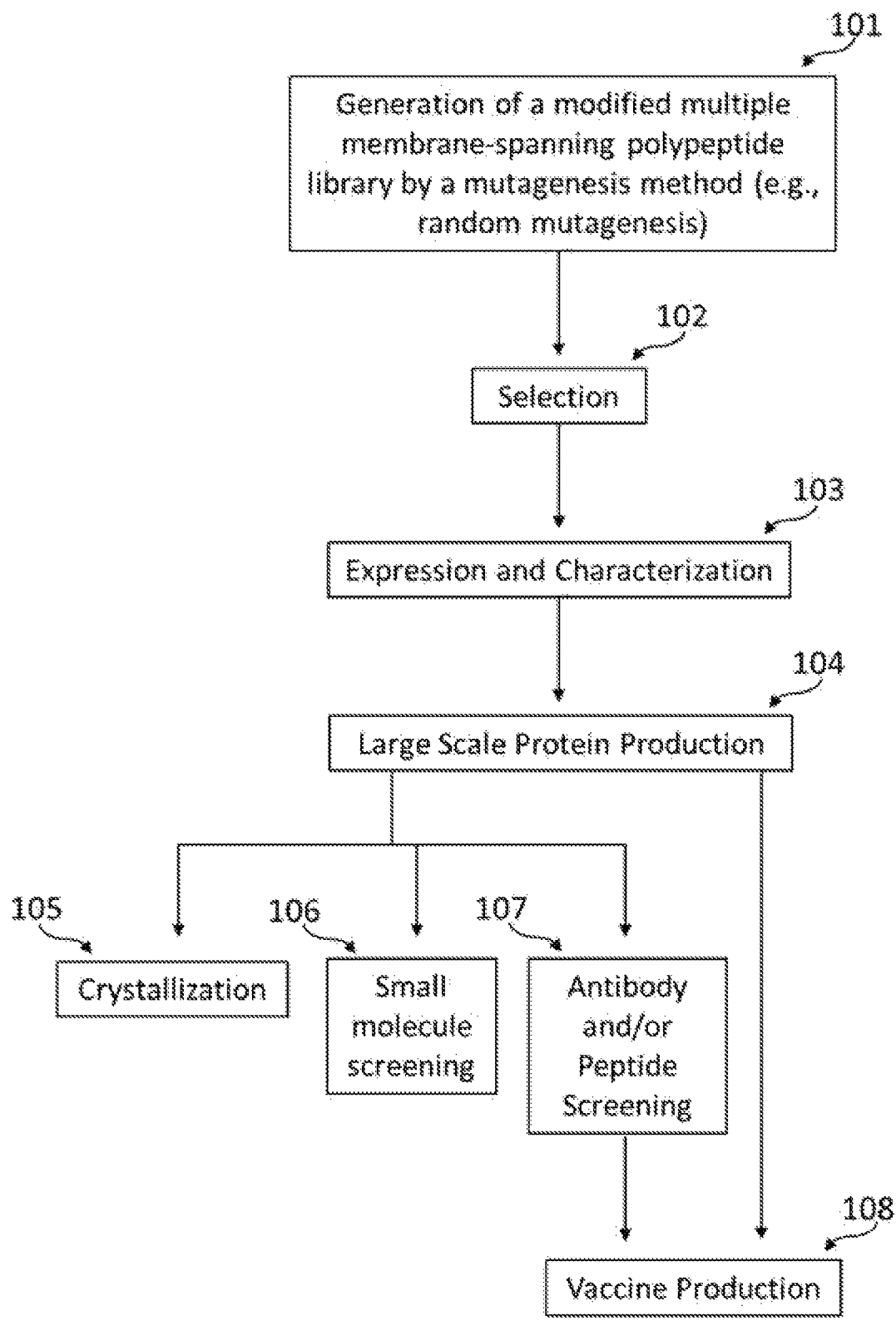
FIG. 1 illustrates a conceptual schematic of a platform described herein for generating a modified multispanning membrane polypeptide with an improved or enhanced physicochemical property.

Multi spanning membrane proteins are essential components of cellular membranes as they provide links between the extracellular and the intracellular environment of a cell. In some instances, multispanning membrane proteins constitute about 30% of the proteome and are important to numerous cellular and physiological processes. In some instances, multispanning membrane proteins have also been linked to many pathological conditions (e.g., endocrine diseases or cancer). Furthermore, for example, about 60% of current drugs in the market interact with or modulate a multispanning membrane protein.

In some instances, experimentation with a multispanning membrane protein presents difficulties as the multispanning membrane protein's lipid-interacting surfaces are highly hydrophobic and requires the use of detergents or amphipathic molecules that mimic the membrane bilayer environment. Further, a multispanning membrane protein comprises high conformational flexibility, low stability, and/or low expression level. Further still, handling of a multispanning membrane protein, for example, during experimentation, often leads to unfolding, inactivation, and/or degradation of the multispanning membrane protein.

In some embodiments, described herein are methods and platform for generating a multispanning membrane protein (or a modified multispanning membrane polypeptide) with improved properties (e.g., physicochemical properties) for handling during experimentation. In some instances, the method and platform comprise generating a modified multispanning membrane polypeptide library by a random mutagenesis method; generating a first set of expression vectors in which each expression vector comprises a first polynucleotide encoding a modified multispanning membrane polypeptide from the library; a first selection marker gene operably linked to the C-terminus of the polynucleotide; and optionally a second selection marker gene operably linked to the N-terminus of the polynucleotide; and expressing the first set of expression vectors in a first plurality of host cells in the presence or absence of at least one selection agent to select for a set of stably folded multispanning membrane polypeptides.

In some embodiments, also described herein include methods of screening a therapeutic agent (e.g., a polypeptide such as an antibody or a small molecule). In some embodiments, a method of screening a therapeutic agent against a modified multispanning membrane polypeptide described herein comprises a) generating a modified multispanning membrane polypeptide library by a random mutagenesis method; b) generating a first set of expression vectors in which each expression vector comprises a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; c) expressing the first set of expression vectors in a first plurality of host cells in the presence or absence of at least one selection agent to select for a set of stably folded multispanning membrane polypeptides; d) generating a production vector comprising a second polynucleotide encoding a stably folded multispanning membrane polypeptide from the set of stably folded multispanning membrane polypeptides identified in step c); e) expressing the production vector in a second plurality of host cells, wherein the host cells are production host cells; f) incubating a multispanning membrane polypeptide product generated from the production vector of step e) with a therapeutic agent; and g) detecting a binding between the multispanning membrane polypeptide product and the therapeutic agent.

In other embodiments, described herein include vaccines (e.g., antibody-based vaccine, nucleic acid based vaccine, or polypeptide-based vaccine), generated from a modified multispanning membrane polypeptide. In some instances, a vaccine is an antibody-based vaccine. In other instance, a vaccine is a polypeptide based vaccine or a nucleic acid based vaccine in which the modified multispanning membrane polypeptide is produced by the process of: a) generating a modified multispanning membrane polypeptide library by a random mutagenesis method; b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; c) expressing the first set of expression vectors in a first plurality of host cells in the presence of at least one selection agent to select for a set of stably folded multispanning membrane polypeptides; d) generating a second set of production vectors in which each production vector comprises a third polynucleotide encoding a stably folded multispanning membrane polypeptide from the set of stably folded multispanning membrane polypeptides identified in step c); e) expressing the second set of production vectors in a second plurality of host cells, wherein the host cells are production host cells; and f) analyzing a set of multispanning membrane polypeptide products generated from the second set of production vectors of step e) with an analytical method to determine a multispanning membrane polypeptide product from the set with an enhanced or improved physicochemical property for generation of a vaccine, wherein the enhanced or improved physicochemical property is relative to a control multispanning membrane polypeptide.

In additional embodiments, described herein include antibody compositions selected against a modified multispanning membrane polypeptide described herein. In some instances, an isolated and purified antibody or its binding fragment thereof described herein comprises a heavy chain CDR1, CDR2, and CDR3 sequence and a light chain CDR1, CDR2, and CDR3 sequence, wherein the heavy chain and light chain CDRs interact with a modified multispanning membrane polypeptide and wherein the antibody or its binding fragment thereof is produced by the process of: a) generating a modified multispanning membrane polypeptide library by a random mutagenesis method; b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; c) expressing the first set of expression vectors in a first plurality of host cells in the presence or absence of at least one selection agent to select for a set of stably folded multispanning membrane polypeptides; d) generating a production vector comprising a second polynucleotide encoding a stably folded multispanning membrane polypeptide from the set of stably folded multispanning membrane polypeptide identified in step c); e) expressing the production vector in a second plurality of host cells, wherein the host cells are production host cells; f) incubating a multispanning membrane polypeptide product generated from the production vector of step e) with a set of antibodies or their binding fragments thereof; and g) selecting an antibody or its binding fragment thereof that binds specifically with the multispanning membrane polypeptide product.

In further embodiments, also described herein include a modified multispanning membrane polypeptide construct (e.g., a modified multispanning membrane polypeptide of Formulas I-IV) and kits comprising a modified multispanning membrane polypeptide construct, a purified modified multispanning membrane polypeptide, an antibody described herein, or a vaccine described herein.

Multispanning Membrane Polypeptides

In some embodiments, disclosed herein is a platform for generating a modified multispanning membrane polypeptide. In some instances, also included herein is a method of generating a modified multispanning membrane polypeptide. In some embodiments, a multispanning membrane polypeptide comprises a full length membrane protein or a fragment thereof. In some instances, multispanning membrane polypeptide fragment is a biologically active polypeptide fragment. In some instances, the biologically active polypeptide fragment is a functionally active polypeptide fragment, a structurally stable (e.g., thermal stable or pH stable) polypeptide fragment, or a combination thereof. In some cases, a multispanning membrane polypeptide comprises an integral membrane protein, a peripheral membrane protein, or a polypeptide toxin. In some cases, an integral membrane protein is further classified into an integral polytopic protein (or a transmembrane protein) or an integral monotopic protein. In some instances, an integral polytopic protein is a membrane protein that spans across the membrane at least once and falls under two tertiary structural classes: helix bundle protein or beta barrel protein. In some instances, an integral monotopic protein is a membrane protein that is attached to only one side of the membrane and does not span across the lipid bilayer.

In some embodiments, a modified multispanning membrane polypeptide comprises a plasma membrane protein, a nuclear membrane protein, a peripheral membrane protein, an intracellular-membrane protein, a transporter, a channel protein, an adhesin, a translocase, or a receptor. In some embodiments, a modified multispanning membrane polypeptide comprises a plasma membrane protein. In some cases, a plasma membrane protein comprises a membrane protein that anchors into the plasma membrane or the outermost layer of a cell. In some embodiments, a modified multispanning membrane polypeptide comprises a nuclear membrane protein. In some cases, a nuclear membrane protein comprises a membrane protein that associates with or is anchored into the membrane of the nuclear envelope. In some cases, a nuclear membrane protein further comprises an inner nuclear membrane protein, such as for example, lamin B receptor (LBR), lamina-associated polypeptide 1 (LAP1), lamina-associated polypeptide-2 (LAP2), emerin, and MAN1 (LEM domain-containing protein 3 or LEMD3). In some embodiments, a modified multispanning membrane polypeptide comprises a peripheral membrane protein. In some cases, a peripheral membrane protein comprises a membrane protein that adheres only temporarily to a biological membrane. For example, membrane proteins that interact with integral membrane proteins or that penetrate the peripheral regions of a lipid bilayer are sometimes referred to as peripheral membrane proteins. In addition, the regulatory subunits of ion channels or transmembrane receptors are sometimes referred to as peripheral membrane proteins. In some embodiments, a modified multispanning membrane polypeptide comprises an intracellular-membrane protein (e.g., a mitochondrial membrane protein). In some embodiments, a modified multispanning membrane polypeptide comprises a transporter. In some cases, a transporter comprises a transmembrane pump, an escort protein, an acid transport protein, a cation transport protein, or an anion transport protein. In some cases, a transporter is further referred to as a carrier protein. A carrier protein is a protein that ferries across ions, small molecules or macromolecules (e.g., proteins) across a biological membrane. In some instances, a carrier protein is a vesicular transport protein. A vesicular transport protein is a transmembrane protein that facilitates vesicle transport across a biological membrane. In some embodiments, a modified multispanning membrane polypeptide comprises a channel protein. In some cases, a channel protein comprises a protein that forms an aqueous pore that extends across the lipid bilayer which allows solutes such as ions or small molecules to transport across. In some instances, a channel protein comprises an ion channel protein. In some embodiments, a modified multispanning membrane polypeptide comprises an adhesin.

In some cases, an adhesin comprises a microbial cell-surface protein that adheres to a cell or surface of interest. In some embodiments, a modified multispanning membrane polypeptide comprises a translocase. In some cases, a translocase comprises a protein that assists in transporting another molecule, in some instances, across a biological membrane. In some embodiments, a modified multispanning membrane polypeptide comprises a receptor. In some instances, a receptor is further subdivided into four categories: Type 1 receptor or ionotropic receptor; Type 2 receptor or G protein-coupled receptor; Type 3 receptor or kinase linked and related receptors; and Type 4 receptor or nuclear receptor. In some instances, a receptor is a Type 1 receptor or ionotropic receptor (e.g., comprises a subgroup of ion channel proteins). In some instances, a receptor is a Type 2 receptor or G protein-coupled receptor. In some instances, a receptor is a Type 3 receptor or kinase linked and related receptor. In some instances, a receptor is a Type 4 receptor or nuclear receptor.

G Protein-Coupled Receptor

G protein-coupled receptor (GPCR), also known as seven-transmembrane domain receptor, 7TM receptor, heptahelical receptor, serpentine receptor, or G protein-linked receptor (GPLR), forms the GPCR Family of receptors under the transporter-opsin-G-protein-coupled receptor (TOG) superfamily. GPCR architecture comprises an extracellular N-terminal portion, a seven transmembrane (TM) core connected sequentially by three sets of exoloops (EL-1 to EL-3) and cytoloops (IL-1 to IL-3), and an intracellular C-terminal tail. In some cases, a fourth cytoplasmic loop is formed when the C-terminal tail is further palmitoylated at a cysteine residue. Upon ligand binding (e.g., interaction with ions, proteins, lipids, hormones, neurotransmitters, amines, nucleotides, odorant molecules, or photons), GPCR undergoes a conformational change which then activates a G protein (or guanine nucleotide-binding protein), e.g., induce dissociation of the G protein's α subunit from its β and γ subunits, thereby initiating a cascade of downstream signaling activations. In some cases, the intracellular signaling proteins and/or target functional proteins are modulated by the G protein's α subunit type, e.g., $G_{q/11}\alpha$, $G_{12/13}\alpha$, $G_{i/o}\alpha$ (G inhibitory, G other), and $G_s\alpha$ (G stimulatory). Sometimes, GPCRs are observed in eukaryotes, including chanoflagellates and yeast.

In some embodiments, GPCRs are further grouped into 6 classes based on sequence homology and functional similarity. In some cases, the 6 classes are Class A (or 1; rhodopsin-like) GPCR, Class B (or 2; secretin receptor family) GPCR, Class C (or 3; metabotropic glutamate/pheromone) GPCR, Class D (or 4; fungal mating pheromone receptors) GPCR, Class E (or 5; cyclic AMP receptors) GPCR, and Class F (or 6; Frizzled/Smoothened) GPCR.

Class A GPCRs (or Class 1) are the largest group of GPCRs comprising about 800 members. In some instances, rhodopsin-like GPCRs comprise hormones, neurotransmitters, and light receptors. In additional instances, rhodopsin-like GPCRs are further classified into 19 subgroups, Subfamily A1-A19. Exemplary Class A (rhodopsin-like) GPCRs include, but are not limited to, aminergic: acetylcholine (muscarinic acetylcholine receptors M1, M2, M3, M4, and M5), adrenergic (Alpha-1A, Alpha-1B, Alpha-1D, Alpha-2A, Alpha-2B, Alpha-2C-1, Beta-1, Beta-2, Beta-3), dopamine (D(1A), D(1B), D(2), D(3), D(4)), histamine (H1, H2, H3, H4), serotonin (5-HT-1A, 5-HT-1B, 5-HT-1D, 5-HT-1E, 5-HT-1F, 5-HT-2A, 5-HT-2B, 5-HT-2C, 5-HT-4, 5-HT-5A, 5-HT-6, 5-HT-7), cannabinoid (CB1, CB2), glycoprotein hormone (follicle stimulating hormone receptor (FSH-R), GPR24 melanin concentrating hormone receptor, lutropin-choriogonadotropic hormone receptor (LSH-R), GPCR0459 Melanin-concentrating hormone receptor 2 (MCH2), thyrotropin receptor (TSH-R)), lipid (eicosanoid (leukotriene (LTB (leukotriene B4 receptor (aka P2Y purinoceptor 7, P2Y7), leukotriene B4 receptor (aka Fishboy G-protein coupled receptor), and LTC (cysteinyl leukotriene receptor CysLT2), cysteinyl leukotriene receptor (CYSLT1)), prostanoid (CRTH2 (GPR44), prostacyclin receptor (prostanoid IP receptor), prostaglandin D2 receptor (prostanoid DP receptor), prostaglandin E2 receptor EP1 subtype (prostanoid EP1 receptor), prostaglandin E2 receptor EP2 subtype (prostanoid EP2 receptor), prostaglandin E2 receptor EP3 subtype (prostanoid EP3 receptor), prostaglandin E2 receptor EP4 subtype (prostanoid EP4 receptor), prostaglandin F2-alpha receptor (prostanoid FP receptor), thromboxane A2 receptor (TXA2-R) (prostanoid TP receptor)), lysophingolipid (EDG-4, EDG-1, EDG6, EDG-7, EDG-2, EDG-3, EDG5, EDG-8), sphingosylphosphorylcholine (OGR1), lysophosphatidylcholine (G2A)), melatonin (H9, MEL-1A-R, MEL-1B-R)), nucleotide (P2Y12 platelet ADP receptor), adenosine (A1, A2A, A2B, A3), nucleoside-sugar KIAA0001, UDP-Glucose), P2U (P2U1, P2Y2, P2Y1, P2Y11, P2Y6), olfactory (OR1A2, OR1A1, Olfactory receptor 17-90, OR17-24, 6M1-16*01/02/03, 6M1-18*01/02, 6M1-4P*02/05, Olfactory receptor 89, AC006271. AF143328, AL096770-01, AL096770-02, AL096770-03, AL096770-04, AL121944, AL135841, BC62940_2, BC85395_1, BC85395_3, F20569_1, F20722_1, F20722_2, FAT11, GPR1, GRIR-1, OR17-4, HGMP07I, HGMP07J, H17, HOR 5' beta, HOR 5' beta, HOR3'beta1, HPFH1OR, HS6M1-1, HS6M1-3, HS6M1-6, HSA1, HSA10, HSA3, HSA5, HSA8, OR16-35, H_DJ0855D21.1, H_DJ0988G15.2, JCG2, OLF1, OLF3, OLF4. OLFR 42B, OLFR42B, OLRCC15, OR1-25, OR1-26, OR10A1, OR17-201, OR17-209, OR17-210, OR17-219, OR17-228, OR17-30, OR17-40, OR2C1, OR2D2, OR5-40, OR5D3, OR5F1, OR6A1, OR7-138, R30385_1, TPCR100, TPCR110, TPCR120, TPCR16, TPCR24, TPCR25, TPCR26, TPCR27, TPCR85, TPCR92, Z98744, dJ25J6.1, dJ88J8.1, prostate specific olfactory receptor), putative taste receptor HTR2, opsin (blue-sensitive opsin, encephalopsin, green-sensitive opsin, melanopsin, RPE-retinal G protein-coupled receptor, red-sensitive opsin, rhodopsin, visual pigment-like receptor, peropsin), peptide (angiotensin (AT1, AT2), apelin (APJ), bombesin (BRS-3, GRP-R (GRP-preferring bombesin receptor), neuromedin-B receptor, NMB-R (neuromedin-B-preferring bombesin receptor)), bradykinin (BK-1 receptor, BK-2 receptor), chemokine (CC (CCR1, CCR10, CCR11, CCR2, CCR4, CCR5, CCR6, CCR7, CCR8, CCR9, CX3CR1, XCR1, CXCR3, CXCR4, CXCR5, FMET-LEU-PHE receptor (FMLP receptor), FMLP-related receptor I (FMLP-R-I), FMLP-related receptor II (FMLP-R-II), interleukin (CXCR1, CXCR2), anaphylatoxin (C3A-R, CSA-R)), cholecystokinin (CCK-A receptor, CCK-B receptor), endothelin (ET-B, ET-A), galanin (GAL1-R, GAL2-R, GAL3-R), melanocortin (MC1-R (MSH-R), MC2-R (ACTH-R), MC3-R, MC5-R)), motilin (GPR38 (Motilin Receptor)), neuropeptide (NPFF (NPFF2, RFamide-related peptide receptor), neuropeptide Y (NPY1-R, NPY2-R, NPY4-R, NPY5-R, NPY6-R), neurotensin (NTR1, NTR2), opioid (DOR-1, KOR-1, MOR-1, nociceptin receptor, KOR-3), orexin (orexin receptor type 1, OX1R (hypocretin receptor type 1), OX2R (Hypocretin receptor type 2)), other peptide (KiSS receptor (GPR54)), proteinase activated (PAR-2, PAR-3, PAR-4, thrombin receptor), somatostatin (SS5R, SS1R, SS2R, SS3R, SS4R), tachykinin (NK-3 receptor, NK-4 receptor, NMUIR (aka FM3), NMU2R, NK-2 receptor, NK-1 receptor), urotensin (Urotensin II receptor, GPR14), vasopressin (OT-R, vasopressin V1A receptor, vasopressin V1B receptor, vasopressin V2 receptor), platelet activating factor (leukocyte platelet-activating factor receptor, platelet activating factor receptor (PAF-R)), releasing Hormone (GNRH-R, GHS-R, Prolactin-releasing peptide receptor (GPR10), thyrotropin-releasing hormone receptor (TRH-R), Type II GnRH-R protein)).

In some instances, one or more Class A GPCRs are further classified as orphan GPCRs. In some instances, an orphan GPCR refers to a GPCR in which its endogenous ligand has not been identified. In such cases, when a ligand has been identified, the orphan status is then reassigned as adopted GPCR. Exemplary Class A orphan GPCRs include, but are not limited to, 5-hydroxytryptamine receptor homologue, transmembrane receptor HEOADS4, chemokine receptor, chemokine receptor-like 1, G-protein-coupled receptor DEZ, chemokine receptor-like 2, IL-8-related receptor DRYI2 GPR30 CEPR, dorsal root receptor 1 DRR1, dorsal root receptor 2 DRR2, dorsal root receptor 3 DRR3, dorsal root receptor 4 DRR4, dorsal root receptor 5 DRRS, dorsal root receptor 6 DRR6, Duffy antigen, EBV-induced G protein-coupled receptor 2 (EBI2), EDG homologue, EDG homologue (GPR45), EDG-homologue, GPR35, GPR37, GPR75, G protein-coupled receptor (RAIG1), BONZO (STRL33), D38449, ETBR-LP-2, GPR1, GPR12, GPR15, GPR17, GPR18, GPR19, GPR20, GPR22, GPR3 (ACCA "orphan" receptor), GPR31. GPR32, GPR34, GPR39, GPR4 (GPR19), GPR40, GPR41, GPR43, GPR55, GPR6, GPR7, GPR73, GPR8, HG38, HM74, LGR4, RDC 1 homolog, GPR48, GPR61, GPR62, GPR77, GPR84, GPR86, GPR87, GPR72, GPRC5B, H7TBA62, G-protein coupled receptor R97222, SALPR, Y13583, Y36302, GPR58, GPR57, RE2, GPR21, GPR52, SREB1, SREB2, SREB3, LGR7, MAS protooncogene, MAS-related G protein-coupled receptor MRG, neurotensin receptor ntr2 receptor homologue, GPR25, H963, P2Y10, P2Y5, P2Y9, FMLP related receptor homolog, pheromone receptor homologue, N-formyl peptide receptor homolog, GPR92, RAIG1 homolog, FKSG46, FKSG47, VIRL1, CRAM-A, FKSG80, seven transmembrane-domain protein p40 homologue TASP testis specific adriamycin sensitivity protein, striatum-specific G protein-coupled receptor, T cell-death associated protein, and thoracic aorta G-protein coupled receptor.

Class B GPCRs (or Class 2) comprise the secretin family of GPCRs. In some instances, the secretin receptors are regulated by peptide hormones from the glucagon hormone family. In some instances, exemplary Class B GPCRs include, but are not limited to, secretins (BAI-1, BAI-2, BAI-3), calcitonin gene-related peptide type 1 receptor, calcitonin receptor (CT-R), GIP-R, glucagon receptor (GL-R), glucagon-like peptide 1 receptor (GLP-1 receptor), glucagon-like peptide-2 receptor (GLP2R), growth hormone-releasing hormone receptor (GHRH receptor), leucocyte antigen CD97, ocular albinism type 1 protein, PTH2 receptor, PTHR receptor, PACAP-R-1, FMI1 (MEGF2), SCT-R, CRH (CRF1, CRF2), VIP (VIP-R-1, VIP-R-2).

In some cases, Class B orphan GPCRs include, for example, cadherin EGF LAG seven-pass G-type receptor (CELSR1), cell surface glycoprotein EMR1, class B G protein-coupled receptor Y91625, EGF-like module containing mucin-like receptor EMR3, flamingo 1 (FMI1), EMR2, FLJ14454, KIAA1828, AL033377 (HE6 homolog), ETL, GPR56, HE6, KIAA0758, latrophilin-1, latrophilin-2, latrophilin-3, VLGR1.

Class C GPCRs (or Class 3) comprise the metabotropic glutamatepheromone family of GPCRs. In some instances, exemplary Class C GPCRs include, but are not limited to, metabotropic calcium-sensing receptor (CASR), metabotropic glutamate receptor 1, metabotropic glutamate receptor 2, metabotropic glutamate receptor 3, metabotropic glutamate receptor 4, metabotropic glutamate receptor 5, metabotropic glutamate receptor 6, metabotropic glutamate receptor 7, metabotropic glutamate receptor 8, sensory transduction G-protein coupled receptor-B3, taste receptor GPCR-B4, and GABA-B (GABA-B1A receptor, GABA-B2 receptor).

Class D GPCRs (or Class 4) comprise the fungal mating pheromone receptors. Exemplary mating factor receptors include STE2 and STE3.

Class E GPCRs (or Class 5) comprise the cyclic AMP receptors.

Class F GPCRs (or Class 6) comprise Frizzled/Smoothened family of GPCRs.

Exemplary Class F GPCRs include, but are not limited to, frizzled 1 transmembrane receptor, frizzled 10 transmembrane receptor, frizzled 2 transmembrane receptor, frizzled 3 transmembrane receptor, frizzled 4 transmembrane receptor, frizzled 5 transmembrane receptor, frizzled 6 transmembrane receptor, frizzled 7 transmembrane receptor, frizzled 9 transmembrane receptor, frizzled-like receptor smoothened homolog (SMO), and frizzled-7 homologue.

In some embodiments, a GPCR described herein further comprise a taste GPCR. Exemplary taste GPCRs include, but are not limited to, T2R1, T2R10, T2R13, T2R14, T2R16, T2R3, T2R4, T2R5, T2R7, T2R8, and T2R9.

In some embodiments, a receptor is a GPCR. In some cases, a modified multispanning membrane polypeptide is a GPCR. In some instances, a modified multispanning membrane polypeptide is a Class A, Class B, Class C, Class D, Class E, or a Class F GPCR. In some cases, a modified multispanning membrane polypeptide is a taste GPCR. In some instances, a modified multispanning membrane polypeptide is a modified CCR7, CCR10, GPR55, NTR1, EP2, or EP4 receptor.

Ion Channel Polypeptides

An ion channel protein is a pore-forming membrane protein which modulates the flow of ions across a cell membrane, regulates cell volume, and establishes a resting membrane potential. In some instances, an ion channel protein comprises a voltage-gated ion channel or a ligand-gated ion channel. In some cases, an ion channel protein comprises a calcium-activated potassium channel, a CatSper and Two-Pore channel, a cyclic nucleotide-regulated channel, an inwardly rectifying potassium channel, a ryanodine receptor, a transient receptor potential channel, a two-P potassium channel, a voltage-gated calcium channel, a voltage-gated potassium channel, a voltage-gated proton channel, a voltage-gated sodium channel, 5-HT$_3$ receptor, an acid-sensing (proton-gated) ion channel (ASIC), an epithelial sodium channel (ENaC), GABA$_A$ receptor, a glycine receptor, an ionotropic glutamate receptor, IP$_3$ receptor, a nicotinic acetylcholine receptor, P2X receptor, or ZAC.

In some embodiment, a receptor is an ion channel polypeptide. In some cases, a modified multispanning membrane polypeptide is an ion channel polypeptide. In some cases, a modified multispanning membrane polypeptide comprises an ion channel polypeptide selected from a calcium-activated potassium channel, a CatSper and Two-Pore channel, a cyclic nucleotide-regulated channel, an inwardly rectifying potassium channel, a ryanodine receptor, a transient receptor potential channel, a two-P potassium channel, a voltage-gated calcium channel, a voltage-gated potassium channel, a voltage-gated proton channel, a voltage-gated sodium channel, 5-HT$_3$ receptor, an acid-sensing (proton-gated) ion channel (ASIC), an epithelial sodium channel (ENaC), GABA$_A$ receptor, a glycine receptor, an ionotropic glutamate receptor, IP$_3$ receptor, a nicotinic acetylcholine receptor, P2X receptor, or ZAC. In some cases, a modified multispanning membrane polypeptide comprises a modified TRPV3, KCa3.1, or TRPC6.

Platform for Generating a Modified Membrane-Spanning Polypeptide

Disclosed herein, in certain embodiments, are methods and platform for generating a modified multispanning membrane polypeptide with an improved or enhanced physicochemical property. In some instances, a method or a platform described herein comprises generating a modified multispanning membrane polypeptide by a mutagenesis method, inserting a polynucleotide encoding the modified multispanning membrane polypeptide into an expression vector comprising a C-terminal selection marker and optionally an N-terminal selection marker, and expressing the vector in a host cell in the presence or absence of at least one selection agent to identify a stably folded modified multispanning membrane polypeptide.

In some instances, a method and platform described herein for generating a modified multispanning membrane polypeptide with an improved or enhanced physicochemical property is as illustrated in FIG. 1. In some instances, a method or platform comprises generating a modified multispanning membrane polypeptide by a mutagenesis method (101). In some instances, the mutagenesis method is a random mutagenesis. Exemplary random mutagenesis comprises error-prone PCR, rolling circle error-prone PCR, mutator strains, temporary mutator strains, insertion mutagenesis, ethyl methanesulfonate, nitrous acid, or DNA shuffling. In some instances, the mutagenesis method is an error-prone PCR method. In some instances, the mutagenesis method is a DNA shuffling method. In other instances, the mutagenesis method is a non-random mutagenesis method. Upon generation of a library, each modified multispanning membrane polypeptide within the library is then encoded in an expression vector for undergoing a selection process (102). In some instances, the expression vector further comprises a first selection marker, which is located at the C-terminus of the modified multispanning membrane polypeptide. Such selection marker sometimes selects against premature truncations of the multispanning membrane polypeptide and/or facilitates stable and correct folding of the multispanning membrane polypeptide. In some cases, the expression vector optionally comprises a second selection marker, which is located at the N-terminus of the modified multispanning membrane polypeptide. In some cases, the presence of the second selection marker facilitates stable and correct folding of the multispanning membrane polypeptide. In some instances, misfolded polypeptide is further tagged and removed by the host cell machinery for degradation. In some instances, the first selection marker encodes a first selection polypeptide and the second selection marker encodes a second selection polypeptide. In some instances, the expression vector is expressed in a host cell in the presence or absence of at least one selection agent (e.g., in the presence of an antibiotics or in the absence of an auxotrophic agent). In some cases, the at least one selection agent is rendered non-toxic to the host cells by interaction with the first selection polypeptide and with the second selection polypeptide when the first selection polypeptide is properly displayed on the C-terminal portion of the modified multispanning membrane polypeptide and the second selection polypeptide is properly displayed on the N-terminal portion of the modified multispanning membrane polypeptide. In some instances, the at least one selection agent comprises an antibiotic (e.g., ampicillin, carbenicillin, gentamicin, chloramphenicol, neomycin, kanamycin, streptomycin, erythromycin, or tetracycline) or a toxic metabolite (e.g., 5-fluoroorotic acid or 3-amino-1,2,4-triazole). In some instances, the at least one selection agent comprises elevated temperature, reduced temperature, a lack of nutrient, or a lack of co-factor. In some instances from the selection process (102), a modified multispanning membrane polypeptide is identified for undergoing additional rounds of random mutagenesis (101) (e.g., 2, 3, 4, 5, or more rounds of random mutagenesis) and selection process (102) to identify a minimum set of mutations that are able to convey a physicochemical property of interest. In other instances from the selection process (102), a modified multispanning membrane polypeptide is identified for expression and characterization (103). In some instances, one or more of physicochemical properties are evaluated, e.g., one or more of expression level, stability, conformational selectivity, homogeneity, protein crystallization, antigenicity, immunogenicity, or pathway activation selectivity. In some instances, enhanced physicochemical properties such as increased stability (e.g., thermostability or pH stability) and improved propensity for protein in forming crystals further correlates to improved immunogenicity and antigenicity. In some instances, the one or more analytical techniques are utilized for the characterization process (103) and comprise X-ray crystallography, electron crystallography, cryo electron microscopy, nuclear magnetic resonance spectroscopy (NMR), thermal denaturing techniques, and/or chemical denaturing techniques. In some cases, from the expression and characterization step (103), a candidate modified multispanning membrane polypeptide is identified for large scale protein production (104), followed by crystallization (105) of the candidate modified multispanning membrane polypeptide, small molecule screening (106), antibody and/or peptide screening (107), and/or vaccine production (108). In some instances, a candidate modified multispanning membrane polypeptide is produced in an insect host cell or a mammalian host cell. In some instances, a phage display or a yeast display is used for the antibody screening and a candidate modified multispanning membrane polypeptide is immobilized on a nanoparticle during the screening process. In some instances, an antibody identified from the antibody screen (107) is further formulated for a vaccine. In some instances, a peptide of a candidate modified multispanning membrane polypeptide identified from a peptide screening (107) is further formulated for a vaccine. In other instances, a candidate modified multispanning membrane polypeptide produced from the protein production step (104) is further formulated for a vaccine (e.g., a nucleic acid-based vaccine, an antigen-presenting cell (APC) based vaccine, or a virus based vaccine).

Modified Multispanning Membrane Polypeptides

In some instances, a modified multispanning membrane polypeptide comprises one or more modifications. In some instances, a modified multispanning membrane polypeptide comprises from about 1 to about 100 modifications. In some cases, a modified multispanning membrane polypeptide comprises from about 1 to about 90, from about 5 to about 80, from about 10 to about 70, from about 15 to about 60, from about 20 to about 50, from about 30 to about 40, from about 1 to about 80, from about 1 to about 60, from about 1 to about 50, from about 1 to about 40, from about 1 to about 30, from about 1 to about 15, from about 1 to about 10, from about 10 to about 80, from about 10 to about 60, from about 10 to about 50, from about 10 to about 40, from about 20 to about 80, from about 20 to about 40, from about 30 to about 80, from about 30 to about 60, or from about 30 to about 50 modifications. In some instances, a modified multispanning membrane polypeptide comprises about 1, 2, 3, 4, 5, 6, 7, 8, 9, 10, 11, 12, 13, 14, 15, 16, 17, 18, 19, 20, 25, 30, 35, 40, 45, 50, or more modified amino acid residues.

In some cases, a modified multispanning membrane polypeptide comprises a plasma membrane protein, a nuclear membrane protein, a peripheral membrane protein, an intracellular-membrane protein, a transporter, a channel protein (e.g., an ion channel protein), an adhesin, a translocase, or a receptor. In some cases, a modified multispanning membrane polypeptide selected from a plasma membrane protein, a nuclear membrane protein, a peripheral membrane protein, an intracellular-membrane protein, a transporter, a channel protein (e.g., an ion channel protein), an adhesin, a translocase, or a receptor comprises from about 1 to about 100 modifications. In some cases, a modified multispanning membrane polypeptide selected from a plasma membrane protein, a nuclear membrane protein, a peripheral membrane protein, an intracellular-membrane protein, a transporter, a channel protein (e.g., an ion channel protein), an adhesin, a translocase, or a receptor comprises from about 1 to about 90, from about 5 to about 80, from about 10 to about 70, from about 15 to about 60, from about 20 to about 50, from about 30 to about 40, from about 1 to about 80, from about 1 to about 60, from about 1 to about 50, from about 1 to about 40, from about 1 to about 30, from about 1 to about 15, from about 1 to about 10, from about 10 to about 80, from about 10 to about 60, from about 10 to about 50, from about 10 to about 40, from about 20 to about 80, from about 20 to about 60, from about 20 to about 40, from about 30 to about 80, from about 30 to about 60, or from about 30 to about 50 modifications. In some instances, a modified multispanning membrane polypeptide selected from a plasma membrane protein, a nuclear membrane protein, a peripheral membrane protein, an intracellular-membrane protein, a transporter, a channel protein (e.g., an ion channel protein), an adhesin, a translocase, or a receptor comprises about 1, 2, 3, 4, 5, 6, 7, 8, 9, 10, 11, 12, 13, 14, 15, 16, 17, 18, 19, 20, 25, 30, 35, 40, 45, 50, or more modified amino acid residues.

In some embodiments, a modified multispanning membrane polypeptide is an ion channel protein. In some instances, an ion channel protein comprises from about 1 to about 100 modifications. In some cases, an ion channel protein comprises from about 1 to about 90, from about 5 to about 80, from about 10 to about 70, from about 15 to about 60, from about 20 to about 50, from about 30 to about 40, from about 1 to about 80, from about 1 to about 60, from about 1 to about 50, from about 1 to about 40, from about 1 to about 30, from about 1 to about 15, from about 1 to about 10, from about 10 to about 80, from about 10 to about 60, from about 10 to about 50, from about 10 to about 40, from about 20 to about 80, from about 20 to about 60, from about 20 to about 40, from about 30 to about 80, from about 30 to about 60, or from about 30 to about 50 modifications.

In some instances, an ion channel protein comprises about 1, 2, 3, 4, 5, 6, 7, 8, 9, 10, 11, 12, 13, 14, 15, 16, 17, 18, 19, 20, 25, 30, 35, 40, 45, 50, or more modified amino acid residues. In some instances, an ion channel protein comprises about 1 or more modified amino acid residues. In some instances, an ion channel protein comprises about 2 or more modified amino acid residues. In some instances, an ion channel protein comprises about 3 or more modified amino acid residues. In some instances, an ion channel protein comprises about 4 or more modified amino acid residues. In some instances, an ion channel protein comprises about 5 or more modified amino acid residues. In some instances, an ion channel protein comprises about 6 or more modified amino acid residues. In some instances, an ion channel protein comprises about 7 or more modified amino acid residues. In some instances, an ion channel protein comprises about 8 or more modified amino acid residues. In some instances, an ion channel protein comprises about 9 or more modified amino acid residues. In some instances, an ion channel protein comprises about 10 or more modified amino acid residues. In some instances, an ion channel protein comprises about 11 or more modified amino acid residues. In some instances, an ion channel protein comprises about 12 or more modified amino acid residues. In some instances, an ion channel protein comprises about 13 or more modified amino acid residues. In some instances, an ion channel protein comprises about 14 or more modified amino acid residues. In some instances, an ion channel protein comprises about 15 or more modified amino acid residues. In some instances, an ion channel protein comprises about 16 or more modified amino acid residues. In some instances, an ion channel protein comprises about 17 or more modified amino acid residues. In some instances, an ion channel protein comprises about 18 or more modified amino acid residues. In some instances, an ion channel protein comprises about 19 or more modified amino acid residues. In some instances, an ion channel protein comprises about 20 or more modified amino acid residues. In some instances, an ion channel protein comprises about 25 or more modified amino acid residues. In some instances, an ion channel protein comprises about 30 or more modified amino acid residues. In some instances, an ion channel protein comprises about 35 or more modified amino acid residues. In some instances, an ion channel protein comprises about 40 or more modified amino acid residues. In some instances, an ion channel protein comprises about 45 or more modified amino acid residues. In some instances, an ion channel protein comprises about 50 or more modified amino acid residues.

In some embodiments, a modified multispanning membrane polypeptide is a receptor. In some cases, a receptor is a GPCR. In some instances, a GPCR comprises from about 1 to about 100 modifications. In some cases, a GPCR comprises from about 1 to about 90, from about 5 to about 80, from about 10 to about 70, from about 15 to about 60, from about 20 to about 50, from about 30 to about 40, from about 1 to about 80, from about 1 to about 60, from about 1 to about 50, from about 1 to about 40, from about 1 to about 30, from about 1 to about 15, from about 1 to about 10, from about 10 to about 80, from about 10 to about 60, from about 10 to about 50, from about 10 to about 40, from about 20 to about 80, from about 20 to about 60, from about 20 to about 40, from about 30 to about 80, from about 30 to about 60, or from about 30 to about 50 modifications.

In some instances, a GPCR comprises about 1, 2, 3, 4, 5, 6, 7, 8, 9, 10, 11, 12, 13, 14, 15, 16, 17, 18, 19, 20, 25, 30, 35, 40, 45, 50, or more modified amino acid residues. In some instances, a GPCR comprises about 1 or more modified amino acid residues. In some instances, a GPCR comprises about 2 or more modified amino acid residues. In some instances, a GPCR comprises about 3 or more modified amino acid residues. In some instances, a GPCR comprises about 4 or more modified amino acid residues. In some instances, a GPCR comprises about 5 or more modified amino acid residues. In some instances, a GPCR comprises about 6 or more modified amino acid residues. In some instances, a GPCR comprises about 7 or more modified amino acid residues. In some instances, a GPCR comprises about 8 or more modified amino acid residues. In some instances, a GPCR comprises about 9 or more modified amino acid residues. In some instances, a GPCR comprises about 10 or more modified amino acid residues. In some instances, a GPCR comprises about 11 or more modified amino acid residues. In some instances, a GPCR comprises about 12 or more modified amino acid residues. In some instances, a GPCR comprises about 13 or more modified amino acid residues. In some instances, a GPCR comprises about 14 or more modified amino acid residues. In some instances, a GPCR comprises about 15 or more modified amino acid residues. In some instances, a GPCR comprises about 16 or more modified amino acid residues. In some instances, a GPCR comprises about 17 or more modified amino acid residues. In some instances, a GPCR comprises about 18 or more modified amino acid residues. In some instances, a GPCR comprises about 19 or more modified amino acid residues. In some instances, a GPCR comprises about 20 or more modified amino acid residues. In some instances, a GPCR comprises about 25 or more modified amino acid residues. In some instances, a GPCR comprises about 30 or more modified amino acid residues. In some instances, a GPCR comprises about 35 or more modified amino acid residues. In some instances, a GPCR comprises about 40 or more modified amino acid residues. In some instances, a GPCR comprises about 45 or more modified amino acid residues. In some instances, a GPCR comprises about 50 or more modified amino acid residues.

In some embodiments, a modified multispanning membrane polypeptide comprises about 0.5%, 1%, 2%, 3%, 4%, 5%, 6%, 7%, 8%, 9%, 10%, 11%, 12%, 13%, 14%, 15%, 20%, 25%, 30%, or more modifications. In some cases, a modified multispanning membrane polypeptide comprises a plasma membrane protein, a nuclear membrane protein, a peripheral membrane protein, an intracellular-membrane protein, a transporter, a channel protein (e.g., an ion channel protein), an adhesin, a translocase, or a receptor. In some instances, a modified multispanning membrane polypeptide selected from a plasma membrane protein, a nuclear membrane protein, a peripheral membrane protein, an intracellular-membrane protein, a transporter, a channel protein (e.g., an ion channel protein), an adhesin, a translocase, or a receptor comprises about 0.5%, 1%, 2%, 3%, 4%, 5%, 6%, 7%, 8%, 9%, 10%, 11%, 12%, 13%, 14%, 15%, 20%, 25%, 30%, or more modifications.

In some embodiments, a modified multispanning membrane polypeptide is an ion channel protein. In some embodiments, an ion channel protein comprises about 0.5%, 1%, 2%, 3%, 4%, 5%, 6%, 7%, 8%, 9%, 10%, 11%, 12%, 13%, 14%, 15%, 20%, 25%, 30%, or more modifications. In some embodiments, an ion channel protein comprises about 0.5% or more modifications. In some embodiments, an ion channel protein comprises about 1% or more modifications. In some embodiments, an ion channel protein comprises about 2% or more modifications. In some embodiments, an ion channel protein comprises about 3% or more modifications. In some embodiments, an ion channel protein comprises about 4% or more modifications. In some embodiments, an ion channel protein comprises about 5% or more modifications. In some embodiments, an ion channel protein comprises about 6% or more modifications. In some embodiments, an ion channel protein comprises about 7% or more modifications. In some embodiments, an ion channel protein comprises about 8% or more modifications. In some embodiments, an ion channel protein comprises about 9% or more modifications. In some embodiments, an ion channel protein comprises about 10% or more modifications. In some embodiments, an ion channel protein comprises about 11% or more modifications. In some embodiments, an ion channel protein comprises about 12% or more modifications. In some embodiments, an ion channel protein comprises about 13% or more modifications. In some embodiments, an ion channel protein comprises about 14% or more modifications. In some embodiments, an ion channel protein comprises about 15% or more modifications. In some embodiments, an ion channel protein comprises about 20% or more modifications. In some embodiments, an ion channel protein comprises about 25% or more modifications. In some embodiments, an ion channel protein comprises about 30% or more modifications.

In some embodiments, a modified multispanning membrane polypeptide is a receptor. In some cases, a receptor is a GPCR. In some embodiments, a GPCR comprises about 0.5%, 1%, 2%, 3%, 4%, 5%, 6%, 7%, 8%, 9%, 10%, 11%, 12%, 13%, 14%, 15%, 20%, 25%, 30%, or more modifications. In some embodiments, a GPCR comprises about 0.5% or more modifications. In some embodiments, a GPCR comprises about 1% or more modifications. In some embodiments, a GPCR comprises about 2% or more modifications. In some embodiments, a GPCR comprises about 3% or more modifications. In some embodiments, a GPCR comprises about 4% or more modifications. In some embodiments, a GPCR comprises about 5% or more modifications. In some embodiments, a GPCR comprises about 6% or more modifications. In some embodiments, a GPCR comprises about 7% or more modifications. In some embodiments, a GPCR comprises about 8% or more modifications. In some embodiments, a GPCR comprises about 9% or more modifications. In some embodiments, a GPCR comprises about 10% or more modifications. In some embodiments, a GPCR comprises about 11% or more modifications. In some embodiments, a GPCR comprises about 12% or more modifications. In some embodiments, a GPCR comprises about 13% or more modifications. In some embodiments, a GPCR comprises about 14% or more modifications. In some embodiments, a GPCR comprises about 15% or more modifications. In some embodiments, a GPCR comprises about 20% or more modifications. In some embodiments, a GPCR comprises about 25% or more modifications. In some embodiments, a GPCR comprises about 30% or more modifications.

In some embodiments, one or more modifications are located at the N-terminal portion of a GPCR, the transmembrane core (TM) of a GPCR, the C-terminal portion of a GPCR, or a combination thereof. In some instances, at least 1, 2, 3, 4, 5, 6, 7, 8, 9, 10, 15, or more modifications are located at the N-terminal portion of a GPCR. In some cases, at least 1, 2, 3, 4, 5, 6, 7, 8, 9, 10, 15, or more modifications are located within the TM of a GPCR, e.g., within TM1, TM2, TM3, TM4, TM5, TM6, TM7, or a combination thereof. In additional cases, at least 1, 2, 3, 4, 5, 6, 7, 8, 9, 10, 15, or more modifications are located at the C-terminal portion of a GPCR.

In some embodiments, a modification described supra correlates to an enhanced or improved physicochemical property of a multispanning membrane polypeptide relative to its wild-type. In some instances, a physicochemical property comprises expression level, stability, conformational selectivity, homogeneity, protein crystallization, antigenicity, immunogenicity, and/or pathway activation selectivity. In some cases, a modification described supra correlates to an enhanced or improved physicochemical property of a multispanning membrane polypeptide relative to its wild-type, in which the physicochemical property is selected from expression level, stability, conformational selectivity, homogeneity, protein crystallization, antigenicity, immunogenicity, and/or pathway activation selectivity. In some cases, the multispanning membrane polypeptide is an ion channel protein or a GPCR. In some cases, a modification described supra correlates to an enhanced or improved physicochemical property of an ion channel protein relative to its wild-type, in which the physicochemical property is selected from expression level, stability, conformational selectivity, homogeneity, protein crystallization, antigenicity, immunogenicity, and/or pathway activation selectivity. In additional cases, a modification described supra correlates to an enhanced or improved physicochemical property of a GPCR relative to its wild-type, in which the physicochemical property is selected from expression level, stability, conformational selectivity, homogeneity, protein crystallization, antigenicity, immunogenicity, and/or pathway activation selectivity.

In some embodiments, a physicochemical property is improved or enhanced expression level. In some instances, a modification described supra correlates to an enhanced or improved expression level of a multispanning membrane polypeptide relative to its wild-type. In some cases, the multispanning membrane polypeptide is an ion channel protein or a GPCR. In some instances, a modification described supra correlates to an enhanced or improved expression level of an ion channel protein relative to its wild-type. In some instances, a modification described supra correlates to an enhanced or improved expression level of a GPCR relative to its wild-type.

In some embodiments, a physicochemical property is improved or enhanced stability. In some cases, stability further comprises pH stability and thermostability. In some cases, pH stability of a multispanning membrane polypeptide is the ability of the polypeptide to remain folded and retains a biological function (e.g., a biological activity) at a defined pH range. In some instances, a defined pH range is from about 1 to about 11, from about 3 to about 9, from about 4 to about 9, from about 5 to about 9, from about 6 to about 9, or from about 7 to about 9. In some cases, a defined pH is at least about 1, 2, 2.5, 3, 3.5, 4, 4.5, 5, 5.5, 6, 6.5, 7, 7.5, 8, 8.5, 9, 9.5, 10, 11, or more.

In some cases, thermostability of a multispanning membrane polypeptide is the ability of the polypeptide to remain folded and retain a biological function (e.g., a biological activity) at a defined temperature. In some instances, a defined temperature range is from about 0° C. to about 120° C., from about 10° C. to about 100° C., from about 15° C. to about 80° C., from about 20° C. to about 60° C., from about 25° C. to about 50° C., from about 30° C. to about 40° C., from about 15° C. to about 37° C., from about 20° C. to about 37° C., from about 25° C. to about 37° C., from about 25° C. to about 50° C., or from about 37° C. to about 50° C. In some cases, a defined temperature is at least about 1° C., 4° C., 5° C., 8° C., 10° C., 15° C., 16° C., 18° C., 20° C., 25° C., 30° C., 35° C., 37° C., 40° C., 42° C., 45° C., 50° C., 55° C., 60° C., 65° C., 70° C., 80° C., 90° C., 100° C., or more.

In some instances, thermostability of a multispanning membrane polypeptide is further associated with the melting point of the multispanning membrane polypeptide. In some cases, a melting point curve is generated by heating a multispanning membrane polypeptide sample and measuring the extent of unfolding, inactivation, aggregation, or degradation utilizing techniques such as thermal shift assays (e.g. fluorescence shift using dyes), differential scanning calorimetry, circular dichroism, peak shift assays (based on HPLC/size exclusion chromatography) and the like. In some cases, thermostability refers to an increased melting point (or melting temperature) of a modified multispanning membrane polypeptide relative to its wild-type. In some cases, the increase is an increase of about 1, 2, 3, 4, 5, 6, 7, 8, 9, 10, 11, 12, 13, 14, 15, 20, 25, 30, or more degrees in temperature.

In some cases, the stability further comprises stability of a multispanning membrane polypeptide in a range of detergents, surfactants, and solubilization buffers which enables its purification outside of its normal membrane environment. Thus, the multispanning membrane polypeptide is provided in an isolated form removed from non-desired antigens such as non-target membrane proteins, membrane associated proteins or other membrane components such as lipoproteins, apolipoproteins, lipids, phosphoinositol lipids, and liposaccharides.

In some instances, a modification described supra correlates to an enhanced or improved stability (e.g., pH stability or thermostability) of a multispanning membrane polypeptide relative to its wild-type. In some cases, the multispanning membrane polypeptide is an ion channel protein or a GPCR. In some instances, a modification described supra correlates to an enhanced or improved stability (e.g., pH stability or thermostability) of an ion channel protein relative to its wild-type. In some instances, a modification described supra correlates to an enhanced or improved stability (e.g., pH stability or thermostability) of a GPCR relative to its wild-type.

In some embodiments, a physicochemical property is improved or enhanced conformational selectivity. In some instances, a modification described supra correlates to an enhanced or improved conformational selectivity of a multispanning membrane polypeptide relative to its wild-type. In some cases, the multispanning membrane polypeptide is an ion channel protein or a GPCR. In some instances, a modification described supra correlates to an enhanced or improved conformational selectivity of an ion channel protein relative to its wild-type. In some instances, a modification described supra correlates to an enhanced or improved conformational selectivity of a GPCR relative to its wild-type.

In some embodiments, a physicochemical property is improved or enhanced homogeneity. In some instances, homogeneity refers to a structural similarity or uniformity and/or a uniformity of one or more physicochemical properties within a population of multispanning membrane polypeptides. In some instances, a reduced protein conformational variability of a multispanning membrane polypeptide correlates to an increase or a higher degree of homogeneity of the multispanning membrane polypeptide within a sample. In other instances, an increase in degradation and/or unfolding of a multispanning membrane polypeptide correlates to a decrease in homogeneity of the multispanning membrane polypeptide within a sample.

In some instances, a modification described supra correlates to an enhanced or improved homogeneity of a multispanning membrane polypeptide relative to its wild-type. In some cases, the multispanning membrane polypeptide is an ion channel protein or a GPCR. In some instances, a modification described supra correlates to an enhanced or improved homogeneity of an ion channel protein relative to its wild-type. In some instances, a modification described supra correlates to an enhanced or improved homogeneity of a GPCR relative to its wild-type.

In some embodiments, a physicochemical property is improved or enhanced protein crystallization. In some instances, improved or enhanced protein crystallization refers to the propensity of a multispanning membrane polypeptide to be readily crystallized. For example, multispanning membrane polypeptides and their complexes are prompted to form crystals under supersaturated conditions. Under these conditions, individual protein molecules are packed in a repeating array, held together by noncovalent interactions. These crystals are then used in structural biology to study the molecular structure of the protein, and/or for industrial or biotechnological purposes. In some instances, protein crystallization is considered challenging due to the restrictions of the aqueous environment, difficulties in obtaining high-quality protein samples, or factors such as sensitivity of protein samples to temperature, pH, and ionic strength. In some instances, multispanning membrane proteins within a same group of multispanning membrane proteins vary in their physicochemical characteristics, and as such crystallization of a particular protein of interest is not predictable. Determination of appropriate crystallization conditions for a given protein in some cases requires empirical testing of many conditions before a successful crystallization condition is found. In some cases, improved or enhanced protein crystallization described herein refers to increased high-quality protein samples, increased protein crystals diffractions, reduced heterogeneity, or improved stability.

In some instances, a modification described supra correlates to an enhanced or improved protein crystallization of a multispanning membrane polypeptide relative to its wild-type. In some cases, the multispanning membrane polypeptide is an ion channel protein or a GPCR. In some instances, a modification described supra correlates to an enhanced or improved protein crystallization of an ion channel protein relative to its wild-type. In some instances, a modification described supra correlates to an enhanced or improved protein crystallization of a GPCR relative to its wild-type.

In some embodiments, a physicochemical property is improved or enhanced antigenicity. In some instances, antigenicity is the ability of a chemical structure (e.g., an antigen) to interact or to bind specifically to an antibody or its binding fragment thereof or to a product of a humoral and/or cell mediated immune response.

In some instances, a modification described supra correlates to an enhanced or improved antigenicity of a multispanning membrane polypeptide relative to its wild-type. In some cases, the multispanning membrane polypeptide is an ion channel protein or a GPCR. In some instances, a modification described supra correlates to an enhanced or improved antigenicity of an ion channel protein relative to its wild-type. In some instances, a modification described supra correlates to an enhanced or improved antigenicity of a GPCR relative to its wild-type.

In some embodiments, a physicochemical property is improved or enhanced immunogenicity. In some cases, immunogenicity is the ability of a chemical structure (e.g., an immunogen) to induce humoral and/or cell mediated immune response.

In some instances, a modification described supra correlates to an enhanced or improved immunogenicity of a multispanning membrane polypeptide relative to its wild-type. In some cases, the multispanning membrane polypeptide is an ion channel protein or a GPCR. In some instances, a modification described supra correlates to an enhanced or improved immunogenicity of an ion channel protein relative to its wild-type. In some instances, a modification described supra correlates to an enhanced or improved immunogenicity of a GPCR relative to its wild-type.

In some embodiments, a physicochemical property is improved or enhanced pathway activation selectivity. In some instances, improved or enhanced pathway activation selectivity refers to the ability of a multispanning membrane polypeptide to selectively activate one or more number of metabolic or signaling pathways from among a plurality of available metabolic or signaling pathways.

In some instances, a modification described supra correlates to an enhanced or improved pathway activation selectivity of a multispanning membrane polypeptide relative to its wild-type. In some cases, the multispanning membrane polypeptide is an ion channel protein or a GPCR. In some instances, a modification described supra correlates to an enhanced or improved pathway activation selectivity of an ion channel protein relative to its wild-type. In some instances, a modification described supra correlates to an enhanced or improved pathway activation selectivity of a GPCR relative to its wild-type.

In some embodiments, improved thermostability and/or homogeneity further modulates (e.g., improves) the protein crystallization, antigenicity, immunogenicity, pathway activation selectivity, and/or other physicochemical properties of a modified multispanning membrane polypeptide described herein.

In some embodiments, a modification comprises an insertion, a deletion, or a mutation. In some instances, a modified multispanning membrane polypeptide comprises an insertion, a deletion, a mutation, or a combination thereof. In some cases, the mutation comprises a nonsense mutation or a missense mutation. In some cases, a modified multispanning membrane polypeptide further comprises a truncation. In some cases, a truncation is located at the N-terminus of the modified multispanning membrane polypeptide, the C-terminus of the modified multispanning membrane polypeptide, or at both termini. In some cases, a modified multispanning membrane polypeptide also comprises an internal deletion or insertion. In some cases, a modified multispanning membrane polypeptide comprises an internal deletion. In other cases, a modified multispanning membrane polypeptide comprises an internal insertion.

In some instances, a modification comprises a mutation to a hydrophobic or nonpolar amino acid residue. In some cases, a hydrophobic or nonpolar amino acid includes small hydrophobic amino acids and large hydrophobic amino acids. Exemplary small hydrophobic amino acids include glycine, alanine, proline, and analogs thereof. Exemplary large hydrophobic amino acids include valine, leucine, isoleucine, phenylalanine, methionine, tryptophan, and analogs thereof. In some instances, a modified multispanning membrane polypeptide described herein comprises a mutation to a small hydrophobic amino acid (e.g., a mutation to glycine, alanine, proline, and analogs thereof). In some instances, a modified multispanning membrane polypeptide described herein comprises a mutation to a large hydrophobic amino acid (e.g., a mutation to valine, leucine, isoleucine, phenylalanine, methionine, tryptophan, and analogs thereof).

In some instances, a modification comprises a mutation to a polar amino acid residue. In some cases, the polar amino acid comprises serine, threonine, asparagine, glutamine, cysteine, tyrosine, and analogs thereof. In some instances, a modified multispanning membrane polypeptide described herein comprises a mutation to a polar amino acid residue (e.g., a mutation to serine, threonine, asparagine, glutamine, cysteine, tyrosine, and analogs thereof).

In additional instances, a modification comprises a mutation to a charged amino acid residue. In some cases, charged amino acids include lysine, arginine, histidine, aspartate, glutamate, or analog thereof. In some instances, a modified multispanning membrane polypeptide described herein comprises a mutation to a charged amino acid residue (e.g., a mutation to lysine, arginine, histidine, aspartate, glutamate, or analog thereof).

In some embodiments, a modified multispanning membrane polypeptide described herein comprises a modification to a non-essential amino acid. In some instances, a non-essential amino acid residue is a residue that is altered from the wild-type sequence of a polypeptide without abolishing or substantially altering its essential biological or biochemical activity (e.g., receptor binding or activation). In some cases, a modified multispanning membrane polypeptide provided herein comprises an essential amino acid. In some cases, an essential amino acid residue is a residue that, when altered from the wild-type sequence of the polypeptide, results in abolishing or substantially abolishing the polypeptide's essential biological or biochemical activity.

In some embodiments, a modified multispanning membrane polypeptide described herein comprises a conservative amino acid substitution. In some cases, a conservative amino acid substitution is one in which the amino acid residue is replaced with an amino acid residue having a similar side chain. Families of amino acid residues having similar side chains have been defined in the art. These families include, for example, amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a polypeptide, for example, is replaced with another amino acid residue from the same side chain family. Other examples of acceptable substitutions include substitutions based on isosteric considerations (e.g., norleucine for methionine) or other properties (e.g., 2-thienylalanine for phenylalanine, or 6-Cl-tryptophan for tryptophan).

Selection Markers

In some embodiments, a selection marker gene comprises antibiotic resistance gene or an auxotrophic gene. In some instances, a selection marker gene does not encode a reporter protein (e.g., a fluorescent protein). As discussed above, a selection marker in some instances facilitates stable and correct folding of a modified multispanning membrane polypeptide described herein. In some instances, a stable and correct folding of a modified multispanning membrane polypeptide refers to a polypeptide in which its structural architecture after post translational processing enables the polypeptide to achieve its biological function. In some instances, a stable and correct folding of a modified multispanning membrane polypeptide further refers to a polypeptide with a biologically active function. In some instances, a stable and correct folding of a modified multi spanning membrane polypeptide does not refers to a polypeptide with a misfolded structural architecture or a polypeptide with a structural architecture that prevents the polypeptide to undergo its biological function or activity.

In some instances, a selection marker gene comprises ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, alkaline phosphatase gene, gene encoding green fluorescent protein, gene encoding red fluorescent protein, gene encoding tdTomato fluorescent protein, or gene encoding luciferase. In some instances, a selection marker gene encodes ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene. In some instances, a selection marker gene is a first selection marker gene or a second selection marker gene. In some instances, the first selection maker gene and/or the second selection marker gene does not comprise a reporter gene.

In some instances, a selection marker gene is a first selection marker gene. In some embodiments, a first selection marker gene comprises antibiotic resistance gene or an auxotrophic gene. In some instances, a first selection marker gene does not encode a reporter protein (e.g., a fluorescent protein). In some instances, a first selection marker gene encodes ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some instances, a selection marker gene is a second selection marker gene. In some embodiments, a second selection marker gene comprises an antibiotic resistance gene or an auxotrophic gene. In some instances, a second selection marker gene does not encode a reporter protein (e.g., a fluorescent protein). In some instances, a second selection marker gene comprises an ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some instances, the first selection marker gene and second selection marker gene are the same. In other instances, the first selection marker gene and the second selection marker gene are different.

In some embodiments, the first selection marker gene and/or the second selection marker gene are operably linked directly to a polynucleotide encoding a modified multispanning membrane polypeptide or indirectly through a linker gene which encodes about 1 to about 60 amino acid residues. In some instances, the first selection marker gene is operably linked directly to a polynucleotide encoding a modified multispanning membrane polypeptide or indirectly through a linker gene which encodes about 1 to about 60 amino acid residues. In some instances, the second selection marker gene is operably linked directly to a polynucleotide encoding a modified multispanning membrane polypeptide or indirectly through a linker gene which encodes about 1 to about 60 amino acid residues. In some cases, the linker gene encodes about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

In some embodiments, the first and second selection markers are selective against a selection agent. In some embodiments, the selection agent comprises an antibiotic or a toxic metabolite. In some embodiments, the antibiotic comprises ampicillin, carbenicillin, gentamicin, chloramphenicol, neomycin, kanamycin, streptomycin, or tetracycline. In some embodiments, the toxic metabolite comprises 5-fluoroorotic acid or 3-amino-1,2,4-triazole. In some embodiments, the selection agent comprises elevated temperature, reduced temperature, a lack of nutrient, or a lack of co-factor. In some embodiments, the second selection agent comprises elevated temperature, reduced temperature, a lack of nutrient, or a lack of co-factor.

In some embodiments, the selective agent comprises a first selective agent and a second selective agent. In some embodiments, the first selection agent comprises an antibiotic or a toxic metabolite. In some embodiments, the second selection agent comprises an antibiotic or a toxic metabolite. In some embodiments, the antibiotic comprises ampicillin, carbenicillin, gentamicin, chloramphenicol, neomycin, kanamycin, streptomycin, or tetracycline. In some embodiments, the toxic metabolite comprises 5-fluoroorotic acid or 3-amino-1,2,4-triazole.

In some embodiments, the first selection agent comprises elevated temperature, reduced temperature, a lack of nutrient, or a lack of co-factor. In some embodiments, the second selection agent comprises elevated temperature, reduced temperature, a lack of nutrient, or a lack of co-factor.

Modified Membrane-Spanning Polypeptide of Formulas I-IV

In some embodiments, disclosed herein comprises generating a modified multispanning membrane polypeptide of Formula (I):

$$SP2_x\text{-}L2_m\text{-}MSMP_y\text{-}L1_n\text{-}SP1_z \quad \text{Formula I}$$

wherein:
MSMP is a multispanning membrane polypeptide comprising at least one modification;
SP1 is a first selection polypeptide linked to the C-terminus of MSMP, wherein SP1 is resistant against a first selection agent;
SP2 is a second selection polypeptide linked to the N-terminus of MSMP, wherein SP2 is resistant against a second selection agent;
L1 is a first linker;
L2 is a second linker;
x is independently 0-3;
y is independently 1-5;
z is independently 1-3; and
m and n are each independently 0-60 amino acid residues.

In some embodiments, the modified multispanning membrane polypeptide comprises a plasma membrane protein, a nuclear membrane protein, a peripheral membrane protein, an intracellular-membrane protein, a transporter, a channel protein (e.g., an ion channel protein), an adhesin, a translocase, or a receptor. In some embodiments, the modified multispanning membrane polypeptide is a modified ion channel protein. In some embodiments, the modified ion channel protein is a modified TRPV3, KCa3.1, or TRPC6. In some embodiments, the modified multispanning membrane polypeptide is a modified G protein coupled receptor (GPCR). In some embodiments, the modified GPCR is a modified CCR7, CCR10, GPR55, NTR1, EP2, or EP4 receptor. In some embodiments, the modified GPCR comprises about 1, 2, 3, 4, 5, 6, 7, 8, 9, 10, 15, 20, 25, 30, 35, 40, 45, 50, or more modified amino acid residues. In some embodiments, the modified GPCR comprises about 0.5%, 1%, 2%, 3%, 4%, 5%, 6%, 7%, 8%, 9%, 10%, 11%, 12%, 13%, 14%, 15%, 20%, 25%, 30%, or more modifications.

In some embodiments, the at least one modification is generated through a random mutagenesis method. In some instances, the random mutagenesis method comprises an error-prone PCR method. In some instances, the random mutagenesis method comprises a DNA shuffling method.

In some embodiments, the at least one modification comprises an insertion, a deletion, or a mutation. In some embodiments, the mutation comprises a nonsense mutation or a missense mutation. In some embodiments, the at least one modification comprises an N-terminal truncation, a C-terminal truncation, or a combination thereof.

In some embodiments, the modified GPCR is a mammalian GPCR. In some embodiments, the modified GPCR is a human GPCR.

In some embodiments, the first selection polypeptide is encoded by an antibiotic resistance gene or an auxotrophic gene. In some embodiments, the first selection polypeptide is not a reporter protein. In some embodiments, the first selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some embodiments, the second selection polypeptide is encoded by an antibiotic resistance gene or an auxotrophic gene. In some embodiments, the second selection polypeptide is not a reporter protein. In some embodiments, the second selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some instances, SP1, when expressed in a host cell, is located in an intracellular portion or an extracellular portion of the host cell. In some instances, SP1, when expressed in a host cell, is located in an intracellular portion of the host cell. In some cases, SP2 when expressed in a host cell is located in an intracellular portion or an extracellular portion of the host cell. In some cases, SP2, when expressed in a host cell, is located in an extracellular portion of the host cell. In some cases, SP1, when expressed in a host cell, is located in an intracellular portion of the host cell and SP2, when expressed in a host cell, is located in an extracellular portion of the host cell.

In some instances, SP1 and SP2 are the same. In other instances, SP1 and SP2 are different. In some cases, SP1 and SP2 are further linked to MSMP through L1 and L2 respectively. In some instances, L1 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length. In some cases, L2 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length.

In some embodiments, $SP1_z$ is $SP1_{2-3}$ and each of the SP1 is different from the other. In some instances, $SP1_z$ is $SP1_3$ and two out of the three SP1 are the same. In some instances, each of the SP1 is further linked to another SP1 directly or indirectly through a linker polypeptide. In some instances, the linker polypeptide comprises about 1 to about 60 amino acid residues, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

In some embodiments, $SP2_X$ is $SP2_{2-3}$ and each of the SP2 is different from the other. In some instances, $SP2_X$ is $SP2_3$ and two out of the three SP2 are the same. In some instances, each of the SP2 is further linked to another SP2 directly or indirectly through a linker polypeptide. In some instances, the linker polypeptide comprises about 1 to about 60 amino acid residues, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

In some embodiments, the first selection agent comprises an antibiotic or a toxic metabolite. In some embodiments, the second selection agent comprises an antibiotic or a toxic metabolite. In some embodiments, the antibiotic comprises ampicillin, carbenicillin, gentamicin, chloramphenicol, neomycin, kanamycin, streptomycin, or tetracycline. In some embodiments, the toxic metabolite comprises 5-fluoroorotic acid or 3-amino-1,2,4-triazole.

In some embodiments, the first selection agent comprises elevated temperature, reduced temperature, a lack of nutrient, or a lack of co-factor. In some embodiments, the second selection agent comprises elevated temperature, reduced temperature, a lack of nutrient, or a lack of co-factor.

In some embodiments, the modified multispanning membrane polypeptide further comprises a tag. In some embodiments, the tag is linked to the N-terminus of the modified multispanning membrane polypeptide, the C-terminus of the modified multispanning membrane polypeptide, or a combination thereof. In some embodiments, the tag comprises MBP, TrxA, FLAG-tag, AVI-tag, or HisTag.

In some embodiments, disclosed herein comprises generating a modified multispanning membrane polypeptide of Formula (Ia):

SP2-L2$_m$-MSMP-L1$_n$-SP1    Formula Ia wherein:
MSMP is a multispanning membrane polypeptide comprising at least one modification;
SP1 is a first selection polypeptide linked to the C-terminus of MSMP, wherein SP1 is resistant against a first selection agent;
SP2 is a second selection polypeptide linked to the N-terminus of MSMP, wherein SP2 is resistant against a second selection agent;
L1 is a first linker;
L2 is a second linker; and
m and n are each independently 0-60 amino acid residues.

In some embodiments, the modified multispanning membrane polypeptide comprises a plasma membrane protein, a nuclear membrane protein, a peripheral membrane protein, an intracellular-membrane protein, a transporter, a channel protein (e.g., an ion channel protein), an adhesin, a translocase, or a receptor. In some embodiments, the modified multispanning membrane polypeptide is a modified ion channel protein. In some embodiments, the modified ion channel protein is a modified TRPV3, KCa3.1, or TRPC6. In some embodiments, the modified multispanning membrane polypeptide is a modified G protein coupled receptor (GPCR). In some embodiments, the modified GPCR is a modified CCR7, CCR10, GPR55, NTR1, EP2, or EP4 receptor. In some embodiments, the modified GPCR comprises about 1, 2, 3, 4, 5, 6, 7, 8, 9, 10, 15, 20, 25, 30, 35, 40, 45, 50, or more modified amino acid residues. In some embodiments, the modified GPCR comprises about 0.5%, 1%, 2%, 3%, 4%, 5%, 6%, 7%, 8%, 9%, 10%, 11%, 12%, 13%, 14%, 15%, 20%, 25%, 30%, or more modifications.

In some embodiments, the at least one modification is generated through a random mutagenesis method. In some instances, the random mutagenesis method comprises an error-prone PCR method. In some instances, the random mutagenesis method comprises a DNA shuffling method.

In some embodiments, the at least one modification comprises an insertion, a deletion, or a mutation. In some embodiments, the mutation comprises a nonsense mutation or a missense mutation. In some embodiments, the at least one modification comprises an N-terminal truncation, a C-terminal truncation, or a combination thereof.

In some embodiments, the modified GPCR is a mammalian GPCR. In some embodiments, the modified GPCR is a human GPCR.

In some embodiments, the first selection polypeptide is encoded by an antibiotic resistance gene or an auxotrophic gene. In some embodiments, the first selection polypeptide is not a reporter protein. In some embodiments, the first selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some embodiments, the second selection polypeptide is encoded by an antibiotic resistance gene or an auxotrophic gene. In some embodiments, the second selection polypeptide is not a reporter protein. In some embodiments, the second selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some instances, SP1, when expressed in a host cell, is located in an intracellular portion or an extracellular portion of the host cell. In some instances, SP1, when expressed in a host cell, is located in an intracellular portion of the host cell. In some cases, SP2, when expressed in a host cell, is located in an intracellular portion or an extracellular portion of the host cell. In some cases, SP2, when expressed in a host cell, is located in an extracellular portion of the host cell. In some cases, SP1, when expressed in a host cell, is located in an intracellular portion of the host cell and SP2, when expressed in a host cell, is located in an extracellular portion of the host cell.

In some instances, SP1 and SP2 are the same. In other instances, SP1 and SP2 are different. In some cases, SP1 and SP2 are further linked to MSMP through L1 and L2 respectively. In some instances, L1 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length. In some cases, L2 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length.

In some embodiments, the first selection agent comprises an antibiotic or a toxic metabolite. In some embodiments, the second selection agent comprises an antibiotic or a toxic metabolite. In some embodiments, the antibiotic comprises ampicillin, carbenicillin, gentamicin, chloramphenicol, neomycin, kanamycin, streptomycin, or tetracycline. In some embodiments, the toxic metabolite comprises 5-fluoroorotic acid or 3-amino-1,2,4-triazole.

In some embodiments, the first selection agent comprises elevated temperature, reduced temperature, a lack of nutrient, or a lack of co-factor. In some embodiments, the second selection agent comprises elevated temperature, reduced temperature, a lack of nutrient, or a lack of co-factor.

In some embodiments, the modified multispanning membrane polypeptide further comprises a tag. In some embodiments, the tag is linked to the N-terminus of the modified multispanning membrane polypeptide, the C-terminus of the modified multispanning membrane polypeptide, or a combination thereof. In some embodiments, the tag comprises MBP, TrxA, FLAG-tag, AVI-tag, or HisTag.

In some embodiments, disclosed herein comprises generating a modified multispanning membrane polypeptide of Formula (II):

$$SP2_x\text{-}L2_m\text{-}RP_y\text{-}L1_n\text{-}SP1_z \qquad \text{Formula II}$$

wherein:
RP is a receptor polypeptide selected from an ion channel polypeptide or a GPCR, wherein RP comprises at least one modification;
SP1 is a first selection polypeptide linked to the C-terminus of RP, wherein SP1 is resistant against a first selection agent;
SP2 is a second selection polypeptide linked to the N-terminus of RP, wherein SP2 is resistant against a second selection agent;
L1 is a first linker;
L2 is a second linker;
x is independently 0-3;
y is independently 1-5;
z is independently 1-3; and
m and n are each independently 0-60 amino acid residues.

In some embodiments, RP is a modified ion channel polypeptide. In some instances, the modified ion channel polypeptide is a voltage-gated ion channel polypeptide or a transient receptor potential channel polypeptide. In some embodiments, the modified ion channel polypeptide is a modified TRPV3, KCa3.1, or TRPC6. In some embodiments, RP is a modified G protein coupled receptor (GPCR). In some embodiments, the modified GPCR is a modified CCR7, CCR10, GPR55, NTR1, EP2, or EP4 receptor. In some embodiments, the modified GPCR comprises about 1, 2, 3, 4, 5, 6, 7, 8, 9, 10, 15, 20, 25, 30, 35, 40, 45, 50, or more modified amino acid residues. In some embodiments, the modified GPCR comprises about 0.5%, 1%, 2%, 3%, 4%, 5%, 6%, 7%, 8%, 9%, 10%, 11%, 12%, 13%, 14%, 15%, 20%, 25%, 30%, or more modifications.

In some embodiments, the at least one modification is generated through a random mutagenesis method. In some instances, the random mutagenesis method comprises an error-prone PCR method. In some instances, the random mutagenesis method comprises a DNA shuffling method.

In some embodiments, the at least one modification comprises an insertion, a deletion, or a mutation. In some embodiments, the mutation comprises a nonsense mutation or a missense mutation. In some embodiments, the at least one modification comprises an N-terminal truncation, a C-terminal truncation, or a combination thereof.

In some embodiments, the modified GPCR is a mammalian GPCR. In some embodiments, the modified GPCR is a human GPCR.

In some embodiments, the first selection polypeptide is encoded by an antibiotic resistance gene or an auxotrophic gene. In some embodiments, the first selection polypeptide is not a reporter protein. In some embodiments, the first selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some embodiments, the second selection polypeptide is encoded by an antibiotic resistance gene or an auxotrophic gene. In some embodiments, the second selection polypeptide is not a reporter protein. In some embodiments, the second selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some instances, SP1, when expressed in a host cell, is located in an intracellular portion or an extracellular portion of the host cell. In some instances, SP1, when expressed in a host cell, is located in an intracellular portion of the host cell. In some cases, SP2, when expressed in a host cell, is located in an intracellular portion or an extracellular portion of the host cell. In some cases, SP2, when expressed in a host cell, is located in an extracellular portion of the host cell. In some cases, SP1, when expressed in a host cell, is located in an intracellular portion of the host cell and SP2, when expressed in a host cell, is located in an extracellular portion of the host cell.

In some instances, SP1 and SP2 are the same. In other instances, SP1 and SP2 are different. In some cases, SP1 and SP2 are further linked to RP through L1 and L2 respectively. In some instances, L1 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length. In some cases, L2 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length.

In some embodiments, $SP1_z$ is $SP1_{2-3}$ and each SP1 is different from the other. In some instances, $SP1_z$ is $SP1_3$ and two out of the three SP1 are the same. In some instances, each SP1 is further linked to another SP1 directly or indirectly through a linker polypeptide. In some instances, the linker polypeptide comprises about 1 to about 60 amino acid residues, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

In some embodiments, $SP2_X$ is $SP2_{2-3}$ and each SP2 is different from the other. In some instances, $SP2_x$ is $SP2_3$ and two out of the three SP2 are the same. In some instances, each SP2 is further linked to another SP2 directly or indirectly through a linker polypeptide. In some instances, the linker polypeptide comprises about 1 to about 60 amino acid residues, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

In some embodiments, the first selection agent comprises an antibiotic or a toxic metabolite. In some embodiments, the second selection agent comprises an antibiotic or a toxic metabolite. In some embodiments, the antibiotic comprises ampicillin, carbenicillin, gentamicin, chloramphenicol, neomycin, kanamycin, streptomycin, or tetracycline. In some embodiments, the toxic metabolite comprises 5-fluoroorotic acid or 3-amino-1,2,4-triazole.

In some embodiments, the first selection agent comprises elevated temperature, reduced temperature, a lack of nutrient, or a lack of co-factor. In some embodiments, the second selection agent comprises elevated temperature, reduced temperature, a lack of nutrient, or a lack of co-factor.

In some embodiments, the modified multispanning membrane polypeptide of Formula (II) further comprises a tag. In some embodiments, the tag is linked to the N-terminus of the modified multispanning membrane polypeptide, the C-terminus of the modified multispanning membrane polypeptide, or a combination thereof. In some embodiments, the tag comprises MBP, TrxA, FLAG-tag, AVI-tag, or HisTag.

In some embodiments, disclosed herein comprises generating a modified multispanning membrane polypeptide of Formula (III):

                              Formula III wherein:
GPCR is a GPCR comprising at least one modification;
SP1 is a first selection polypeptide linked to the C-terminus of GPCR, wherein SP1, when expressed in a host cell, is located in the intracellular portion of the host cell and is resistant against a first selection agent;
SP2 is a second selection polypeptide linked to the N-terminus of GPCR, wherein SP2, when expressed in a host cell, is located in the extracellular portion of the host cell and is resistant against a second selection agent;
L1 is a first linker;
L2 is a second linker;
x is independently 0-3;
y is independently 1-5;
z is independently 1-3; and
m and n are each independently 0-60 amino acid residues.

In some embodiments, the modified GPCR is a modified CCR7, CCR10, GPR55, NTR1, EP2, or EP4 receptor. In some embodiments, the modified GPCR comprises about 1, 2, 3, 4, 5, 6, 7, 8, 9, 10, 15, 20, 25, 30, 35, 40, 45, 50, or more modified amino acid residues. In some embodiments, the modified GPCR comprises about 0.5%, 1%, 2%, 3%, 4%, 5%, 6%, 7%, 8%, 9%, 10%, 11%, 12%, 13%, 14%, 15%, 20%, 25%, 30%, or more modifications.

In some embodiments, the at least one modification is generated through a random mutagenesis method. In some instances, the random mutagenesis method comprises an error-prone PCR method. In some instances, the random mutagenesis method comprises a DNA shuffling method.

In some embodiments, the at least one modification comprises an insertion, a deletion, or a mutation. In some embodiments, the mutation comprises a nonsense mutation or a missense mutation. In some embodiments, the at least one modification comprises an N-terminal truncation, a C-terminal truncation, or a combination thereof.

In some embodiments, the modified GPCR is a mammalian GPCR. In some embodiments, the modified GPCR is a human GPCR.

In some embodiments, the first selection polypeptide is encoded by an antibiotic resistance gene or an auxotrophic gene. In some embodiments, the first selection polypeptide is not a reporter protein. In some embodiments, the first selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some embodiments, the second selection polypeptide is encoded by an antibiotic resistance gene or an auxotrophic gene. In some embodiments, the second selection polypeptide is not a reporter protein. In some embodiments, the second selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some instances, SP1 and SP2 are the same. In other instances, SP1 and SP2 are different. In some cases, SP1 and SP2 are further linked to GPCR through L1 and L2 respectively. In some instances, L1 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length. In some cases, L2 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length.

In some embodiments, $SP1_z$ is $SP1_{2-3}$ and each of the SP1 is different from the other. In some instances, $SP1_z$ is $SP1_3$ and two out of the three SP1 are the same. In some instances, each of the SP1 is further linked to another SP1 directly or indirectly through a linker polypeptide. In some instances, the linker polypeptide comprises about 1 to about 60 amino acid residues, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

In some embodiments, $SP2_X$ is $SP2_{2-3}$ and each of the SP2 is different from the other. In some instances, $SP2_X$ is $SP2_3$ and two out of the three SP2 are the same. In some instances, each of the SP2 is further linked to another SP2 directly or indirectly through a linker polypeptide. In some instances, the linker polypeptide comprises about 1 to about 60 amino acid residues, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

In some embodiments, the first selection agent comprises an antibiotic or a toxic metabolite. In some embodiments, the second selection agent comprises an antibiotic or a toxic metabolite. In some embodiments, the antibiotic comprises ampicillin, carbenicillin, gentamicin, chloramphenicol, neomycin, kanamycin, streptomycin, or tetracycline. In some embodiments, the toxic metabolite comprises 5-fluoroorotic acid or 3-amino-1,2,4-triazole.

In some embodiments, the first selection agent comprises elevated temperature, reduced temperature, a lack of nutrient, or a lack of co-factor. In some embodiments, the second selection agent comprises elevated temperature, reduced temperature, a lack of nutrient, or a lack of co-factor.

In some embodiments, the modified multispanning membrane polypeptide of Formula (III) further comprises a tag. In some embodiments, the tag is linked to the N-terminus of the modified multispanning membrane polypeptide, the C-terminus of the modified multispanning membrane polypeptide, or a combination thereof. In some embodiments, the tag comprises MBP, TrxA, FLAG-tag, AVI-tag, or HisTag.

In some embodiments, disclosed herein comprises generating a modified multispanning membrane polypeptide of Formula (IV):

$$SP2_x\text{-}L2_m\text{-}ICP_y\text{-}L1_n\text{-}SP1_z \qquad \text{Formula IV}$$

wherein:
ICP is an ion channel polypeptide comprising at least one modification;
SP1 is a first selection polypeptide linked to the C-terminus of ICP, wherein SP1 is resistant against a first selection agent;
SP2 is a second selection polypeptide linked to the N-terminus of ICP, wherein SP2 is resistant against a second selection agent;
L1 is a first linker;
L2 is a second linker;
x is independently 0-3;
y is independently 1-5;
z is independently 1-3; and
m and n are each independently 0-60 amino acid residues.

In some embodiments, the modified ion channel protein is a modified TRPV3, KCa3.1, or TRPC6. In some embodiments, the modified ion channel protein comprises about 1, 2, 3, 4, 5, 6, 7, 8, 9, 10, 15, 20, 25, 30, 35, 40, 45, 50, or more modified amino acid residues. In some embodiments, the modified ion channel protein comprises about 0.5%, 1%, 2%, 3%, 4%, 5%, 6%, 7%, 8%, 9%, 10%, 11%, 12%, 13%, 14%, 15%, 20%, 25%, 30%, or more modifications.

In some embodiments, the at least one modification is generated through a random mutagenesis method. In some instances, the random mutagenesis method comprises an error-prone PCR method. In some instances, the random mutagenesis method comprises a DNA shuffling method.

In some embodiments, the at least one modification comprises an insertion, a deletion, or a mutation. In some embodiments, the mutation comprises a nonsense mutation or a missense mutation. In some embodiments, the at least one modification comprises an N-terminal truncation, a C-terminal truncation, or a combination thereof.

In some embodiments, the modified ion channel protein is a mammalian ion channel protein. In some embodiments, the modified ion channel protein is a human ion channel protein.

In some embodiments, the first selection polypeptide is encoded by an antibiotic resistance gene or an auxotrophic gene. In some embodiments, the first selection polypeptide is not a reporter protein. In some embodiments, the first selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some embodiments, the second selection polypeptide is encoded by an antibiotic resistance gene or an auxotrophic gene. In some embodiments, the second selection polypeptide is not a reporter protein. In some embodiments, the second selection polypeptide is a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

In some instances, SP1, when expressed in a host cell, is located in an intracellular portion or an extracellular portion of the host cell. In some instances, SP1, when expressed in a host cell, is located in an intracellular portion of the host cell. In some cases, SP2, when expressed in a host cell, is located in an intracellular portion or an extracellular portion of the host cell. In some cases, SP2, when expressed in a host cell, is located in an extracellular portion of the host cell. In some cases, SP1, when expressed in a host cell, is located in an intracellular portion of the host cell and SP2, when expressed in a host cell, is located in an extracellular portion of the host cell.

In some instances, SP1 and SP2 are the same. In other instances, SP1 and SP2 are different. In some cases, SP1 and SP2 are further linked to ICP through L1 and L2 respectively. In some instances, L1 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length. In some cases, L2 is about 0 to about 60 amino acid residues in length, e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues in length.

In some embodiments, $SP1_z$ is $SP1_{2-3}$ and each SP1 is different from the other. In some instances, $SP1_z$ is $SP1_3$ and two out of the three SP1 are the same. In some instances, each SP1 is further linked to another SP1 directly or indirectly through a linker polypeptide. In some instances, the linker polypeptide comprises about 1 to about 60 amino acid residues, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

In some embodiments, $SP2_X$ is $SP2_{2-3}$ and each SP2 is different from the other. In some instances, $SP2_x$ is $SP2_3$ and two out of the three SP2 are the same. In some instances, each SP2 is further linked to another SP2 directly or indirectly through a linker polypeptide. In some instances, the linker polypeptide comprises about 1 to about 60 amino acid residues, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

In some embodiments, the first selection agent comprises an antibiotic or a toxic metabolite. In some embodiments, the second selection agent comprises an antibiotic or a toxic metabolite. In some embodiments, the antibiotic comprises ampicillin, carbenicillin, gentamicin, chloramphenicol, neomycin, kanamycin, streptomycin, or tetracycline. In some embodiments, the toxic metabolite comprises 5-fluoroorotic acid or 3-amino-1,2,4-triazole.

In some embodiments, the first selection agent comprises elevated temperature, reduced temperature, a lack of nutrient, or a lack of co-factor. In some embodiments, the second selection agent comprises elevated temperature, reduced temperature, a lack of nutrient, or a lack of co-factor.

In some embodiments, the modified multispanning membrane polypeptide of Formula (IV) further comprises a tag. In some embodiments, the tag is linked to the N-terminus of the modified multispanning membrane polypeptide, the C-terminus of the modified multispanning membrane polypeptide, or a combination thereof. In some embodiments, the tag comprises MBP, TrxA, FLAG-tag, AVI-tag, or HisTag.

Random Mutagenesis

In some embodiments, a modified multispanning membrane polypeptide is generated by a random mutagenesis method. In some instances, random mutagenesis is a method of generating a library of protein mutants with different functional properties. For example, random mutations are first introduced into a gene to generate a library containing billions of different versions of this gene. Versions or variants of this gene are then expressed and followed by evaluating the property of each expressed protein for function. In some cases, random mutagenesis is achieved using error-prone PCR, rolling circle error-prone PCR, mutator strains, temporary mutator strains, insertion mutagenesis, ethyl methanesulfonate, nitrous acid, or DNA shuffling. In some cases, random mutagenesis is generated using, e.g., UV, ionizing radiation, X-ray, gamma rays, or by chemical agents, such as for example, mustard gas, cyclophosphamide, or cisplatin.

In some instances, random mutagenesis is achieved using an error-prone PCR method. In some cases, an error-prone PCR is a PCR method with a low fidelity polymerase (e.g., a polymerase with a high error rate). In some cases, such PCR method results in up to 2% of errors during amplification of a wild-type sequence with point mutations or single nucleotide mutations as the most common type of mutations. In some embodiments, a modified multispanning membrane polypeptide described herein is generated by an error-prone PCR method.

In some instances, random mutagenesis is achieved using a rolling circle error-prone PCR method. In a rolling circle error-prone PCR, for example, a wild-type sequence is first cloned into a plasmid, and then the whole plasmid is amplified under error-prone PCR condition. In some embodiments, a modified multispanning membrane polypeptide described herein is generated by a rolling circle error-prone PCR method.

In some instances, random mutagenesis is achieved using a mutator strain approach. In some cases, a mutator strain approach utilizes a mutator strain such as XL1-Red (Strategene) which is an *E. coli* strain deficient in three DNA repair pathways (mutS, mutD, and mutT) and therefore induces errors during replication. In some embodiments, a modified multispanning membrane polypeptide described herein is generated by a mutator strain approach.

In some instances, random mutagenesis is achieved using a temporary mutator strain method. In some cases, a temporary mutator strain method is deficient in one DNA repair pathway (mutD5) instead of three DNA repair pathways. In some embodiments, a modified multispanning membrane polypeptide described herein is generated by a temporary mutator strain method.

In some instances, random mutagenesis is achieved using an insertion mutagenesis. In some cases, an insertion mutagenesis utilizes a transposon-based system to randomly insert a 15-base sequence throughout a sequence of interest. In some embodiments, a modified multispanning membrane polypeptide described herein is generated by an insertion mutagenesis.

In some instances, random mutagenesis is achieved using an ethyl methanesulfonate (EMS) approach. In some cases an ethyl methanesulfonate (EMS) approach utilizes the chemical EMS to alkylate guanidine residues, thereby causing them to be incorrectly copied during DNA replication. In some embodiments, a modified multispanning membrane polypeptide described herein is generated by an ethyl methanesulfonate approach.

In some instances, random mutagenesis is achieved using nitrous acid. In some cases, nitrous acid is a chemical mutagen that introduces mutations by de-aminating adenine and cytosine residues, thereby causing transversion point mutations. In some embodiments, a modified multispanning membrane polypeptide described herein is generated by nitrous acid.

In some instances, random mutagenesis is achieved using DNA shuffling. DNA shuffling, in some cases, is achieved through randomly digesting the sequence of interest or a sequence library with DNAseI and then randomly re-joining the fragments using self-priming PCR. In some embodiments, a modified multispanning membrane polypeptide described herein is generated by a DNA shuffling method.

Non-Random Mutagenesis

In some embodiments, a modified multispanning membrane polypeptide is generated by a non-random mutagenesis method. Exemplary non-random mutagenesis method includes a site-directed mutagenesis. Site-directed mutagenesis is a method that allows specific alterations or modifications within the gene of interest. In some instances, a site-directed mutagenesis utilizes cassette mutagenesis, PCR-site-directed mutagenesis, whole plasmid mutagenesis, Kunkel's method, or in vivo site-directed mutagenesis method. A cassette mutagenesis, for example, allows for synthesized fragments of DNA to be inserted into a plasmid using a restriction enzyme and ligation method. In some cases, it does not involve polymerization. In some instances, a PCR site-directed mutagenesis is similar to a cassette mutagenesis, but in which larger fragments are obtained, separated by gel electrophoresis from the template fragments, and then ligated into the gene of interest. Whole plasmid mutagenesis, such as the Quikchange® method, allows for mutations to be inserted using one or more primers and then amplifies the entire plasmid. In some instances, this method differs from the PCR site-directed mutagenesis in that the plasmid is in a linear format and that it does not need to be exponentially amplified as in a PCR. Kunkel's method, for example, is a primer based site directed method, and differs from previous methods in that it utilizes an *E. coli* strain that is deficient in dUTPase, an enzyme that prevents the bacteria from incorporating uracil during DNA replication, to distinguish between product and template strains thereby allowing for easier selection of plasmids containing the desired mutation. In some cases, an in vivo site-directed mutagenesis method includes the Dehtto perfetto method, transplacement "pop-in pop-out" method, direct gene deletion and site-specific mutagenesis with PCR and one recyclable marker, direct gene deletion and site-specific mutagenesis with PCR and one recyclable marker using long homologous regions, or in vivo site-directed mutagenesis with synthetic oligonucleotides.

Expression Vectors

In some embodiments, vectors include any suitable vectors derived from either eukaryotic or prokaryotic sources. In some cases, vectors are obtained from bacteria (e.g. *E. coli*), insects, yeast (e.g. *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichi pastoris* vector, pGAPZA,B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors. Mammalian transient expression vectors include, e.g., p3×FLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3×FLAG-CMV 7.1, pFLAG-CMV 20, p3×FLAG-Myc-CMV 24, pCMV-FLAG-MAT1, pCMV-FLAG-MAT2, pBICEP-CMV 3, or pBICEP-CMV 4. Mammalian stable expression vector include, e.g., pFLAG-CMV 3, p3×FLAG-CMV 9, p3×FLAG-CMV 13, pFLAG-Myc-CMV 21, p3×FLAG-Myc-CMV 25, pFLAG-CMV 4, p3×FLAG-CMV 10, p3×FLAG-CMV 14, pFLAG-Myc-CMV 22, p3×FLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or HeLa cells. Exemplary cell-free systems include, but are not limited to, *E. coli* S30 Extract system, *E. coli* T7 S30 system, or PURExpress®.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., yeast cells), animal cell or plant cell. In some cases, a prokaryotic cell is a bacterial cell. Examples of bacterial cells include gram-positive bacteria or gram-negative bacteria. Sometimes the gram-negative bacteria is anaerobic, rod-shaped, or both.

In some instances, gram-positive bacteria include *Actinobacteria*, *Firmicutes* or *Tenericutes*. In some cases, gram-negative bacteria include *Aquificae*, *Deinococcus-Thermus*, *Fibrobacteres-Chlorobi/Bacteroidetes* (FCB group), *Fusobacteria*, *Gemmatimonadetes*, *Nitrospirae*, *Planctomycetes-Verrucomicrobia/Chlamydiae* (PVC group), *Proteobacteria*, *Spirochaetes* or *Synergistetes*. Other bacteria include, for example, *Acidobacteria*, *Chloroflexi*, *Chrysiogenetes*, *Cyanobacteria*, *Deferribacteres*, *Dictyoglomi*, *Thermodesulfobacteria*or *Thermotogae*. A bacterial cell is, for example, *Escherichia coli*, *Clostridium botulinum*, or *Coli bacilli*.

Exemplary prokaryotic host cells include, but are not limited to, BL21, Mach1™, DH10B™, TOP10, DH5α, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™.

In some instances, animal cells include a cell from a vertebrate or from an invertebrate. In some cases, an animal cell includes a cell from a marine invertebrate, fish, insects, amphibian, reptile, or mammal. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes *Ascomycota* or *Basidiomycota*. In some cases, *Ascomycota* includes *Saccharomycotina* (true yeasts, e.g. *Saccharomyces cerevisiae* (baker's yeast)) or *Taphrinomycotina* (e.g. *Schizosaccharomycetes* (fission yeasts)). In some cases, *Basidiomycota* includes *Agaricomycotina* (e.g. *Tremellomycetes*) or *Pucciniomycotina* (e.g. *Microbotryomycetes*).

Exemplary yeast or filamentous fungi include, for example, the genus: *Saccharomyces*, *Schizosaccharomyces*, *Candida*, *Pichia*, *Hansenula*, *Kluyveromyces*, *Zygosaccharomyces*, *Yarrowia*, *Trichosporon*, *Rhodosporidi*, *Aspergillus*, *Fusarium*, or *Trichoderma*. Exemplary yeast or filamentous fungi include, for example, the species: *Saccharomyces cerevisiae*, *Schizosaccharomyces pombe*, *Candida utilis*, *Candida boidini*, *Candida albicans*, *Candida tropicalis*, *Candida stellatoidea*, *Candida glabrata*, *Candida krusei*, *Candida parapsilosis*, *Candida guilliermondii*, *Candida viswanathii*, *Candida lusitaniae*, *Rhodotorula mucilaginosa*, *Pichia metanolica*, *Pichia angusta*, *Pichia pastoris*, *Pichia anomala*, *Hansenula polymorpha*, *Kluyveromyces lactis*, *Zygosaccharomyces rouxii*, *Yarrowia lipolytica*, *Trichosporon pullulans*, *Rhodosporidium toru-Aspergillus niger*, *Aspergillus nidulans*, *Aspergillus awamori*, *Aspergillus oryzae*, *Trichoderma reesei*, *Yarrowia lipolytica*, *Brettanomyces bruxellensis*, *Candida stellata*, *Schizosaccharomyces pombe*, *Torulaspora delbrueckii*, *Zygosaccharomyces bailii*, *Cryptococcus neoformans*, *Cryptococcus gattii*, or *Saccharomyces boulardii*.

Exemplary yeast host cells include, but are not limited to, *Pichia pastoris* yeast strains such as GS115, KM71H, SMD1168, SMD1168H, and X-33; and *Saccharomyces cerevisiae* yeast strain such as INVSc1.

In some instances, additional animal cells include cells obtained from a mollusk, arthropod, annelid or sponge. In some cases, an additional animal cell is a mammalian cell, e.g., from a primate, ape, equine, bovine, porcine, canine, feline, or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PPC 7942.

Analytical Techniques for Characterizing a Physicochemical Property

In some embodiments, one or more analytical techniques are utilized for characterizing a physicochemical property of a modified multispanning membrane polypeptide described herein. As discussed above, a physicochemical property comprises expression level, stability, conformational selectivity, homogeneity, protein crystallization, antigenicity, immunogenicity or pathway activation selectivity. In some instances, the one or more analytical technique comprises X-ray crystallography, electron crystallography, cryo electron microscopy, nuclear magnetic resonance spectroscopy (NMR), thermal denaturing techniques, or chemical denaturing techniques.

In some instances, an analytical technique used for characterizing a physicochemical property of a modified multispanning membrane polypeptide described herein is X-ray crystallography. In some instances, one or more crystallization methods are used for generating a protein crystal. For example, a vapor diffusion method is sometimes used for generating a protein crystal of a modified multispanning membrane polypeptide described herein. Other times, a lipidic cubic phase (LCP) crystallization method is used for generating a protein crystal of a modified multispanning membrane polypeptide described herein. In some instances, crystallization of a protein (e.g., a modified multispanning membrane polypeptide described herein) comprises mixing the purified protein with solutions intended to drive the protein to supersaturation, crystal nucleation, and crystal growth.

In some instances, a modified multispanning membrane polypeptide described herein is evaluated based on its protein crystallization property, e.g., its ability in forming a protein crystal, the time in forming a crystal capable of being harvested, the time in forming a crystal capable of being screened through an X-ray detector, the ability in forming a single crystal rather than multiple crystals fused together, and the diffraction resolution. In some instances, the time in forming a crystal capable of being harvested comprises 1, 2, 3, 4, 5, 6, 7, 8, 9, 10, 15, 20, 30, or more days. In some instances, the size of a crystal capable of being harvested or capable of being screened by an X-ray detector comprises a crystal with a diameter of about 5 micron, 10 micron, 15 micron, 20 micron, 30 micron, 40 micron, 50 micron, 80 micron, 100 micron, 150 micron, 200 micron, 250 micron, 300 micron, 400 micron, or more. In some instances, the diffraction resolution comprises 6 Å, 5.5 Å, 5 Å, 4.5 Å, 4 Å, 3.5 Å, 3 Å, 2.5 Å, 2 Å, or higher in resolution. In some instances, a modified multispanning membrane polypeptide described herein comprises improved or superior properties, e.g., in one or more of: its ability in forming a protein crystal, the time in forming a crystal capable of being harvested, the time in forming a crystal capable of being screened through an X-ray detector, the ability in forming a single crystal rather than multiple crystals fused together, and the diffraction resolution; relative to a wild-type multispanning membrane polypeptide or a different modified multispanning membrane polypeptide.

In some instances, a modified multispanning membrane polypeptide described herein is a modified GPCR. In some instances, a modified GPCR described herein is evaluated based on its protein crystallization property, e.g., its ability in forming a protein crystal, the time in forming a crystal capable of being harvested, the time in forming a crystal capable of being screened through an X-ray detector, the ability in forming a single crystal rather than multiple crystals fused together, and the diffraction resolution. In some instances, a modified GPCR described herein comprises improved or superior properties, e.g., in one or more of: its ability in forming a protein crystal, the time in forming a crystal capable of being harvested, the time in forming a crystal capable of being screened through an X-ray detector, the ability in forming a single crystal rather than multiple crystals fused together, and the diffraction resolution; relative to a wild-type GPCR or a different modified GPCR.

In some instances, an analytical technique used for characterizing a physicochemical property of a modified multispanning membrane polypeptide described herein is electron crystallography. In some instances, electron crystallography is a method of determining the arrangement of atoms of a target polypeptide using a transmission electron microscope (TEM). In some instances, a modified multispanning membrane polypeptide described herein is a modified GPCR. In some instances, electron crystallography (e.g., TEM) is used for characterizing a physicochemical property of a modified GPCR.

In some instances, an analytical technique used for characterizing a physicochemical property of a modified multispanning membrane polypeptide described herein is cryo electron microscopy (cryo-EM). In some instances, cryo-EM is a form of TEM in which the sample is analyzed at cryogenic temperature. In some instances, a modified multispanning membrane polypeptide described herein is a modified GPCR. In some instances, cryo electron microscopy (cryo-EM) is used for characterizing a physicochemical property of a modified GPCR.

In some instances, an analytical technique used for characterizing a physicochemical property of a modified multispanning membrane polypeptide described herein is nuclear magnetic resonance spectroscopy (NMR). In some instances, a modified multispanning membrane polypeptide described herein is a modified GPCR. In some instances, NMR is used for characterizing a physicochemical property of a modified GPCR.

In some instances, an analytical technique used for characterizing a physicochemical property of a modified multispanning membrane polypeptide described herein is a thermal denaturing technique (e.g., circular dichroism or differential scanning calorimetry). In some instances, a modified multispanning membrane polypeptide described herein is a modified GPCR. In some instances, a thermal denaturing technique (e.g., circular dichroism or differential scanning calorimetry) is used for characterizing a physicochemical property of a modified GPCR.

In some instances, an analytical technique used for characterizing a physicochemical property of a modified multispanning membrane polypeptide described herein is a chemical denaturing technique (e.g., urea, guanidine-HCl, or harsh detergents such as short-chain detergents, anionic detergents, or cationic detergents). In some instances, a modified multispanning membrane polypeptide described herein is a modified GPCR. In some instances, a chemical denaturing technique (e.g., urea, guanidine-HCl, or harsh detergents such as short-chain detergents, anionic detergents, or cationic detergents) is used for characterizing a physicochemical property of a modified GPCR.

Method of Screening a Therapeutic Agent

In some embodiments, disclosed herein are methods and platform for screening a therapeutic agent against a modified multispanning membrane polypeptide described herein. In some instances, the therapeutic agent is a polypeptide or a small molecule. In some embodiments, the therapeutic agent is a polypeptide. In other embodiments, the therapeutic agent is a small molecule.

In some instances, described herein is a method of screening a therapeutic agent against a modified multispanning membrane polypeptide, comprising a) generating a modified multispanning membrane polypeptide library by a random mutagenesis method; b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; c) expressing the first set of expression vectors in a first plurality of host cells in the presence or absence of at least one selection agent to select for a set of stably folded multispanning membrane polypeptides; d) generating a production vector comprising a second polynucleotide encoding a stably folded multispanning membrane polypeptide from the set of stably folded multispanning membrane polypeptides identified in step c); e) expressing the production vector in a second plurality of host cells, wherein the host cells are production host cells; f) incubating a multispanning membrane polypeptide product generated from the production vector of step e) with a therapeutic agent; and g) detecting a binding between the multispanning membrane polypeptide product and the therapeutic agent. In some cases, the method further comprises a) generating a second set of production vectors in which each production vector comprises a multispanning membrane polypeptide product from the set of stably folded multispanning membrane polypeptide identified in step c) above; b) expressing the second set of production vectors in a third plurality of host cells, wherein the host cells are production host cells; and c) analyzing a set of multispanning membrane polypeptide products by an analytical method to determine an expressed stably folded multispanning membrane polypeptide from the set with an enhanced or improved physicochemical property for screening against the therapeutic agent of step f) above, wherein the enhanced or improved physicochemical property is relative to a control multispanning membrane polypeptide. In some instances, the enhanced or improved physicochemical property comprises expression level, stability, conformational selectivity, homogeneity, protein crystallization, antigenicity, immunogenicity or pathway activation selectivity. In some instances, the control comprises a wild-type multispanning membrane polypeptide or a modified multispanning membrane polypeptide with a different modification. In some instances, the binding in step g) above is detected by a flow cytometry method, by enzyme-linked immunosorbent assay (ELISA), by a backscattering interferometry method, a fluorescent polarization method, a surface plasmon resonance (SPR) method, a plasmon-waveguide resonance method, a nuclear magnetic resonance (NMR) method, an isothermal titration calorimetry method, a thermal denaturation assay, a fluorescent ligand binding assay, or a radioligand binding assay. In some instances, the binding in step g) above is detected by a flow cytometry method or by enzyme-linked immunosorbent assay (ELISA). In some cases, the flow cytometry method comprises magnetic-activated cell sorting (MACS) or fluorescence-activated cell sorting (FACS).

In some instances, the modified multispanning membrane polypeptide comprises a plasma membrane protein, a nuclear membrane protein, a peripheral membrane protein, an intracellular-membrane protein, a transporter, a channel protein (e.g., an ion channel protein), an adhesin, a translocase, or a receptor. In some instances, the modified multispanning membrane polypeptide is a modified ion channel protein. In some cases, the modified ion channel protein is a modified TRPV3, KCa3.1, or TRPC6. In some instances, the modified multispanning membrane polypeptide is a modified G protein coupled receptor (GPCR). In some cases, the modified GPCR is a modified CCR7, CCR10, GPR55, NTR1, EP2, or EP4 receptor.

Methods of Screening a Polypeptide

In some embodiments, the therapeutic agent is a polypeptide. In some instances, the polypeptide is a polypeptide that interacts with a multispanning membrane polypeptide. In some cases, the multispanning membrane polypeptide comprises a plasma membrane protein, a nuclear membrane protein, a peripheral membrane protein, an intracellular-membrane protein, a transporter, a channel protein (e.g., an ion channel protein), an adhesin, a translocase, or a receptor. In some cases, the therapeutic agent is a polypeptide that interacts with a plasma membrane protein, a nuclear membrane protein, a peripheral membrane protein, an intracellular-membrane protein, a transporter, a channel protein (e.g., an ion channel protein), an adhesin, a translocase, or a receptor. In some instances, the therapeutic agent is a polypeptide that interacts with a receptor. In some cases, the receptor is an ion channel protein. In some cases, a therapeutic agent is a polypeptide that interacts with an ion channel protein. In some cases, the receptor is a GPCR. In some cases, the therapeutic agent is a polypeptide that interacts with a GPCR.

In some embodiments, the polypeptide is an antibody or its binding fragment thereof. In some instances, the therapeutic agent is an antibody or its binding fragment thereof. In some cases, an antibody or its binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof.

In some embodiments, described herein is a method of screening an antibody or its binding fragment thereof against a modified multispanning membrane polypeptide, comprising a) generating a modified multispanning membrane polypeptide library by a random mutagenesis method; b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; c) expressing the first set of expression vectors in a first plurality of host cells in the presence or absence of at least one selection agent to select for a set of stably folded multispanning membrane polypeptides; d) generating a production vector comprising a second polynucleotide encoding a stably folded multispanning membrane polypeptide from the set of stably folded multispanning membrane polypeptide identified in step c); e) expressing the production vector in a second plurality of host cells, wherein the host cells are production host cells; 0 incubating a multispanning membrane polypeptide product generated from the production vector of step e) with an antibody or its binding fragment thereof; and g) detecting a binding between the multispanning membrane polypeptide product and the antibody or its binding fragment thereof. In some instances, the antibody or its binding fragment thereof is produced through a phage display or a yeast display method. In some cases, the antibody or its binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof.

In some cases, the method further comprises a) generating a second set of production vectors in which each production vector comprises a third polynucleotide encoding a stably folded multispanning membrane polypeptide from the set of stably folded multispanning membrane polypeptide identified in step c) above; b) expressing the second set of production vectors in a third plurality of host cells, wherein the host cells are production host cells; and c) analyzing a set of multispanning membrane polypeptide products by an analytical method to determine an expressed stably folded multispanning membrane polypeptide from the set with an enhanced or improved physicochemical property for screening against the antibody or its binding fragment thereof of step f) above, wherein the enhanced or improved physicochemical property is relative to a control multispanning membrane polypeptide. In some instances, the enhanced or improved physicochemical property comprises expression level, stability, conformational selectivity, homogeneity, protein crystallization, antigenicity, immunogenicity, or pathway activation selectivity. In some instances, the control comprises a wild-type multispanning membrane polypeptide or a modified multispanning membrane polypeptide with a different modification. In some instances, the binding in step g) above is detected by a flow cytometry method, by enzyme-linked immunosorbent assay (ELISA), by a backscattering interferometry method, a fluorescent polarization method, a surface plasmon resonance (SPR) method, a plasmon-waveguide resonance method, a nuclear magnetic resonance (NMR) method, an isothermal titration calorimetry method, or a thermal denaturation assay. In some instances, the binding in step g) above is detected by a flow cytometry method or by enzyme-linked immunosorbent assay (ELISA). In some cases, the flow cytometry method comprises magnetic-activated cell sorting (MACS) or fluorescence-activated cell sorting (FACS).

In some instances, the modified multispanning membrane polypeptide comprises a plasma membrane protein, a nuclear membrane protein, a peripheral membrane protein, an intracellular-membrane protein, a transporter, a channel protein (e.g., an ion channel protein), an adhesin, a translocase, or a receptor. In some instances, the modified multispanning membrane polypeptide is a modified ion channel protein. In some cases, the modified ion channel protein is a modified TRPV3, KCa3.1, or TRPC6. In some instances, the modified multispanning membrane polypeptide is a modified G protein coupled receptor (GPCR). In some cases, the modified GPCR is a modified CCR7, CCR10, GPR55, NTR1, EP2, or EP4 receptor.

In some embodiments, also described herein include an antibody or its binding fragment thereof, produced by a method described herein. In some instances, described herein is an isolated and purified antibody or its binding fragment thereof comprising a heavy chain CDR1, CDR2, and CDR3 sequence and a light chain CDR1, CDR2, and CDR3 sequence, wherein the heavy chain and light chain CDRs interact with a modified multispanning membrane polypeptide and wherein the antibody or its binding fragment thereof is produced by the process of: (a) generating a modified multispanning membrane polypeptide library by a random mutagenesis method; (b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; (c) expressing the first set of expression vectors in a first plurality of host cells in the presence or absence of at least one selection agent to select for a set of stably folded multispanning membrane polypeptides; (d) generating a production vector comprising a second polynucleotide encoding a stably folded multispanning membrane polypeptide from the set of stably folded multispanning membrane polypeptides identified in step c); (e) expressing the production vector in a second plurality of host cells, wherein the host cells are production host cells; (f) incubating a multispanning membrane polypeptide product generated from the production vector of step e) with a set of antibodies or their binding fragments thereof; and (g) selecting an antibody or its binding fragment thereof that binds specifically with the multispanning membrane polypeptide product. In some instances, the antibody or its binding fragment thereof is produced through a phage display or a yeast display method. In some instances, the antibody or its binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some instances, the modified multispanning membrane polypeptide is a modified ion channel protein. In some instances, the modified ion channel protein is a modified TRPV3, KCa3.1, or TRPC6. In some instances, the modified multispanning membrane polypeptide is a modified G protein coupled receptor (GPCR). In some instances, the modified GPCR is a modified CCR7, CCR10, GPR55, NTR1, EP2, or EP4 receptor.

In some instances, the host cell is a prokaryotic host cell, a mammalian host cell, or an insect host cell. In some cases, the first plurality of host cells comprises prokaryotic host cells. In some cases, the prokaryotic host cells are *E. coli* cells. In some cases, the second plurality of host cells comprises mammalian host cells or insect host cells.

"Antibodies" and "immunoglobulins" (Igs) are glycoproteins having the same structural characteristics. The terms are used synonymously. In some instances, the antigen specificity of the immunoglobulin is known.

The term "antibody" is used in the broadest sense and covers fully assembled antibodies, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the forgoing.

The terms "monoclonal antibody" and "mAb" as used herein refer to an antibody obtained from a substantially homogeneous population of antibodies, i.e., the individual antibodies comprising the population are identical except for possible naturally occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are called the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

The term "hypervariable region," when used herein, refers to the amino acid residues of an antibody that are responsible for antigen-binding. The hypervariable region comprises amino acid residues from a "complementarily determining region" or "CDR" (e.g., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest, 5th Ed. Public Health Service, National Institute of Health, Bethesda, Md.) and/or those residues from a "hypervariable loop" (e.g., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) J. Mol. Biol., 196:901-917). "Framework" or "FR" residues are those variable domain residues other than the hypervariable region residues, as herein deemed.

"Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) Protein Eng. 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H1}$) of the heavy chain. Fab fragments differ from Fab' fragments by the addition of a few residues at the carboxy terminus of the heavy chain $C_{H1}$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

Phage Display

In some embodiments, an antibody or its binding fragment thereof is produced through a phage display method. In some instances, $10^{10}$ phage variants that display binding antibodies are utilized. In some instances, a candidate modified multispanning membrane polypeptide identified in a selection process is expressed in a mammalian cell line (e.g., a stable mammalian cell line), from which the expressed polypeptide is then purified and immobilized to a nanoparticle or immobilized to a surface (e.g., a coated surface of a plate). In some instances, the expressed polypeptide is immobilized to a nanoparticle. In some instances, the nanoparticle comprises a paramagnetic nanoparticle, a superparamagnetic nanoparticle, a metal nanoparticle, or an inorganic nanotube. In some instances, the nanoparticle is a paramagnetic nanoparticle. In some instances, a nanoparticle is further derivatized with a reactive tag, for example, such as a streptavidin tag, a biotin tag, or a reactive moiety capable of conjugating to a modified multispanning membrane polypeptide described herein.

In some instances, immobilized nanoparticle comprising a modified multispanning membrane polypeptide described herein is then screened against a phage library where e.g., a magnetic separation is used to isolate phage displaying antibodies with selective affinity for the modified multispanning membrane polypeptide target. In some instances, enriched phage populations are separated into clonal isolates and phage-encoded antibody genes are sequenced and cloned into mammalian expression vectors for production.

In some instances, one or more methods are utilized to screen an antibody or its binding fragment thereof bound to an immobilized modified multispanning membrane polypeptide described herein. In some instances, a flow cytometry method is utilized to screen an antibody or its binding fragment thereof bound to an immobilized modified multispanning membrane polypeptide described herein. In some cases, the flow cytometry comprises magnetic-activated cell sorting (MACS) or fluorescence-activated cell sorting (FACS). In some cases, enzyme-linked immunosorbent assay (ELISA) is utilized to screen an antibody or its binding fragment thereof bound to an immobilized modified multispanning membrane polypeptide described herein.

In some cases, a modified multispanning membrane polypeptide described herein is further formulated with a liposome, e.g., a liposomal encapsulated nanoparticle (e.g., with polymer Amphipol (A8-35)), prior to screening against a phage library where e.g., a magnetic separation is used to isolate phage displaying antibodies with selective affinity for the modified multispanning membrane polypeptide target.

In some instances, a phase display antibody library comprises Griffin-1 library (H Griffin, MRC, Cambridge, UK), Tomlinson I Library, or such as those described in Schofield, et al., "Application of phage display to high throughput antibody generation and characterization," Genome Biology 8: R254 (2007).

Yeast Display

In some embodiments, an antibody or its binding fragment thereof is produced through a yeast display method. In some instances, a yeast surface display comprises a eukaryotic expression apparatus which facilitates mammalian (e.g., human) protein folding and post-translational modification, and further enables quantitative and visualizable selection using fluorescence-activated cell sorting (FACS). In some instances, a yeast display system utilizes the yeast *Saccharomyces cerevisiae*.

In some instances, a candidate modified multispanning membrane polypeptide identified in a selection process is expressed, purified, and then immobilized to a nanoparticle or immobilized to a surface (e.g., a coated surface of a plate). In some instances, the expressed polypeptide is immobilized to a nanoparticle. In some instances, the nanoparticle comprises a paramagnetic nanoparticle, a superparamagnetic nanoparticle, a metal nanoparticle, or an inorganic nanotube. In some instances, the nanoparticle is a paramagnetic nanoparticle. In some instances, a nanoparticle is further derivatized with a reactive tag, for example, such as a streptavidin tag, a biotin tag, or a reactive moiety capable of conjugating to a modified multispanning membrane polypeptide described herein.

In some instances, immobilized nanoparticle comprising a modified multispanning membrane polypeptide described herein is then screened against a yeast display library where e.g., a magnetic separation is used to isolate yeast displaying antibodies with selective affinity for the modified multispanning membrane polypeptide target.

In some instances, one or more methods are utilized to screen an antibody or its binding fragment thereof bound to an immobilized modified multispanning membrane polypeptide described herein. In some instances, a flow cytometry method is utilized to screen an antibody or its binding fragment thereof bound to an immobilized modified multispanning membrane polypeptide described herein. In some cases, the flow cytometry comprises magnetic-activated cell sorting (MACS) or fluorescence-activated cell sorting (FACS). In some cases, enzyme-linked immunosorbent assay (ELISA) is utilized to screen an antibody or its binding fragment thereof bound to an immobilized modified multispanning membrane polypeptide described herein.

FACS is restricted to the selection of a relatively small population of cells. For efficient selection of a large library, additional steps of magnetic-activated cell sorting (MACS) are needed to reduce the library to a size that FACS can sort. Given the relatively large volume of yeast cells and lower library density ($10^9$ cells/ml) compared with phages, to effectively select a library of around $1 \times 10^{10}$ entities, multiple parallel MACS and FACS processes are required, with tens to hundreds of milliliters of starting yeast.

In some embodiments, examples of yeast display antibody libraries comprise those described in Feldhaus et al., "Flow-cytometric isolation of human antibodies form a nonimmune *Saccharomyces cerevisiae* surface display library," 21(2): 163-170 (2003); Weaver-Feldhaus et al., "Yeast mating for combinatorial Fab library generation and surface display," 564(1-2): 24-34 (2004).

Additional Methods of Screening a Polypeptide

In some embodiments, an additional method is used for screening a candidate modified multispanning membrane polypeptide described herein. In some instances, the additional method comprises generating or raising an antibody or its binding fragment thereof and then screening against a candidate modified multispanning membrane polypeptide described herein. In some cases, a method of generating or raising an antibody or its binding fragment thereof comprises inoculating a mammal (e.g., a mouse, rat or rabbit) with a modified multispanning membrane polypeptide fragment described herein, with a cultured cell expressing a modified multispanning membrane polypeptide antigen, with a modified multispanning membrane polypeptide-expressing dendritic cell, with dendritic-cell derived exosomes, with a budded viral form of recombinant extracellular baculovirus containing a candidate modified multispanning membrane polypeptide, with a cell membrane comprising candidate modified multispanning membrane polypeptide, or with a purified candidate modified multispanning membrane polypeptide.

In some cases, a method of generating or raising an antibody or its binding fragment thereof comprises inoculating a mammal (e.g., a mouse, rat, or rabbit) with a modified multispanning membrane polypeptide fragment described herein. In some instances, the polypeptide fragment comprises about 15, 20, 25, 30, 35, 40, 50, 60, 70, 80, 90, 100, or more amino acid residues in length. In some instances, the polypeptide fragment comprises a GPCR fragment. In some instances, the GPCR fragment comprises the N-terminal portion, the C-terminal portion, one or more of the TM core, an exoloop, an intracellular loop, or a combination thereof. In some instances, the method further comprises harvesting and purifying an antibody against the polypeptide fragment (e.g., a GPCR fragment).

In some instances, a method of generating or raising an antibody or its binding fragment thereof comprises inoculating a mammal (e.g., a mouse, rat or rabbit) with a cultured cell expressing a modified multispanning membrane polypeptide antigen. In some instances, the modified multispanning membrane polypeptide antigen is a modified GPCR antigen. In some instances, a method of generating or raising an antibody or its binding fragment thereof comprises inoculating a mammal (e.g., a mouse, rat or rabbit) with a cultured cell expressing a modified GPCR antigen. In some instances, the method further comprises harvesting and purifying an antibody against the cultured cell expressing a modified multispanning membrane polypeptide antigen (e.g., a modified GPCR antigen).

In some instances, a method of generating or raising an antibody or its binding fragment thereof comprises inoculating a mammal (e.g., a mouse, rat or rabbit) with a modified multispanning membrane polypeptide-expressing dendritic cell. In some instances, the dendritic cell expresses a modified GPCR. In some instances, a method of generating or raising an antibody or its binding fragment thereof comprises inoculating a mammal (e.g., a mouse, rat or rabbit) with a modified GPCR-expressing dendritic cell. In some instances, the method further comprises harvesting and purifying an antibody against a modified multispanning membrane polypeptide-expressing dendritic cell (e.g., a modified GPCR-expressing dendritic cell).

In some instances, a method of generating or raising an antibody or its binding fragment thereof comprises inoculating a mammal (e.g., a mouse, rat or rabbit) with dendritic-cell derived exosomes. In some instances, a dendritic-cell derived exosome comprises an antigen (e.g., a multispanning membrane polypeptide antigen) which then includes activation of the antigen-specific B-cell antibody response. In some cases, the dendritic-cell derived exosome comprises a multispanning membrane polypeptide antigen. In some cases, the multispanning membrane polypeptide antigen is a GPCR antigen. In some cases, a method of generating or raising an antibody or its binding fragment thereof comprises inoculating a mammal (e.g., a mouse, rat or rabbit) with dendritic-cell derived exosomes comprising a GPCR antigen. In some instances, the method further comprises harvesting and purifying an antibody against the dendritic-cell derived exosomes.

In some instances, a method of generating or raising an antibody or its binding fragment thereof comprises inoculating a mammal (e.g., a mouse, rat or rabbit) with a budded viral form of recombinant extracellular baculovirus containing a modified multispanning membrane polypeptide. In some instances, the modified multispanning membrane polypeptide is a modified GPCR. In some cases, a method of generating or raising an antibody or its binding fragment thereof comprises inoculating a mammal (e.g., a mouse, rat or rabbit) with a budded viral form of recombinant extracellular baculovirus containing a modified GPCR. In some instances, the method further comprises harvesting and purifying an antibody against the budded viral form of recombinant extracellular baculovirus containing a modified multispanning membrane polypeptide (e.g., a modified GPCR).

In some instances, a method of generating or raising an antibody or its binding fragment thereof comprises inoculating a mammal (e.g., a mouse, rat or rabbit) with a cell membrane comprising a modified multispanning membrane polypeptide. In some instances, the modified multispanning membrane polypeptide is a modified GPCR. In some instances, a method of generating or raising an antibody or its binding fragment thereof comprises inoculating a mammal (e.g., a mouse, rat or rabbit) with a cell membrane comprising a modified GPCR. In some instances, the method further comprises harvesting and purifying an antibody against the cell membrane comprising a modified multispanning membrane polypeptide (e.g., a modified GPCR).

In some instances, a method of generating or raising an antibody or its binding fragment thereof comprises inoculating a mammal (e.g., a mouse, rat or rabbit) with a purified modified multispanning membrane polypeptide. In some instances, the modified multispanning membrane polypeptide is a modified GPCR. In some instances, a method of generating or raising an antibody or its binding fragment thereof comprises inoculating a mammal (e.g., a mouse, rat or rabbit) with a purified modified GPCR. In some instances, the method further comprises harvesting and purifying an antibody against the purified modified multispanning membrane polypeptide (e.g., a purified modified GPCR).

Methods of Screening a Small Molecule

In some embodiments, the therapeutic agent is a small molecule. In some cases, the small molecule is a drug or a small molecule fragment. In some instances, the drug is a molecule (e.g., a chemical molecule or a biologics) that exhibits a therapeutic effect. In other instances, the drug is a molecule (e.g., a chemical molecule or a biologics) that does not exhibits a therapeutic effect. In some instances, the therapeutic agent described herein is a drug (e.g., a chemical molecule or a biologics) that exhibits a therapeutic effect. In other instances, the therapeutic agent described herein is a drug (e.g., a chemical molecule or a biologics) that does not exhibits a therapeutic effect.

In some embodiments, described herein is a method of screening a small molecule against a modified multispanning membrane polypeptide, comprising a) generating a modified multispanning membrane polypeptide library by a random mutagenesis method; b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; c) expressing the first set of expression vectors in a first plurality of host cells in the presence or absence of at least one selection agent to select for a set of stably folded multispanning membrane polypeptides; d) generating a production vector comprising a second polynucleotide encoding a stably folded multispanning membrane polypeptide from the set of stably folded multispanning membrane polypeptide identified in step c); e) expressing the production vector in a second plurality of host cells, wherein the host cells are production host cells; f) incubating a multispanning membrane polypeptide product generated from the production vector of step e) with a small molecule; and g) detecting a binding between the multispanning membrane polypeptide product and the small molecule.

In some cases, the method further comprises a) generating a second set of production vectors in which each production vector comprises a third polynucleotide encoding a stably folded multispanning membrane polypeptide from the set of stably folded multispanning membrane polypeptides identified in step c) above; b) expressing the second set of production vectors in a third plurality of host cells, wherein the host cells are production host cells; and c) analyzing a set of multispanning membrane polypeptide products by an analytical method to determine an expressed stably folded multispanning membrane polypeptide from the set with an enhanced or improved physicochemical property for screening against the small molecule of step f) above, wherein the enhanced or improved physicochemical property is relative to a control multispanning membrane polypeptide. In some instances, the enhanced or improved physicochemical property comprises expression level, stability, conformational selectivity, homogeneity, protein crystallization, antigenicity, immunogenicity, or pathway activation selectivity. In some instances, the control comprises a wild-type multispanning membrane polypeptide or a modified multispanning membrane polypeptide with a different modification. In some instances, the binding in step g) above is detected by an analytical technique such as isothermal titration calorimetry, surface plasmon resonance (SPR), backscattering interferometry, a nuclear magnetic resonance (NMR) method, a fluorescent polarization method, a plasmon-waveguide resonance method, a fluorescent ligand binding assay, a radioligand binding assay and the like.

In some instances, the small molecule is a small molecule fragment. In some cases, the small molecule fragment is a non-naturally occurring molecule. In some cases, the small molecule fragment does not include a natural and/or non-natural peptide fragment, or a small molecule that is produced naturally within the body of a mammal (e.g. a metabolite).

In some instances, the small molecule fragment comprises a molecule weight of about 100 Dalton or higher. In some embodiments, the small molecule fragment comprises a molecule weight of about 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 500, 550, 600, 650, 700, 750, 800, 850, 900, 950, 1000 Dalton, or higher.

In some instances, the small molecule fragment comprises micromolar or millimolar binding affinity. In some instances, the small molecule fragment comprises a binding affinity of about 1 µM, 10 µM, 100 µM, 500 µM, 1 mM, 10 mM, or higher.

In some cases, the small molecule fragment has a high ligand efficiency (LE). Ligand efficiency is the measurement of the binding energy per atom of a ligand to its binding partner (e.g., a GPCR). In some instances, the ligand efficiency is defined as the ratio of the Gibbs free energy (ΔG) to the number of non-hydrogen atoms of the compound (N):

$$LE=(\Delta G)/N.$$

In some cases, LE is also arranged as:

$$LE=1.4(-\log IC_{50})/N.$$

In some instances, the LE score is about 0.3 kcal mol$^{-1}$ HA$^{-1}$, about 0.35 kcal mol$^{-1}$ HA$^{-1}$, about 0.4 kcal mol$^{-1}$ HA$^{-1}$, or higher.

In some embodiments, the small molecule fragment is designed based on the Rule of 3. In some embodiments, the Rule of 3 comprises a non-polar solvent-polar solvent (e.g. octanol-water) partition coefficient log P of about 3 or less, a molecular mass of about 300 Daltons or less, about 3 hydrogen bond donors or less, about 3 hydrogen bond acceptors or less, and about 3 rotatable bonds or less.

In some embodiments, the small molecule fragment further comprises a pharmacokinetic parameter that is unsuitable as a therapeutic agent for administration without further optimization of the small molecule fragment. In some instances, the pharmacokinetic parameter that is suitable as a therapeutic agent comprises a parameter in accordance with FDA guideline, or in accordance with a guideline from an equivalent Food and Drug Administration outside of the United States. In some instances, the pharmacokinetic parameter comprises a peak plasma concentration (Cmax), the lowest concentration of a therapeutic agent (Cmin), volume of distribution, time to reach Cmax, elimination half-life, clearance, and the like. In some embodiments, the pharmacokinetic parameter of a small molecule fragment is outside of the parameters set by the FDA guidelines, or by an equivalent Food and Drug Administration outside of the United States. In some instances, a skilled artisan understands in view of a pharmacokinetic parameter of a small molecule fragment described herein that the small molecule fragment is unsuited as a therapeutic agent without further optimization.

In some instances, exemplary small molecule fragment libraries include, but are not limited to, ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, *Allium* from Vitas-M Laboratory, or *Zenobia* fragment library.

Vaccines

In some embodiments, described herein further include vaccines and vaccine formulations based on a modified multispanning membrane polypeptide described herein. In some instances, a vaccine is prepared from live attenuated pathogens, or inactivated pathogens that have been inactivated by e.g. chemicals, heat, or radiation. In some instances, a vaccine contains subunits or portions of a modified multispanning membrane polypeptide described herein, in which the subunits or portions are optionally conjugated. In some instances, a vaccine is prepared as a peptide-based vaccine, a nucleic acid-based vaccine, an antibody based vaccine, or an antigen-presenting cell based vaccine.

In some instances, a vaccine is formulated in a conventional manner using one or more physiologically acceptable carriers including excipients and auxiliaries which facilitate processing of the active agents into preparations which is used pharmaceutically. Proper formulation is dependent upon the route of administration chosen. Any of the well-known techniques, carriers, and excipients are used as suitable and as understood in the art.

In some cases, the vaccine is formulated as a peptide-based vaccine, a nucleic acid-based vaccine, an antibody based vaccine, or a cell based vaccine. For example, a vaccine composition sometimes includes naked cDNA in cationic lipid formulations; lipopeptides (e.g., Vitiello, A. et al., J. Clin. Invest. 95:341, 1995), naked cDNA or peptides, encapsulated e.g., in poly(DL-lactide-co-glycolide) ("PLG") microspheres (see, e.g., Eldridge, et al., Molec. Immunol. 28:287-294, 1991: Alonso et al, Vaccine 12:299-306, 1994; Jones et al, Vaccine 13:675-681, 1995); peptide composition contained in immune stimulating complexes (ISCOMS) (see, e.g., Takahashi et al, Nature 344:873-875, 1990; Hu et al, Clin Exp Immunol. 113:235-243, 1998); or multiple antigen peptide systems (MAPs) (see e.g., Tam, J. P., Proc. Natl Acad. Sci. U.S.A. 85:5409-5413, 1988; Tarn, J. P., J. Immunol. Methods 196:17-32, 1996). Sometimes, a vaccine is formulated as a peptide-based vaccine, or nucleic acid-based vaccine in which the nucleic acid encodes a modified multispanning membrane polypeptide described herein. Sometimes, a vaccine is formulated as an antibody-based vaccine. Sometimes, a vaccine is formulated as a cell-based vaccine.

Antibody Based Vaccine

In some embodiments, a vaccine is an antibody-based vaccine. In some instances, an antibody or its binding fragment thereof binds to a modified multispanning membrane polypeptide described herein. In some instances, a vaccine comprises an isolated and purified antibody or its binding fragment thereof comprising a heavy chain CDR1, CDR2, and CDR3 sequence and a light chain CDR1, CDR2, and CDR3 sequence, wherein the heavy chain and light chain CDRs interact with a modified multispanning membrane polypeptide and wherein the antibody or its binding fragment thereof is produced by the process of: (a) generating a modified multispanning membrane polypeptide library by a random mutagenesis method; (b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; (c) expressing the first set of expression vectors in a first plurality of host cells in the presence or absence of at least one selection agent to select for a set of stably folded multispanning membrane polypeptides; (d) generating a production vector comprising a second polynucleotide encoding a stably folded multispanning membrane polypeptide from the set of stably folded multispanning membrane polypeptide identified in step c); (e) expressing the production vector in a second plurality of host cells, wherein the host cells are production host cells; (f) incubating a multispanning membrane polypeptide product generated from the production vector of step e) with a set of antibodies or their binding fragments thereof; and (g)

selecting an antibody or its binding fragment thereof that binds specifically with the multispanning membrane polypeptide product. In some instances, the antibody or its binding fragment thereof is produced through a phage display or a yeast display method. In some instances, the modified multispanning membrane polypeptide is a modified ion channel protein. In some instances, the modified ion channel protein is a modified TRPV3, KCa3.1, or TRPC6. In some instances, the modified multispanning membrane polypeptide is a modified G protein coupled receptor (GPCR). In some instances, the modified GPCR is a modified CCR7, CCR10, GPR55, NTR1, EP2, or EP4 receptor. In some instances, the vaccine further comprises an adjuvant. In some instances, the adjuvant comprises GM-CSF.

In some instances, an antibody-based vaccine is formulated using any of the well-known techniques, carriers, and excipients as suitable and as understood in the art. As described above, an antibody or its binding fragment thereof comprises, for example, a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof. In some instances, an antibody is a natural antibody, a chimeric antibody, a humanized antibody, or an antibody fragment. In some cases, a monoclonal antibody is obtained from any suitable species e.g. murine, rabbit, sheep, goat, or human monoclonal antibodies.

Nucleic Acid-Based Vaccine

In some embodiments, a vaccine is formulated as a nucleic acid-based vaccine. In some instances, the nucleic acid-based vaccine is formulated using any of the well-known techniques, carriers, and excipients as suitable and as understood in the art. In some cases, the nucleic acid is DNA, both genomic and cDNA, RNA, or a hybrid, where the nucleic acid contains combinations of deoxyribo- and ribo-nucleotides, and combinations of bases including uracil, adenine, thymine, cytosine, guanine, inosine, xanthine hypoxanthine, isocytosine, and isoguanine. In some cases, nucleic acids are obtained by chemical synthesis methods or by recombinant methods. In some instances, the vaccine is a DNA-based vaccine, an RNA-based vaccine, a hybrid DNA/RNA based vaccine, or a hybrid nucleic acid/peptide based vaccine.

In some cases, a nucleic acid-based vaccine described herein comprises a polynucleotide encoding a modified multispanning membrane polypeptide, wherein the modified multispanning membrane polypeptide is produced by the process of: (a) generating a modified multispanning membrane polypeptide library by a random mutagenesis method; (b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; (c) expressing the first set of expression vectors in a first plurality of host cells in the presence or absence of at least one selection agent to select for a set of stably folded multispanning membrane polypeptides; (d) generating a second set of production vectors in which each production vector comprises a third polynucleotide encoding a stably folded multispanning membrane polypeptide from the set of stably folded multispanning membrane polypeptides identified in step c); (e) expressing the second set of production vectors in a second plurality of host cells, wherein the host cells are production host cells; and (f) analyzing a set of multispanning membrane polypeptide products generated from the second set of production vectors of step e) with an analytical method to determine a multispanning membrane polypeptide product from the set with an enhanced or improved physicochemical property for generation of a vaccine, wherein the enhanced or improved physicochemical property is relative to a control multispanning membrane polypeptide. In some instances, the enhanced or improved physicochemical property comprises expression level, stability, conformational selectivity, homogeneity, protein crystallization, antigenicity, immunogenicity, or pathway activation selectivity. In some instances, the control comprises a wild-type multispanning membrane polypeptide or a modified multispanning membrane polypeptide with a different modification.

In some instances, the modified multispanning membrane polypeptide is a modified ion channel protein. In some instances, the modified ion channel protein is a modified TRPV3, KCa3.1, or TRPC6. In some instances, the modified multispanning membrane polypeptide is a modified G protein coupled receptor (GPCR). In some instances, the modified GPCR is a modified CCR7, CCR10, GPR55, NTR1, EP2, or EP4 receptor. In some instances, the vaccine further comprises an adjuvant. In some instances, the adjuvant comprises GM-CSF.

In some instances, nucleic acid molecules as used herein refer to at least two nucleotides covalently linked together. A nucleic acid described herein contains, for example, phosphodiester bonds, although in some cases, as outlined below (for example in the construction of primers and probes such as label probes), nucleic acid analogs are included that have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991), and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988), Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-O atom with the 4'-C atom. These modifications of the ribose-phosphate backbone can be done to increase the stability and half-life of such molecules in physiological environments. For example, PNA:DNA and LNA-DNA hybrids can exhibit higher stability and thus can be used in some embodiments. The target nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

In some instances, the vector is a circular plasmid or a linear nucleic acid. In some cases, the circular plasmid or linear nucleic acid is capable of directing expression of a particular nucleotide sequence in an appropriate subject cell. In some cases, the vector has a promoter operably linked to the polypeptide-encoding nucleotide sequence, which is operably linked to termination signals. In some instances, the vector also contains sequences required for proper translation of the nucleotide sequence. The vector comprising the nucleotide sequence of interest can be chimeric, meaning that at least one of its components is heterologous with respect to at least one of its other components. The expression of the nucleotide sequence in the expression cassette can be under the control of a constitutive promoter or of an inducible promoter, which can initiate transcription only when the host cell is exposed to some particular external stimulus.

In some instances, the vector is a plasmid. In some cases, the plasmid is useful for transfecting cells with nucleic acid encoding the polypeptide, which the transformed host cells can be cultured and maintained under conditions wherein expression of the polypeptide takes place.

In some instances, the plasmid comprises a nucleic acid sequence that encodes one or more of the modified multispanning membrane polypeptide disclosed herein. A single plasmid, for example, contains coding sequence for a single polypeptide, or coding sequence for more than one polypeptide. Sometimes, the plasmid further comprises coding sequence that encodes an adjuvant, such as an immune stimulating molecule, or such as a cytokine. In some instances, the plasmid further comprises an initiation codon, a stop codon, a promoter that is operably linked to the coding sequence, and an enhancer upstream of the coding sequence.

In some instances, the plasmid comprises a mammalian origin of replication in order to maintain the plasmid extra-chromosomally and produce multiple copies of the plasmid in a cell. The plasmid can be pVAXI, pCEP4, or pREP4 from Invitrogen (San Diego, Calif.).

In some instances, the plasmid further comprises a regulatory sequence, which enables gene expression in a cell into which the plasmid is administered. In some cases, the coding sequence further comprises a codon that allows for more efficient transcription of the coding sequence in the host cell.

Exemplary plasmids include pSE420 (Invitrogen, San Diego, Calif.), which can be used for protein production in *Escherichia coli* (*E. coli*); pYES2 (Invitrogen, San Diego, Calif.), which is used for protein production in *Saccharomyces cerevisiae* strains of yeast; MAXBAC™ complete baculovirus expression system (Invitrogen, San Diego, Calif.), which is used for protein production in insect cells; and pcDNA I or pcDNA3 (Invitrogen, San Diego, Calif.), which are used for protein production in mammalian cells such as Chinese hamster ovary (CHO) cells.

In some instances, the vector is a circular plasmid, which transforms a target cell by integrating into the cellular genome or existing extrachromosomally (e.g., autonomous replicating plasmid with an origin of replication). Exemplary vectors include pVAX, pcDNA3.0, or provax, or any other expression vector capable of expressing DNA encoding the antigen and enabling a cell to translate the sequence to an antigen that is recognized by the immune system.

In some instances, the nucleic acid-based vaccine is a linear nucleic acid vaccine, or linear expression cassette ("LEC"), that is capable of being efficiently delivered to a subject via electroporation and expressing one or more polypeptides disclosed herein. The LEC can be any linear DNA devoid of any phosphate backbone. The DNA can encode one or more polypeptides disclosed herein. The LEC can contain a promoter, an intron, a stop codon, and/or a polyadenylation signal. The expression of the polypeptide may be controlled by the promoter. In some cases, the LEC does not contain any antibiotic resistance genes and/or a phosphate backbone. In some cases, the LEC does not contain other nucleic acid sequences unrelated to the polypeptide expression.

Peptide-Based Vaccine

In some instances, a vaccine is formulated as a peptide-based vaccine. In some cases, a peptide-based vaccine described herein comprises a modified multispanning membrane polypeptide, wherein the modified multispanning membrane polypeptide is produced by the process of: (a) generating a modified multispanning membrane polypeptide library by a random mutagenesis method; (b) generating a first set of expression vectors in which each expression vector comprises: a first polynucleotide encoding a modified multispanning membrane polypeptide from the library of step a); a first selection marker gene operably linked to the C-terminus of the polynucleotide; and optionally a second selection marker gene operably linked to the N-terminus of the polynucleotide; (c) expressing the first set of expression vectors in a first plurality of host cells in the presence or absence of at least one selection agent to select for a set of stably folded multispanning membrane polypeptides; (d) generating a second set of production vectors in which each production vector comprises a third polynucleotide encoding a stably folded multispanning membrane polypeptide from the set of stably folded multispanning membrane polypeptides identified in step c); (e) expressing the second set of production vectors in a second plurality of host cells, wherein the host cells are production host cells; and (f) analyzing a set of multispanning membrane polypeptide products generated from the second set of production vectors of step e) with an analytical method to determine a multispanning membrane polypeptide product from the set with an enhanced or improved physicochemical property for generation of a vaccine, wherein the enhanced or improved physicochemical property is relative to a control multispanning membrane polypeptide. In some instances, the enhanced or improved physicochemical property comprises expression level, stability, conformational selectivity, homogeneity, protein crystallization, antigenicity, immunogenicity, or pathway activation selectivity. In some instances, the control comprises a wild-type multispanning membrane polypeptide or a modified multispanning membrane polypeptide with a different modification. In some instances, the modified multispanning membrane polypeptide is a modified ion channel protein. In some instances, the modified ion channel protein is a modified TRPV3, KCa3.1, or TRPC6. In some instances, the modified multispanning membrane polypeptide is a modified G protein coupled receptor (GPCR). In some instances, the modified GPCR is a modified CCR7, CCR10, GPR55, NTR1, EP2, or EP4 receptor. In some instances, the vaccine further comprises an adjuvant. In some instances, the adjuvant comprises GM-CSF.

In some cases, a peptide-based vaccine is formulated using any of the well-known techniques, carriers, and excipients as suitable and as understood in the art. In some instances, one or more modified multispanning membrane polypeptides are formulated as a cocktail of multiple polypeptides containing the same sequence, or a cocktail of multiple copies of different polypeptides. In some instances, the peptides are modified, such as for example by lipidation, or attachment to a carrier protein. In some cases, lipidation is the covalent attachment of a lipid group to a polypeptide. In some instances, lipidated peptides, or lipidated polypeptides, stabilize structures and enhance efficacy of the vaccine treatment.

In some instances, lipidated peptides are further incorporated into a liposome. For example, the lipid portion of the lipidated peptide spontaneously integrates into the lipid bilayer of a liposome. Thus, a lipopeptide is presented on the "surface" of a liposome. In some instances, lipidated peptides refer to a modified multispanning membrane polypeptide that is encapsulated within a liposome.

Exemplary liposomes suitable for incorporation in the formulations include, and are not limited to, multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). In some instances, a liposome comprises Amphipol (A8-35). Techniques for preparing liposomes are described in, for example, COLLOIDAL DRUG DELIVERY SYSTEMS, vol. 66 (J. Kreuter ed., Marcel Dekker, Inc. (1994)).

Depending on the method of preparation, liposomes are unilamellar or multilamellar, and vary in size with diameters ranging from about 0.02 µm to greater than about 10 µm.

In some instances, liposomes adsorb many types of cells and then release an incorporated agent (e.g., a modified multispanning membrane polypeptide described herein). In some cases, the liposomes fuse with the target cell, whereby the contents of the liposome are then emptied into the target cell. In some cases, a liposome is endocytosed by cells that are phagocytic. Endocytosis is then followed by intralysosomal degradation of liposomal lipids and release of the encapsulated agents. Scherphof et al., Ann. N.Y. Acad. Sci., 446: 368 (1985).

In some instances, liposomes provided herein also comprise carrier lipids. In some embodiments the carrier lipids are phospholipids. Carrier lipids capable of forming liposomes include, but are not limited to, dipalmitoylphosphatidylcholine (DPPC), phosphatidylcholine (PC; lecithin), phosphatidic acid (PA), phosphatidylglycerol (PG), phosphatidylethanolamine (PE), or phosphatidylserine (PS). Other suitable phospholipids further include distearoylphosphatidylcholine (DSPC), dimyristoylphosphatidylcholine (DMPC), dipalmitoylphosphatidyglycerol (DPPG), di stearoylphosphatidyglycerol (DSPG), dimyristoylphosphatidylglycerol (DMPG), dipalmitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE) and the like, or combinations thereof. In some embodiments, the liposomes further comprise a sterol (e.g., cholesterol) which modulates liposome formation. The carrier lipids can be any known non-phosphate polar lipids.

In some instances, a modified multispanning membrane polypeptide described herein is also attached to a carrier protein for delivery as a vaccine. In some instances, the carrier protein is an immunogenic carrier element and is attached by any recombinant technology. Exemplary carrier proteins include Mariculture keyhole limpet hemocyanin (mcKLH), PEGylated mcKLH, Blue Carrier* Proteins, bovine serum albumin (BSA), cationized BSA, ovalbumin, and bacterial proteins such as tetanus toxoid (TT).

In some cases, a polypeptide is prepared as multiple antigenic peptides (MAPs). In some cases, a modified multispanning membrane polypeptide is attached at the N-terminus or the C-terminus to small non-immunogenic cores. In some cases, the core comprises a dendritic core residue or matrix composed of bifunctional units. Suitable core molecules for constructing MAPs include, for example, ammonia, ethylenediamine, aspartic acid, glutamic acid, and lysine. As used herein, the "linear portion or molecule" of a MAP system structure refers to the antigenic peptides that are linked to the core matrix. Thus, a cluster of antigenic epitopes form the surface of a MAP and a small matrix forms its core. The dendritic core, and the entire MAP are, in some instances, synthesized on a solid resin using a classic Merrifield synthesis procedure. MAP synthesis, is generally described, for example, in U.S. Pat. Nos. 5,580,563, and 6,379,679, and Tam, Proc. Natl. Acad. Sci. USA 85:5409-5413, 1988.

In some instances, a modified multispanning membrane polypeptide is chemically synthesized, or recombinantly expressed in a cell system or a cell-free system. A peptide is synthesized, for example, by a liquid-phase synthesis, a solid-phase synthesis, or by microwave assisted peptide synthesis.

After generation of a polypeptide, the polypeptide is sometimes subjected to one or more rounds of purification steps to remove impurities. In some cases, the purification step comprises a chromatographic step utilizing separation methods such as affinity-based, size-exclusion based, ion-exchange based, or the like. In some cases, the polypeptide is at most 30%, 40%, 50%, 60%, 70%, 80%, 90%, 95%, 99%, 99.9%, or 100% pure or without the presence of impurities. In some cases, the polypeptide is at least 30%, 40%, 50%, 60%, 70%, 80%, 90%, 95%, 99%, 99.9%, or 100% pure or without the presence of impurities.

As used herein, a polypeptide includes natural amino acids, unnatural amino acids, or a combination thereof. In some instances, an amino acid residue refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes, without limitation, α-amino acids, natural amino acids, non-natural amino acids, and amino acid analogs.

In some instances, α-amino acid refers to a molecule containing both an amino group and a carboxyl group bound to a carbon which is designated the α-carbon.

In some instances, β-amino acid refers to a molecule containing both an amino group and a carboxyl group in a β configuration.

In some instances, naturally occurring amino acid refers to any one of the twenty amino acids commonly found in peptides synthesized in nature, and known by the one letter abbreviations A, R, N, C, D, Q, E, G, H, I, L, K, M, F, P, S, T, W, Y, and V.

In some instances, hydrophobic amino acids include small hydrophobic amino acids and large hydrophobic amino acids. Small hydrophobic amino acid are glycine, alanine, proline, and analogs thereof. Large hydrophobic amino acids are valine, leucine, isoleucine, phenylalanine, methionine, tryptophan, and analogs thereof. Polar amino acids are serine, threonine, asparagine, glutamine, cysteine, tyrosine, and analogs thereof. Charged amino acids are lysine, arginine, histidine, aspartate, glutamate, and analogs thereof.

In some instances, amino acid analog refers to a molecule which is structurally similar to an amino acid and which is substituted for an amino acid in the formation of a peptidomimetic macrocycle Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

In some instances, non-natural amino acid refers to an amino acid which is not one of the twenty amino acids commonly found in peptides synthesized in nature, and known by the one letter abbreviations A, R, N, C, D, Q, E, G, H, I, L, K, M, F, P, S, T, W, Y, and V.

In some embodiments, non-natural amino acids or amino acid analogs include, without limitation, the following:

β-amino acid analogs such as the following: cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl) butyric acid; (S)-3-amino-4-(4-cyanophenyl)-butyric acid; (S)-3-amino-4-(4-fluorophenyl) butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine, O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Alanine, valine, glycine, or leucine analogs such as the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanine; β-cyclohexyl-D- alanine; β-cyclohexyl-L-alanine; β-cyclopenten-1-yl-alanine; β-cyclopentyl-alanine; β-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH.dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH.dicyclohexylammonium salt; cyclopentyl-Gly-OH.dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine-dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl)glycine; L-2-amino-3-(dimethylamino)-propionic acid; L-2-aminocaproic acid dicyclohexyl-ammonium salt; L-2-indanylglycine; L-allylglycine.dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogs can include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; Lys(Me)$_2$-OH; Lys(N$_3$)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxo-cyclohex-1-ylidene)ethyl)-D-ornithine; (Nδ-1-(4,4-dimethyl-2,6-dioxo-cyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg(Me)$_2$-OH (asymmetrical); Arg(Me)2-OH (symmetrical); Lys(ivDde)-OH; Lys(Me)2-OH·HCl; Lys(Me3)-OH chloride; Nω-nitro-D-arginine; and Nω-nitro-L-arginine.

Aspartic acid or glutamic acids analogs such as the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

Cysteine and methionine analogs such as the following: Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthionine-sulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

Phenylalanine and tyrosine analogs such as the following: β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2;4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenyl alanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Proline analogs such as the following: 3,4-dehydro-proline, 4-fluoro-proline, cis-4-hydroxy-proline, thiazolidine-2-carboxylic acid, and trans-4-fluoro-proline.

Serine and threonine analogs such as the following: 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Tryptophan analogs such as the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

In some embodiments, an amino acid analog is a racemic mixture. In some instances, the D isomer of the amino acid analog is used. In some cases, the L isomer of the amino acid analog is used. In some instances, the amino acid analog comprises chiral centers that are in the R or S configuration. Sometimes, the amino group(s) of a β-amino acid analog is optionally substituted with a protecting group, e.g., tert-butyloxycarbonyl (BOC group), 9-fluorenylmethyloxycarbonyl (FMOC), tosyl, and the like. Sometimes, the carboxylic acid functional group of a β-amino acid analog is protected, e.g., as its ester derivative. In some cases, the salt of the amino acid analog is used.

Antigen-Presenting Cell (APC) Based Vaccine

In some instances, a vaccine is an antigen-presenting cell (APC) based vaccine. In some cases, an APC based vaccine is formulated using any of the well-known techniques, carriers, and excipients as suitable and as understood in the art. APCs include monocytes, monocyte-derived cells, macrophages, and dendritic cells. Sometimes, APC based vaccine can be a dendritic cell-based vaccine.

In some instances, a dendritic cell-based vaccine is prepared by any methods well known in the art. In some cases, dendritic cell (DC) based vaccines are prepared through an ex vivo or in vivo method. The ex vivo method comprises, for example, the use of autologous DCs pulsed ex vivo with the polypeptides described herein, to activate or load the DCs prior to administration into the patient. In some instances, the in vivo method comprises targeting specific DC receptors using antibodies coupled with the polypeptides described herein. The DC-based vaccine can further comprise DC activators such as TLR3, TLR-7-8, and CD40 agonists. The DC-based vaccine can further comprise adjuvants and a pharmaceutically acceptable carrier.

Virus-Based Vaccine

In some embodiments, a vaccine is a virus-based vaccine. In some instances, a virus-based vaccine is generated based on live virus or on inactivated virus. Vaccines based on live virus uses an attenuated virus, or a virus that is cold-adapted. In some instances, vaccines based on inactivated virus comprise whole virion, split virion, or purified surface antigens (e.g. HA and/or N from influenza A virus). Chemical means for inactivating a virus can include treatment with an effective amount of one or more of the following agents: detergents, formaldehyde, β-propiolactone, methylene blue, psoralen, carboxyfuilerene (C60), binary ethylamine, acetyl ethyleneimine, or combinations thereof. Non-chemical methods of viral inactivation are known in the art, such as for example UV light or gamma irradiation.

In some cases, virions are harvested from virus-containing fluids by various methods. For example, a purification process can involve zonal centrifugation using a linear sucrose gradient solution that includes detergent to disrupt the virions. Antigens can be purified, after optional dilution, by diafiltration.

In some cases, split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process.

Adjuvant

In some instances, a vaccine described herein further comprises an adjuvant. In some instances, an adjuvant is used to enhance the immune response (humoral and/or cellular) elicited in a patient receiving the vaccine. Sometimes, adjuvants elicit a Th1-type response. Other times, adjuvants elicit a Th2-type response. In some instances, a Th1-type response is characterized by the production of cytokines such as IFN-γ as opposed to a Th2-type response which is characterized by the production of cytokines such as IL-4, IL-5, and IL-10.

In some aspects, lipid-based adjuvants, such as MPLA and MDP, can be used with the vaccines disclosed herein. Monophosphoryl lipid A (MPLA), for example, is an adjuvant that causes increased presentation of liposomal antigen to specific T Lymphocytes. In addition, a muramyl dipeptide (MDP) can also be used as a suitable adjuvant in conjunction with the vaccine formulations described herein.

In some instances, adjuvant comprises stimulatory molecules such as cytokines. Non-limiting examples of cytokines include: CCL20, α-interferon (IFN-a), β-interferon (IFN-β), γ-interferon, platelet derived growth factor (PDGF), TNFa, TNFp, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1-, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, INK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, and TAP2.

Additional adjuvants include: MCP-1, MW-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Fit, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, INK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2, and functional fragments thereof.

In some aspects, an adjuvant is a modulator of a toll like receptor. Examples of modulators of toll-like receptors include TLR-9 agonists and are not limited to small molecule modulators of toll-like receptors such as Imiquimod. Other examples of adjuvants that are used in combination with a vaccine described herein can include and are not limited to saponin, CpG ODN, and the like.

Sometime an adjuvant is a heat shock proteins molecular chaperone such as HSP60, HSP70, GroEL, GroES, DnaK, and DnaJ, responsible for the transportation and refolding of proteins.

Sometimes, an adjuvant is selected from bacteria toxoids, polyoxypropylene-polyoxyethylene block polymers, aluminum salts, liposomes, CpG polymers, oil-in-water emulsions, or a combination thereof.

Sometimes, an adjuvant is an oil-in-water emulsion. The oil-in-water emulsion can include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a high pressure homogenizer to provide stable emulsions. Droplets with a size less than 220 nm are preferred as they can be subjected to filter sterilization.

In some cases, the oils used include such as those from an animal (such as fish) or vegetable source. Sources for vegetable oils can include nuts, seeds, and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil, etc. The grain group can include: corn oil and oils of other cereal grains such as wheat, oats, rye, rice, teff, triticale, and the like. 6-10 carbon fatty acid esters of glycerol and 1,2-propanediol, while not occurring naturally in seed oils, may be prepared by hydrolysis, separation, and esterification of the appropriate materials starting from the nut and seed oils. Fats and oils from mammalian milk can be metabolizable and can therefore be used with the vaccines described herein. The procedures for separation, purification, saponification, and other means necessary for obtaining pure oils from animal sources are well known in the art. Fish can contain metabolizable oils which can be readily recovered. For example, cod liver oil, shark liver oils, and whale oil such as spermaceti can exemplify several of the fish oils which can be used herein. A number of branched chain oils can be synthesized biochemically in 5-carbon isoprene units and can be generally referred to as terpenoids. Shark liver oil contains a branched, unsaturated terpenoid known as squalene, 2,6,10,15,19,23-hexamethyl-2,6,10,14,18,22-tetracosahexaene. Squalane, the saturated analog to squalene, can also be used. Fish oils, including squalene and squalane, can be readily available from commercial sources or can be obtained by methods known in the art.

Other useful oils include, e.g., tocopherols, to include in vaccines for use in elderly patients (e.g. aged 60 years or older) due to vitamin E been reported to have a positive effect on the immune response in this patient group. Further, tocopherols have antioxidant properties that can help to stabilize the emulsions. Various tocopherols exist (α, β, γ, δ, ε or ξ) but α is usually used. An example of α-tocopherol is DL-α-tocopherol. α-tocopherol succinate can be compatible with influenza vaccines and can be a useful preservative as an alternative to mercurial compounds.

Mixtures of oils are sometimes used comprising, e.g. squalene and α-tocopherol. An oil content in the range of 2-20% (by volume) is sometimes used.

In some instances, surfactants are classified by their 'HLB' (hydrophile/lipophile balance). In some cases, surfactants have a HLB of at least 10, at least 15, and/or at least 16. Surfactants can include, but are not limited to: the polyoxyethylene sorbitan esters surfactants (commonly referred to as the Tweens), e.g., polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol); (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants can be used herein.

Mixtures of surfactants used include, e.g. Tween 80/Span 85 mixtures. A combination of a polyoxyethylene sorbitan ester and an octoxynol can also be suitable. Another combination can comprise laureth 9 plus a polyoxyethylene sorbitan ester and/or an octoxynol.

In some cases, the amounts of surfactants (% by weight) include: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Carriers and Excipients

In some instances, a vaccine includes carriers and excipients (including but not limited to buffers, carbohydrates, mannitol, proteins, polypeptides, or amino acids such as glycine, antioxidants, bacteriostats, chelating agents, suspending agents, thickening agents, and/or preservatives), water, oils including those of petroleum, animal, vegetable or synthetic origin, such as peanut oil, soybean oil, mineral oil, sesame oil, and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another instances, the pharmaceutical preparation is substantially free of preservatives. In other instances, the pharmaceutical preparation can contain at least one preservative. General methodology on pharmaceutical dosage forms is found in Ansel et al., Pharmaceutical Dosage Forms and Drug Delivery Systems (Lippencott Williams &

Wilkins, Baltimore Md. (1999)). It will be recognized that, while any suitable carrier known to those of ordinary skill in the art can be employed to administer the pharmaceutical compositions described herein, the type of carrier will vary depending on the mode of administration.

In some instances, a pharmaceutical composition of the vaccine is encapsulated within liposomes using well-known technology. Biodegradable microspheres can also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

In some cases, the pharmaceutical composition is administered in liposomes or microspheres (or microparticles). Methods for preparing liposomes and microspheres for administration to a patient are well known to those of skill in the art. U.S. Pat. No. 4,789,734, e.g., describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998).

In some cases, a vaccine includes preservatives such as thiomersal or 2-phenoxyethanol. In some instances, the vaccine is substantially free from (e.g. <10 µg/ml) mercurial material e.g. thiomersal-free. α-Tocopherol succinate may be used as an alternative to mercurial compounds.

For controlling the tonicity, a physiological salt such as sodium salt are optionally included in the vaccine. Other salts include potassium chloride, potassium dihydrogen phosphate, disodium phosphate, and/or magnesium chloride, or the like.

In some instances, a vaccine has an osmolality of from about 200 mOsm/kg to about 400 mOsm/kg, from about 240 to about 360 mOsm/kg, or within the range of 290-310 mOsm/kg.

In some cases, a vaccine comprises one or more buffers, such as a Tris buffer; a borate buffer; a succinate buffer; a histidine buffer (for example, with an aluminum hydroxide adjuvant); or a citrate buffer. Buffers, in some cases, are included in the 5-20 mM range.

In some cases, the pH of the vaccine is from about 5.0 to about 8.5, from about 6.0 to about 8.0, from about 6.5 to about 7.5, or from about 7.0 to about 7.8.

In some instances, a vaccine is sterile. In some cases, the vaccine is non-pyrogenic e.g. containing <1 EU (endotoxin unit, a standard measure) per dose, and can be <0.1 EU per dose.

In some instances, a vaccine includes detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide (CTAW), or sodium deoxycholate, particularly for a split or surface antigen vaccine.

The detergent can be present only at trace amounts. Thus the vaccine can include less than 1 mg/ml of each of octoxynol-10 and polysorbate 80. Other residual components in trace amounts are optionally antibiotics (e.g. neomycin, kanamycin, streptomycin, polymyxin B).

In some instances, a vaccine is formulated as a sterile solution or suspension, in suitable vehicles, well known in the art. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington "The Science and Practice of Pharmacy" ($20^{th}$ Ed., Lippincott Williams & Wilkins, Baltimore Md.).

In some instances, a vaccine is formulated with one or more pharmaceutically acceptable salts. Pharmaceutically acceptable salts can include those of the inorganic ions, such as, for example, sodium, potassium, calcium, magnesium ions, and the like. Such salts can include salts with inorganic or organic acids, such as hydrochloric acid, hydrobromic acid, phosphoric acid, nitric acid, sulfuric acid, methanesulfonic acid, p-toluenesulfonic acid, acetic acid, fumaric acid, succinic acid, lactic acid, mandelic acid, malic acid, citric acid, tartaric acid, or maleic acid. In addition, if the agent(s) contain a carboxy group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

Pharmaceutical compositions comprising an active agent such as a peptide, a nucleic acid, an antibody or fragments thereof, and/or an APC described herein, in combination with one or more adjuvants can be formulated to comprise certain molar ratios. For example, molar ratios of about 99:1 to about 1:99 of an active agent such as a peptide, a nucleic acid, an antibody or fragments thereof, and/or an APC described herein, in combination with one or more adjuvants can be used. In some instances, the range of molar ratios of an active agent such as a peptide, a nucleic acid, an antibody or fragments thereof, and/or an APC described herein, in combination with one or more adjuvants can be selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of an active agent such as a peptide, a nucleic acid, an antibody or fragments thereof, and/or an APC described herein, in combination with one or more adjuvants can be about 1:9, and in some cases can be about 1:1. The active agent such as a peptide, a nucleic acid, an antibody or fragments thereof, and/or an APC described herein, in combination with one or more adjuvants can be formulated together, in the same dosage unit e.g., in one vial, suppository, tablet, capsule, an aerosol spray; or each agent, form, and/or compound can be formulated in separate units, e.g., two vials, suppositories, tablets, two capsules, a tablet and a vial, an aerosol spray, and the like.

Treatment of a Disease or Condition by a Vaccine Derived from a Modified Membrane-Spanning Polypeptide In some embodiments, a vaccine described herein is formulated for the treatment of a disease or condition, such as cancer. In some instances, a cancer is a solid tumor or a hematologic malignancy. In some instances, a cancer is a metastatic cancer, or a relapsed or refractory cancer. In some instances, a solid tumor comprises anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

In some instances, a hematologic malignancy comprises a leukemia, a lymphoma, a myeloma, a non-Hodgkin's lymphoma, a Hodgkin's lymphoma, a T-cell malignancy, or a B-cell malignancy. In some embodiments, the T-cell malignancy is peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, a B-cell malignancy comprises chronic lymphocytic leukemia (CLL), small lymphocytic lymphoma (SLL), high risk CLL, a non-CLL/SLL lymphoma, or prolymphocytic leukemia (PLL). In some embodiments, the cancer is follicular lymphoma (FL), diffuse large B-cell lymphoma (DLBCL), mantle cell lymphoma (MCL), Waldenström's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, an antibody-based vaccine described herein is used for the treatment of a cancer. In some instances, the cancer is a solid tumor. In other instances, the cancer is a hematologic malignancy. In some instances, the cancer is a metastatic cancer, or a relapsed or refractory cancer.

In some instances, a nucleic acid-based vaccine described herein is used for the treatment of a cancer. In some instances, the cancer is a solid tumor. In other instances, the cancer is a hematologic malignancy. In some instances, the cancer is a metastatic cancer, or a relapsed or refractory cancer.

In some instances, a peptide-based vaccine described herein is used for the treatment of a cancer. In some instances, the cancer is a solid tumor. In other instances, the cancer is a hematologic malignancy. In some instances, the cancer is a metastatic cancer, or a relapsed or refractory cancer.

In some instances, a dendritic cell-based vaccine described herein is used for the treatment of a cancer. In some instances, the cancer is a solid tumor. In other instances, the cancer is a hematologic malignancy. In some instances, the cancer is a metastatic cancer, or a relapsed or refractory cancer.

In some instances, an antigen-presenting cell (APC) based vaccine described herein is used for the treatment of a cancer. In some instances, the cancer is a solid tumor. In other instances, the cancer is a hematologic malignancy. In some instances, the cancer is a metastatic cancer, or a relapsed or refractory cancer.

In some instances, a virus-based vaccine described herein is used for the treatment of a cancer. In some instances, the cancer is a solid tumor. In other instances, the cancer is a hematologic malignancy. In some instances, the cancer is a metastatic cancer, or a relapsed or refractory cancer.

Vaccine Formulations

In some embodiments, a vaccine described herein, in combination with one or more adjuvants is formulated in conventional manner using one or more physiologically acceptable carriers, comprising excipients, diluents, and/or auxiliaries, e.g., which facilitate processing of the active agents into preparations that can be administered. Proper formulation depends at least in part upon the route of administration chosen. The agents) described herein can be delivered to a patient using a number of routes or modes of administration, including oral, buccal, topical, rectal, transdermal, transmucosal, subcutaneous, intravenous, and intramuscular applications, as well as by inhalation.

In some instances, the active agents are formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, or biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

When administration is by injection, the active agent is sometimes formulated in aqueous solutions, specifically in physiologically compatible buffers such as Hanks solution, Ringer's solution, or physiological saline buffer. The solution can contain formulatory agents such as suspending, stabilizing, and/or dispersing agents. Alternatively, the active compound can be in powder form for constitution with a suitable vehicle, e.g., sterile pyrogen-free water, before use. In another embodiment, the pharmaceutical composition does not comprise an adjuvant or any other substance added to enhance the immune response stimulated by the peptide. In another embodiment, the pharmaceutical composition comprises a substance that inhibits an immune response to the peptide. Methods of formulation are known in the art, for example, as disclosed in Remington's Pharmaceutical Sciences, latest edition, Mack Publishing Co., Easton P.

For oral administration, the active agent is sometimes formulated readily by combining the active agent with pharmaceutically acceptable carriers well known in the art. Such carriers enable the agents of the invention to be formulated as tablets, including chewable tablets, pills, dragees, capsules, lozenges, hard candy, liquids, gels, syrups, slurries, powders, suspensions, elixirs, wafers, and the like, for oral ingestion by a patient to be treated. Such formulations can comprise pharmaceutically acceptable carriers including solid diluents or fillers, sterile aqueous media, and various non-toxic organic solvents. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Generally, the active agents can be included at concentration levels ranging from about 0.5%, about 5%, about 10%, about 20%, or about 30% to about 50%, about 60%, about 70%, about 80%, or about 90% by weight of the total composition of oral dosage forms, in an amount sufficient to provide a desired unit of dosage.

In some instances, the vaccine is formulated into aerosol solutions, suspensions, or dry powders. The aerosol can be administered through the respiratory system or nasal passages. For example, one skilled in the art will recognize that a composition of the present invention can be suspended or dissolved in an appropriate carrier, e.g., a pharmaceutically acceptable propellant, and administered directly into the lungs using a nasal spray or inhalant. For example, an aerosol formulation comprising a transporter, carrier, or ion channel inhibitor can be dissolved, suspended or emulsified in a propellant or a mixture of solvent and propellant, e.g., for administration as a nasal spray or inhalant, Aerosol formulations can contain any acceptable propellant under pressure, such as a cosmetically or dermatologically or pharmaceutically acceptable propellant, as conventionally used in the art.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

In some instances, an aerosol formulation for inhalations and inhalants are designed so that the agent or combination of agents is carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants can include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Halocarbon propellants are described in Johnson, U.S. Pat. No. 5,376,359, Byron et al., U.S. Pat. No. 5,190,029, and Purewal et al., U.S. Pat. No. 5,776,434. Hydrocarbon propellants useful in the invention include, for example, propane, isobutane, n-butane, pentane, isopentane, and neopentane. A blend of hydrocarbons can also be used as a propellant. Ether propellants include, for example, dimethyl ether as well as the ethers. An aerosol formulation in some instances also comprises more than one propellant. For example, the aerosol formulation can comprise more than one propellant from the same class, such as two or more fluorocarbons; or more than one, more than two, more than three propellants from different classes, such as a fluorohydrocarbon and a hydrocarbon. In some instances, vaccines are also dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

In some instances, the aerosol formulation is packaged under pressure and is formulated as an aerosol using solutions, suspensions, emulsions, powders, and semisolid preparations. For example, a solution aerosol formulation can comprise a solution of an agent of the invention such as a transporter, carrier, or ion channel inhibitor in (substantially) pure propellant or as a mixture of propellant and solvent. The solvent can be used to dissolve the agent and/or retard the evaporation of the propellant. Solvents can include, for example, water, ethanol and glycols. Any combination of suitable solvents can be used, optionally combined with preservatives, antioxidants, and/or other aerosol components.

In some instances, an aerosol formulation is a dispersion or suspension. A suspension aerosol formulation can comprise a suspension of an agent or combination of agents of the instant invention, e.g., a transporter, carrier, or ion channel inhibitor, and a dispersing agent. Dispersing agents can include, for example, sorbitan trioleate, oleyl alcohol, oleic acid, lecithin, and corn oil. A suspension aerosol formulation can also include lubricants, preservatives, antioxidant, and/or other aerosol components.

In some cases, an aerosol formulation is formulated as an emulsion. An emulsion aerosol formulation can include, for example, an alcohol such as ethanol, a surfactant, water and a propellant, as well as an agent or combination of agents of the invention, e.g., a transporter, carrier, or ion channel. The surfactant used can be nonionic, anionic, or cationic. One example of an emulsion aerosol formulation comprises, for example, ethanol, surfactant, water, and propellant. Another example of an emulsion aerosol formulation comprises, for example, vegetable oil, glyceryl monostearate and propane.

Vaccine Dosages, Routes of Administration and Therapeutic Regimens

In some instances, a vaccine is delivered via a variety of routes. Exemplary delivery routes include oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999). In some instances, the vaccine described herein is administered to muscle, or can be administered via intradermal or subcutaneous injections, or transdermally, such as by iontophoresis. In some cases, epidermal administration of the vaccine is employed.

In some instances, the vaccine is formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

In some cases, the vaccine is a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

In some instances, the vaccine includes material for a single immunization, or may include material for multiple immunizations (i.e. a 'multidose' kit). In some instances, a preservative is included in a multidose arrangement. As an alternative (or in addition) to including a preservative in multidose compositions, the compositions can be contained in a container having an aseptic adaptor for removal of material.

In some instances, the vaccine is administered in a dosage volume of about 0.5 mL, although a half dose (i.e. about 0.25 mL) can be administered to children. Sometimes the vaccine can be administered in a higher dose e.g. about 1 ml.

In some instances, the vaccine is administered as a 1, 2, 3, 4, 5, or more dose-course regimen. Sometimes, the vaccine is administered as a 2, 3, or 4 dose-course regimen. Sometimes the vaccine is administered as a 2 dose-course regimen.

In some instances, the administration of the first dose and second dose of the 2 dose-course regimen are separated by about 0 day, 1 day, 2 days, 5 days, 7 days, 14 days, 21 days, 30 days, 2 months, 4 months, 6 months, 9 months, 1 year, 1.5 years, 2 years, 3 years, 4 years, or more.

In some instances, the vaccine described herein is administered every 1, 2, 3, 4, 5, 6, 7, 8, 9, 10, or more years. Sometimes, the vaccine described herein is administered every 2, 3, 4, 5, 6, 7, or more years. Sometimes, the vaccine described herein is administered every 4, 5, 6, 7, or more years. Sometimes, the vaccine described herein is administered once.

The dosage examples are not limiting and are only used to exemplify particular dosing regiments for administering a vaccine described herein. The effective amount for use in humans can be determined from animal models. For example, a dose for humans can be formulated to achieve circulating, liver, topical, and/or gastrointestinal concentrations that have been found to be effective in animals. Based on animal data, and other types of similar data, those skilled in the art can determine the effective amounts of a vaccine composition appropriate for humans.

The effective amount when referring to an agent or combination of agents will generally mean the dose ranges, modes of administration, formulations, etc., that have been recommended or approved by any of the various regulatory or advisory organizations in the medical or pharmaceutical arts (e.g., FDA, AMA) or by the manufacturer or supplier.

In some instances, the vaccine can be administered before, during, or after the onset of a symptom associated with a disease or condition (e.g., a cancer). Exemplary symptoms can include fever, cough, sore throat, runny and/or stuffy nose, headaches, chills, fatigue, nausea, vomiting, diarrhea, pain, or a combination thereof. In some instances, the vaccine is administered for treatment of a cancer. In some cases, the vaccine is administered for prevention, such as a prophylactic treatment of a cancer. In some cases, the vaccine is administered to illicit an immune response from a patient.

In some aspects, the vaccine and kit described herein are stored at between 2° C. and 8° C. In some instances, the vaccine is not stored frozen. In some instances, the vaccine is stored in temperatures of such as at −20° C. or −80° C. In some instances, the vaccine is stored away from sunlight.

Kits/Article of Manufacture

Disclosed herein, in certain embodiments, are kits and articles of manufacture for use with one or more methods and platform described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and optionally intended mode of administration and treatment.

For example, the container(s) include a purified modified multispanning membrane polypeptide (e.g., an ion channel polypeptide or a GPCR), a modified multispanning membrane polypeptide (e.g., an ion channel polypeptide or a GPCR) construct, an antibody against a modified multispanning membrane polypeptide (e.g., an ion channel polypeptide or a GPCR), or a vaccine based on a modified multispanning membrane polypeptide (e.g., an ion channel polypeptide or a GPCR) described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers, or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, a vaccine based on a modified multispanning membrane polypeptide (e.g., an ion channel polypeptide or a GPCR) described herein is presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Certain Terminology

Unless defined otherwise, all technical and scientific terms used herein have the same meaning as is commonly understood by one of skill in the art to which the claimed subject matter belongs. It is to be understood that the general description and the detailed description are exemplary and explanatory only and are not restrictive of any subject matter claimed. In this application, the use of the singular includes the plural unless specifically stated otherwise. It is noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that is typically expected to be within experimental error, e.g., +5%, +10%, or +15%.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the term "operably linked" means that, for example, a first nucleic acid molecule is linked in-frame (or in reading frame) with a second nucleic acid molecule and that both the first nucleic acid molecule and the second nucleic acid molecule encode a first polypeptide and a second polypeptide, respectively, upon translation. In some instances, "operably linked" further comprises direct linking or indirect linking, for example, the first nucleic acid molecule is directly linked to the second nucleic acid molecule or indirect linked through a linker sequence. In some instances, in the context of a first selection marker gene and a second selection marker gene, a first selection marker gene is operably linked (or linked in-frame) to the encoded C-terminus of a polynucleotide described herein. In some cases, a second selection marker is operably linked (or linked in-frame) to the encoded N-terminus of a polynucleotide described herein. In some instances, the first selection marker gene and/or the second selection marker gene is further either directly linked to a polynucleotide described herein or indirectly linked to a polynucleotide described herein via a linker sequence. In some cases, a linker sequence encodes a linker polypeptide of about 1 to about 60 amino acid residues in length, e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60 amino acid residues.

As used herein, the term "production vector" means an expression vector utilized for production of a protein of interest. For example in the context of a modified multispanning membrane polypeptide described herein, a production vector is an expression vector used for protein production of a modified multispanning membrane polypeptide. In some instances, the production vector is a bacterial (e.g. *E. coli*) expression vector, an insect expression vector, a yeast expression vector, an algae expression vector, or a mammalian expression vector. In some instances, the production vector does not comprise a selection marker gene as described herein operably linked to a gene encoding a modified multispanning membrane polypeptide (e.g., either directly linked or indirectly linked to the N-terminus and/or the C-terminus) and encoding a modified multispanning membrane polypeptide-selection marker polypeptide fusion protein. In some cases, the production vector does not encode a modified multispanning membrane polypeptide of Formulas I-IV.

EXAMPLES

These examples are provided for illustrative purposes only and not to limit the scope of the claims provided herein.

Example 1—Library Generation Phase

Random mutagenesis, optionally coupled with DNA shuffling, leverage a full range of combinatorial amino acid replacements in multiple positions simultaneously. Error prone PCR was used to generate a library (first level library) of genes where 2-8 amino acid residues were randomly mutated after translation per each 1 Kb of DNA coding region (fairly homogeneous frequency of mutation). Optionally, DNA shuffling (StEP, Staggered Extention PCR) was subsequently used to generate a second library (second level) with genes randomly mutated in about 1 to 15 different amino acids per each 1 Kb of DNA coding region.

These domains were all separated by various small oligopeptide linkers in order to allow functional folding of the various components of the construct. The construct was permanently transcribed in the selection host *E. coli* using constitutive promoters (e.g. Plac) or inducible promoters (e.g. araBAD, T7) with the addition of chemical inducers (e.g. arabinose, IPTG).

Example 2—Construct Design for Multispanning Membrane Polypeptide Variant Selection The mutated genes were inserted in a pre-formed construct (plasmid form) containing:
  a signal sequence,
  a first selection marker protein/enzyme (e.g. kanamycin resistance gene) on its C-terminal side, and
  maltose binding protein (MBP) or a second selection marker protein/enzyme (e.g. beta-lactamase gene) on the receptor's N-terminal side.

Example 3—Selection Phase

The construct library containing modified genes was then used to transform *E. coli* strains (e.g. BL21 or DH10beta). Growth was tested on LB medium with varying concentrations of kanamycin (MIC for untransformed cells was approximately 10 mg/L), both in liquid cultures and agar plates.

An N-terminal truncation (aa 43-424) of the wild-type Neurotensin receptor 1 from rat (NTSR1, UniProt P20789) was used as a control system.

About 25 constructs were generated with wild-type NTSR1 consisting of combinations of:
- 3 different signal sequences (gIIIss, DsbAss, MBPss);
- 2 fusion partners (TrxA, MBP);
- several oligopeptide linkers; and
- antibiotic resistance enzymes (NPTII for kanamycin resistance, AAC(3)-1 for gentamicin resistance, TEM-1 β-lactamase for carbenicillin resistance).

Apparent MIC for both antibiotics tested (carbenicillin and gentamicin) increased considerably when *E. coli* expressed certain constructs containing NTSR1 (>50 mg/L kanamycin, >75 mg/L carbenicillin).

MIC for both antibiotics tested (carbenicillin and kanamycin) also increased when *E. coli* contained a plasmid encoding the wild-type membrane-spanning protein receptor GPR55 from human (UniProt Q9Y2T6) (approximately 25 mg/L kanamycin, 40 mg/L carbenicillin).

Libraries of mutated GPR55 genes were created containing between about 3 and 15 random mutations (residue) per gene. Selection of plasmids containing enhanced receptor mutants was performed at 50 mg/L kanamycin.

Transformation of *E. coli* strains with these libraries resulted in the isolation of mutated GPR55 clones that could confer resistance to high concentrations of kanamycin (>50 mg/L) or carbenicillin (>80 mg/L).

Figure 2:
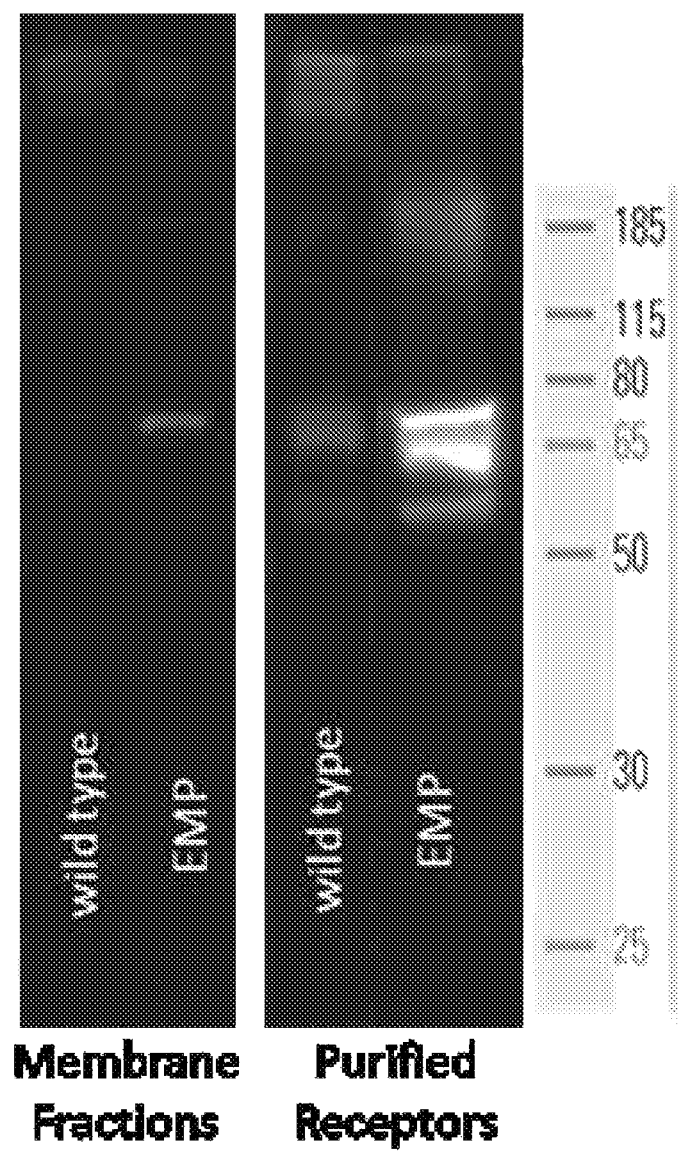
FIG. 2 shows a Western blot of a wild-type membrane receptor and its enhanced modified multispanning membrane polypeptide (also referred to herein as "Enabled Membrane Protein" or "EMP"). Staining of the FLAG-tagged fusion modified multispanning membrane polypeptide was carried out using an anti-FLAG HRP-conjugated antibody. The protein marker indicates molecular weights in KDa.

Mutated clones were transferred to mammalian expression hosts, including HEK293T by transfection using the pcDNA3.1 vector. Expression was observed to increase by >5-fold over constructs containing wild-type GPR55, as judged by electrophoretic (FIG. 2) and fSEC techniques.

Figure 3:
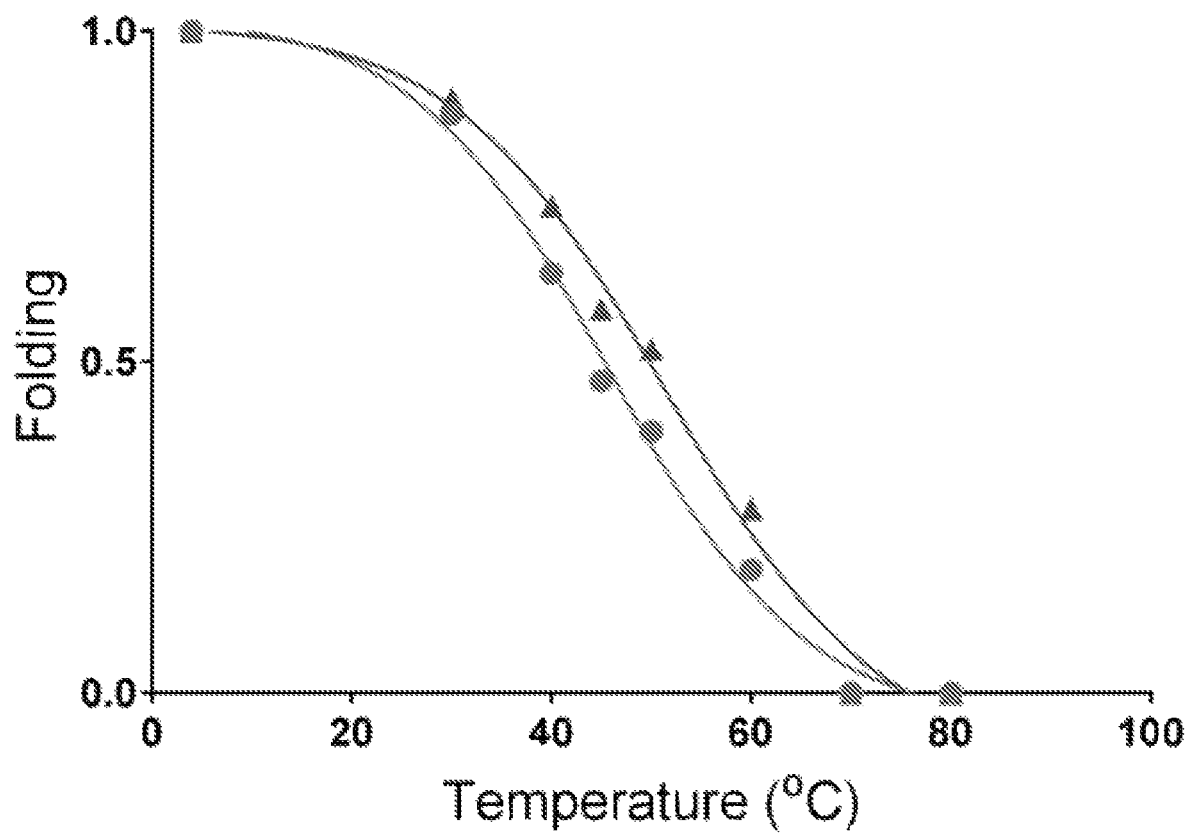
FIG. 3 illustrates thermal unfolding curves measured using fluorescent size exclusion chromatography (fSEC) on purified membrane receptors in a protein-detergent complex after one round of mutagenesis. The wild-type receptor is shown in closed circles, whereas a stabilized mutant is shown in triangles.

Mutated clones were expressed and purified; the resulting protein-detergent complex samples demonstrated an increase in thermostability of up to 7° C. over wild-type after one round of mutagenesis (as judged by fSEC (FIG. 3) and fluorimetric techniques).

Figure 4:
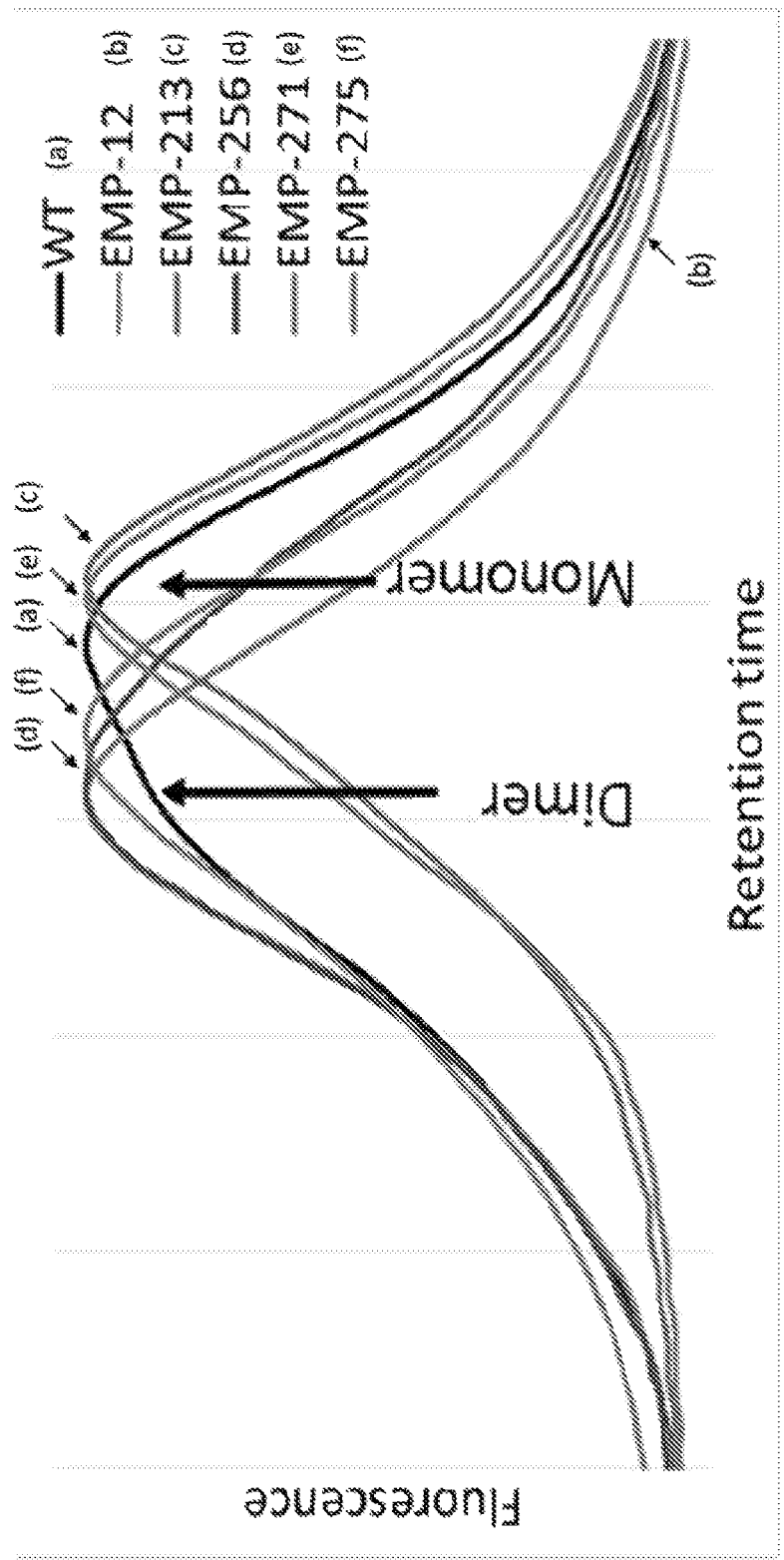
FIG. 4 illustrates normalized fSEC peaks of a purified wild-type (black trace) membrane receptor and five mutant multispanning membrane polypeptides. The peaks corresponding to monomer and dimer of the analyzed multispanning membrane polypeptides (estimated oligomeric state of the analyzed samples) are indicated with a black arrow.

Mutated clones also demonstrated a more homogeneous oligomeric state compared to wild type when receptor samples were purified in ligand free form (FIG. 4).

When using hyperthermophilic species (e.g. *Thermus thermophilus*) as a selection host, the protein melting temperature (in the thermal unfolding format) of the identified mutants is expected to be superior when compared to a selection process performed in *E. coli*. (i.e., more than 10° C. higher than wild-type).

Example 4—Construct Design for Protein Production

A set of constructs are designed to generate a modified multispanning membrane protein that is expressed, extracted from the cellular membrane, isolated and purified to homogeneity and is suitable for compound screening, antibody selection, or crystallization. In some instances, a modified multispanning membrane protein comprises N-terminal and C-terminal truncations, surface mutations, and other modifications including internal truncations and/or polypeptide insertions.

These constructs are engineered with a C-terminal or N-terminal histidine tag for purification and contain a tobacco etch virus protease or Prescission protease cleavage sites so that the tag or fusion proteins can be cleaved after purification.

The cDNA for the multispanning membrane protein is cloned into vectors suitable for expression in a selected host amenable for large scale expression and purification (e.g. bacterial cells, or eukaryotic cells. Mammalian cells or insect cells are particularly suited for human multispanning membrane protein).

Example 5—Pharmacology (Cell-Based Assays)

The function of a multi-spanning membrane protein prior to use in drug compound screening or crystallization is assessed, as it provides evidence that the protein is folded in a biologically relevant form. Receptor function is determined by measuring its response to small molecule chemical compounds, peptides or protein binders with agonistic or antagonistic properties (ligands). This is done by expressing the membrane protein in an in vitro cultured eukaryotic cells system such as HEK293 or COS. A functional response to added modulator is assessed through the activation of one or more direct effector proteins that leads to the subsequent production of a measurable metabolite, such as the accumulation or decrease in the amounts of cyclic adenosine monophosphate (cAMP) or calcium ions ($Ca^{2+}$). The effect of a modified multispanning membrane protein such as an Ion channel polypeptide on the cell physiology is measured by, for example, changes in the electrochemical potential gradient.

Activation of modified multispanning membrane proteins such as GPCRs by an added ligand can trigger specific G-protein signaling pathways that lead to the increased or decreased production or cAMP. Activation of the GPCR by an agonist ligand can lead to an increase in cAMP levels which is used to determine an effective concentration necessary to achieve a 50% response known as the $EC_{50}$. An antagonist ligand may in turn inhibit the production cAMP, indicating a competition with the agonist ligand signaling, which is expressed as the 50% inhibitory concentration ($IC_{50}$). $EC_{50}$ and $IC_{50}$ values are used to compare relative efficacies of ligands with agonist or antagonist properties.

Assessment of pharmacologic function of modified multispanning membrane proteins is performed through the measurement of intracellular $Ca^{2+}$ levels in response to the presence of known agonists. Mammalian cell lines, either stably or transiently expressing GPCRs or ion channel with significant $Ca^{2+}$ permeability, are pre-loaded with dyes that are cell permeable and fluoresce in the response to intracellular $Ca^{2+}$. Following stimulation with known ligands, fluorescence is measured via plate readers or fluorescent imaging plate readers or fluorescence-activated cell sorting (FACS)-based Ca++ mobilization detection technologies.

Changes in membrane potential in response to known ligands is also measured in mammalian cell lines, either stably or transiently expressing ion channels, using dyes that increase in fluorescent signal as they follow positively charged ions inside the cell, and conversely decrease in fluorescent signal as they follow positively charged ions outside the cell.

Example 6—Sample Purification and QC

Sample Purification

Figure 5A:
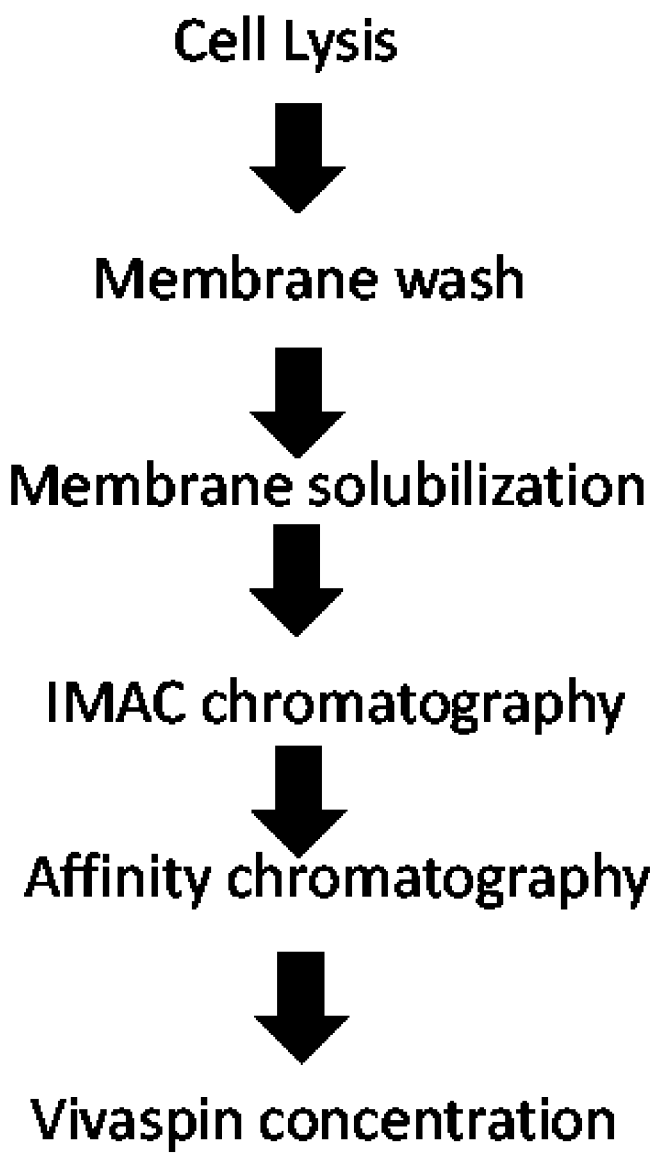
FIG. 5A illustrates a schematic representation of the sample purification steps.

Multispanning membrane proteins (also referred to herein as "Enabled Membrane Protein" or "EMP") were purified using detergents and with or without ligands (compounds, peptides, or antibodies) using chromatography methods. Sample was concentrated using Vivascience® spin columns with a molecular weight cut-off of 100KDa. A schematic representation of the sample purification steps is illustrated in FIG. 5A.

Sample QC

Figure 5B:
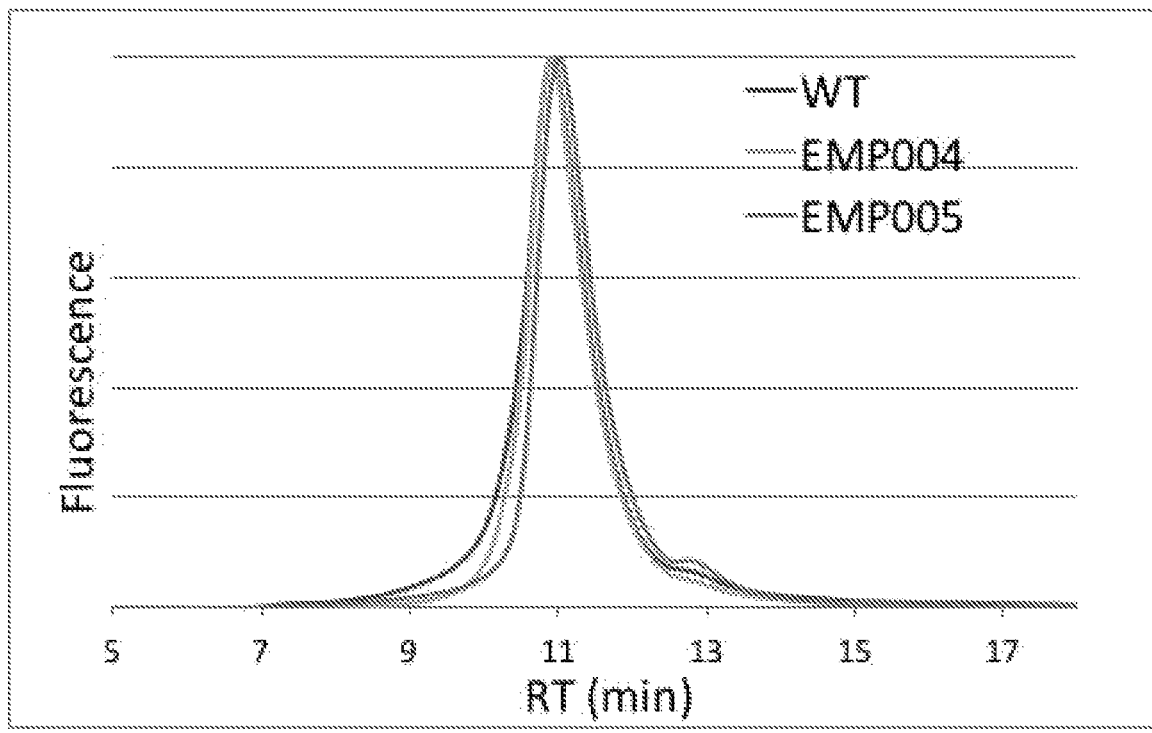
FIG. 5B shows sample homogeneity using HPLC profiles of GPCR samples (WT and EMPs 004 and 005) after IMAC purification step.
Figure 5C:
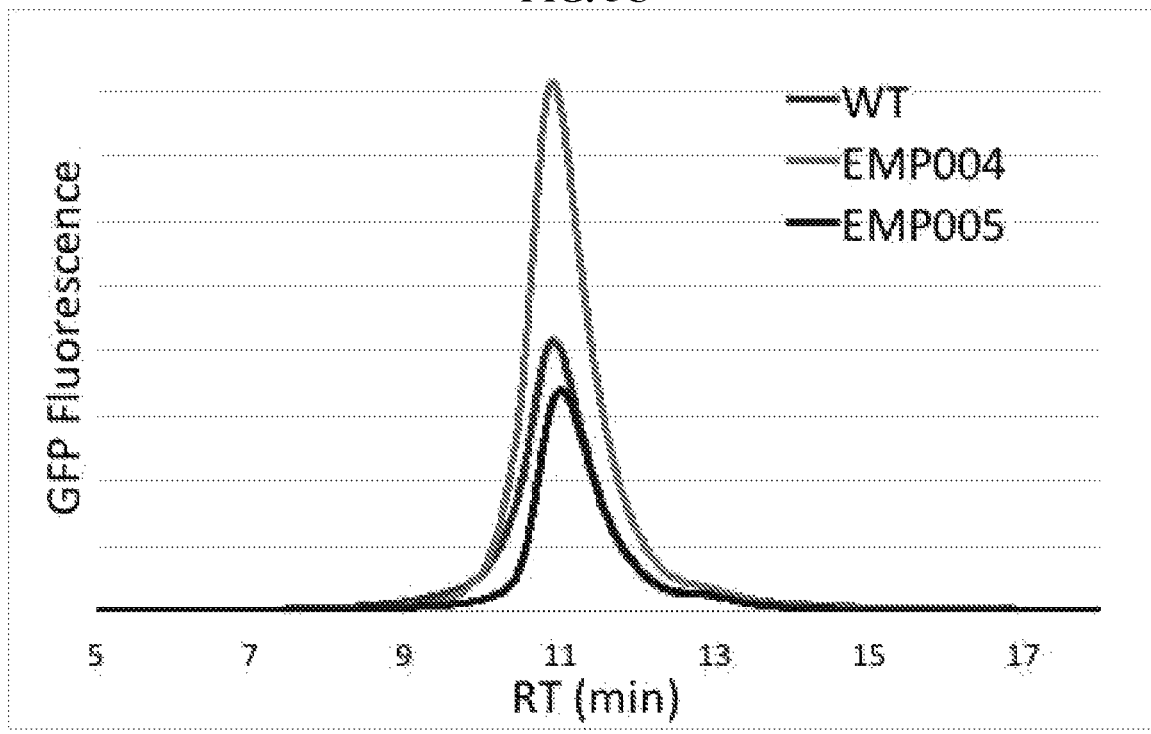
FIG. 5C compares the yields of the same samples as shown in FIG. 5B, i.e. WT and EMPs 004 and 005.
Figure 5D:
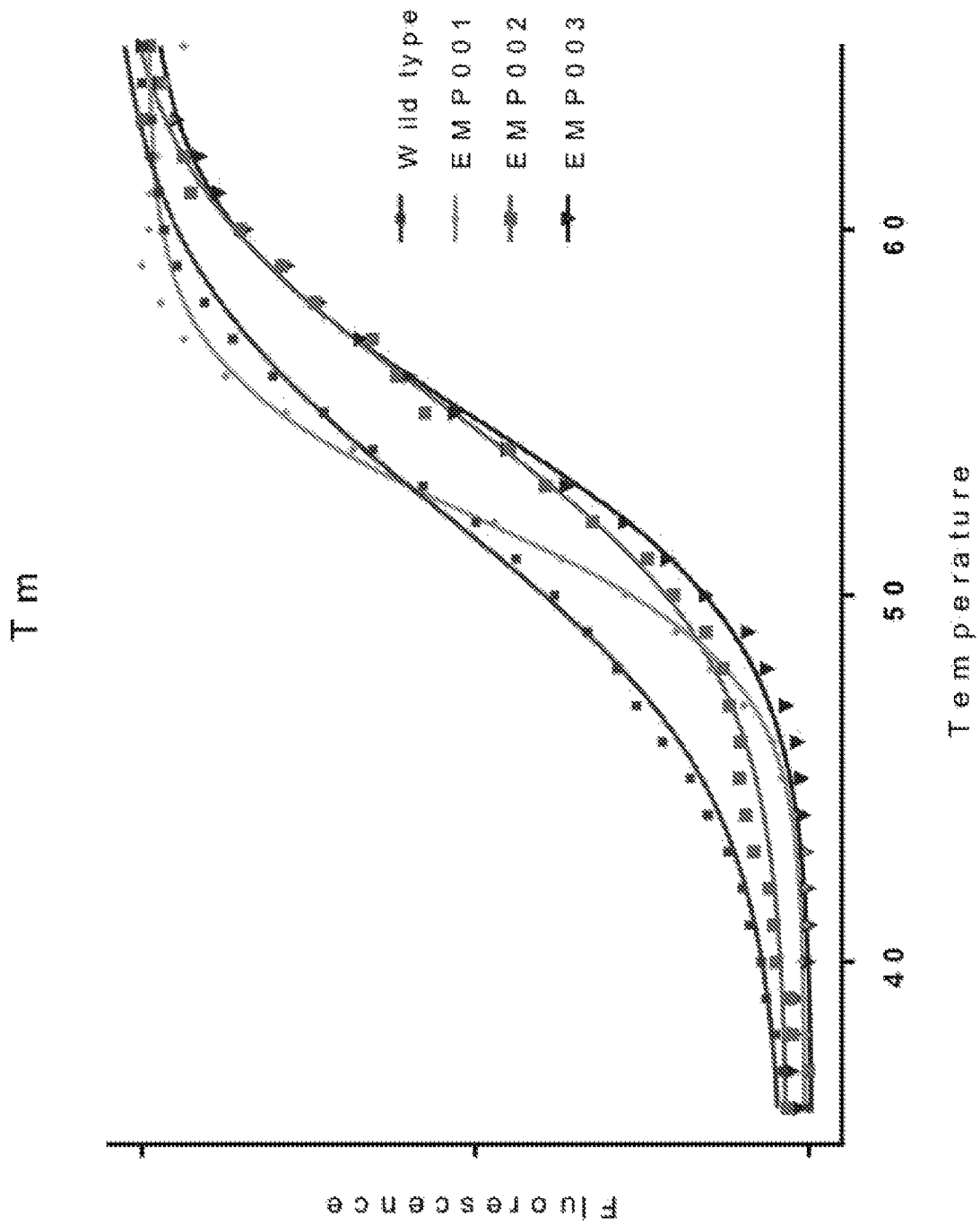
FIG. 5D illustrates normalized melting profiles of GPCR samples (WT and EMPs 001, 002 and 003) obtained using CPM assay in high salt buffer conditions.

Purification yield, homogeneity, oligomeric state, and stability of the multispanning membrane polypeptide were verified and compared to the wild-type multispanning membrane protein as assessed by analytical size exclusion chromatography (FIG. 5B and FIG. 5C) in the form of protein-detergent complex. Purity was assessed using SDS-PAGE in combination with Coomassie staining or other stainings. Protein stability was assessed by using thermal fluorimetric assays, for example, a CPM assay as shown in FIG. 5D.

EMPs sample quality and yield were assessed by analytical size exclusion chromatography in the form of protein-detergent complex. Protein stability was assessed using a CPM assay. All EMPs were generated as fusion proteins comprising an eGFP portion.

Example 7—EMPs Binding and Kinetic Data Using Surface Plasmon Resonance (SPR)

Binding Data

Figure 6A:
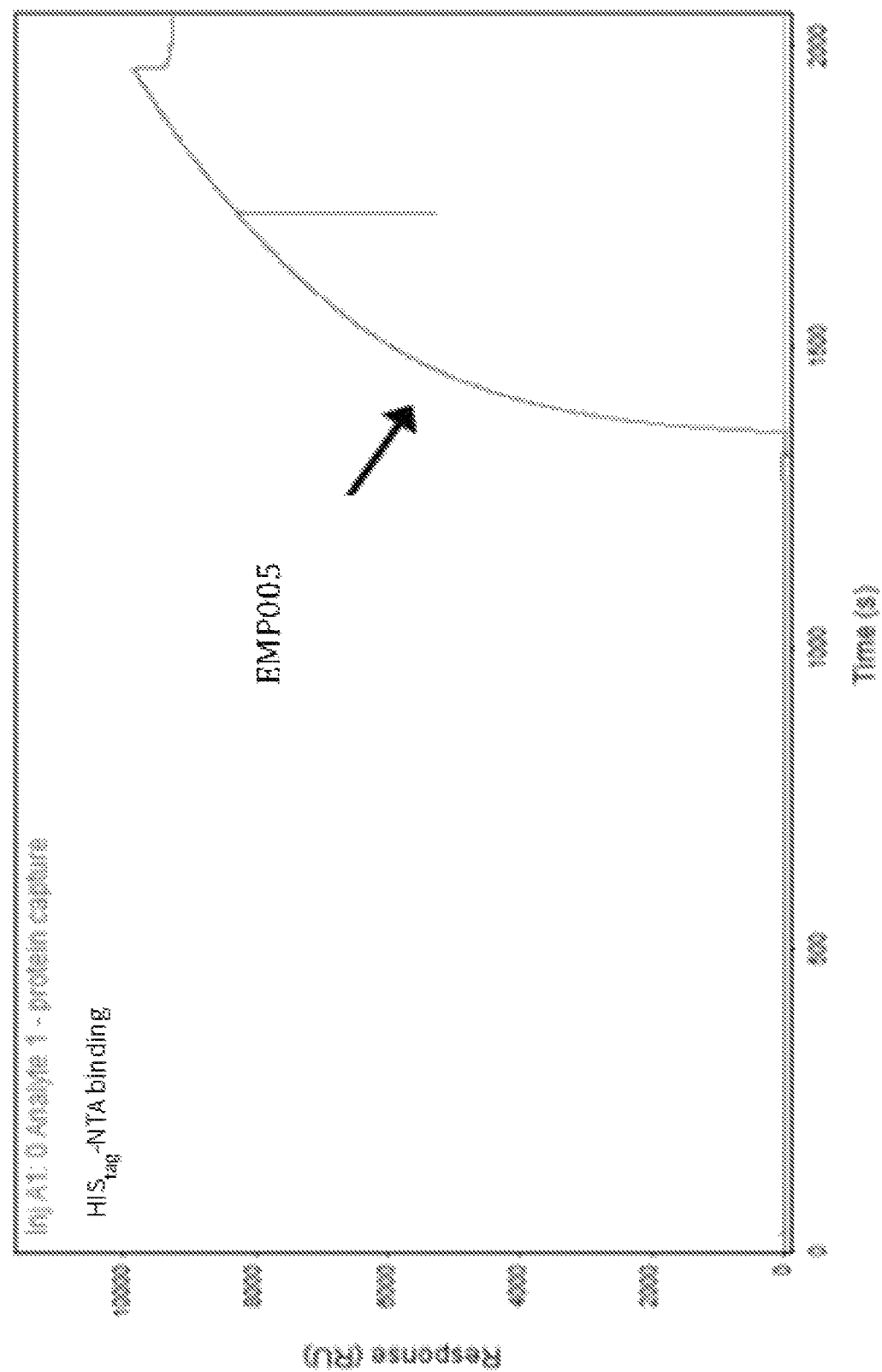
FIG. 6A and FIG. 6B show binding data using SPR. Both sensorgrams illustrate binding properties of the EMP005 sample.
Figure 6B:
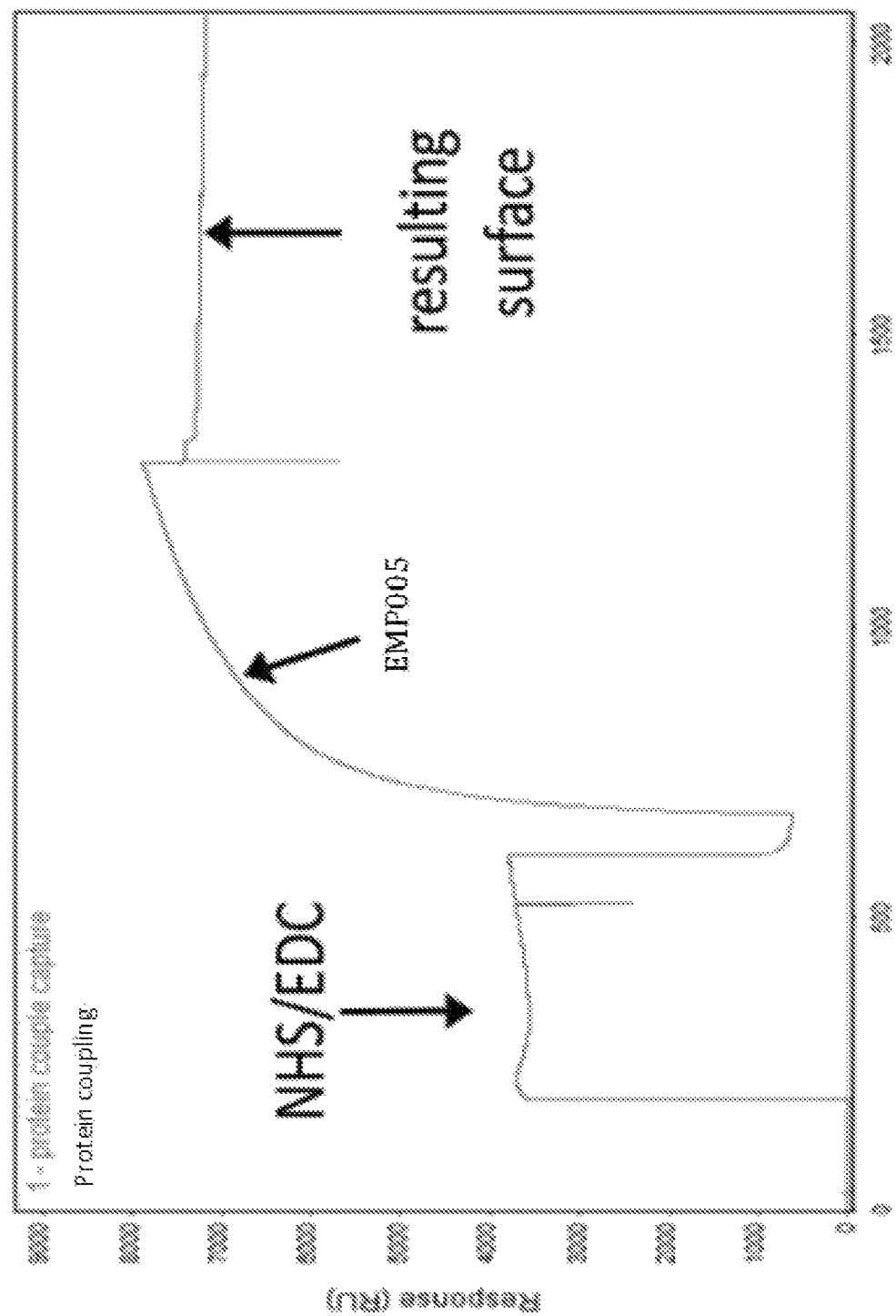

Surface Plasmon Resonance (SPR) was used for monitoring the affinity of bi-molecular interactions (analysis of association and dissociation rate constants, modeling of bi-molecular interaction kinetics, equilibrium binding analysis and ligand specificity studies). Illustrative EMP-005 was coupled to the Biacore chip using NHS/EDC couplers (FIG. 6A). The HIS-tagged EMP-005 was bound to a NTA chip (FIG. 6B). Both sensorgrams show optimal binding properties of the EMP-005 sample.

Kinetics Data

Figure 6C:
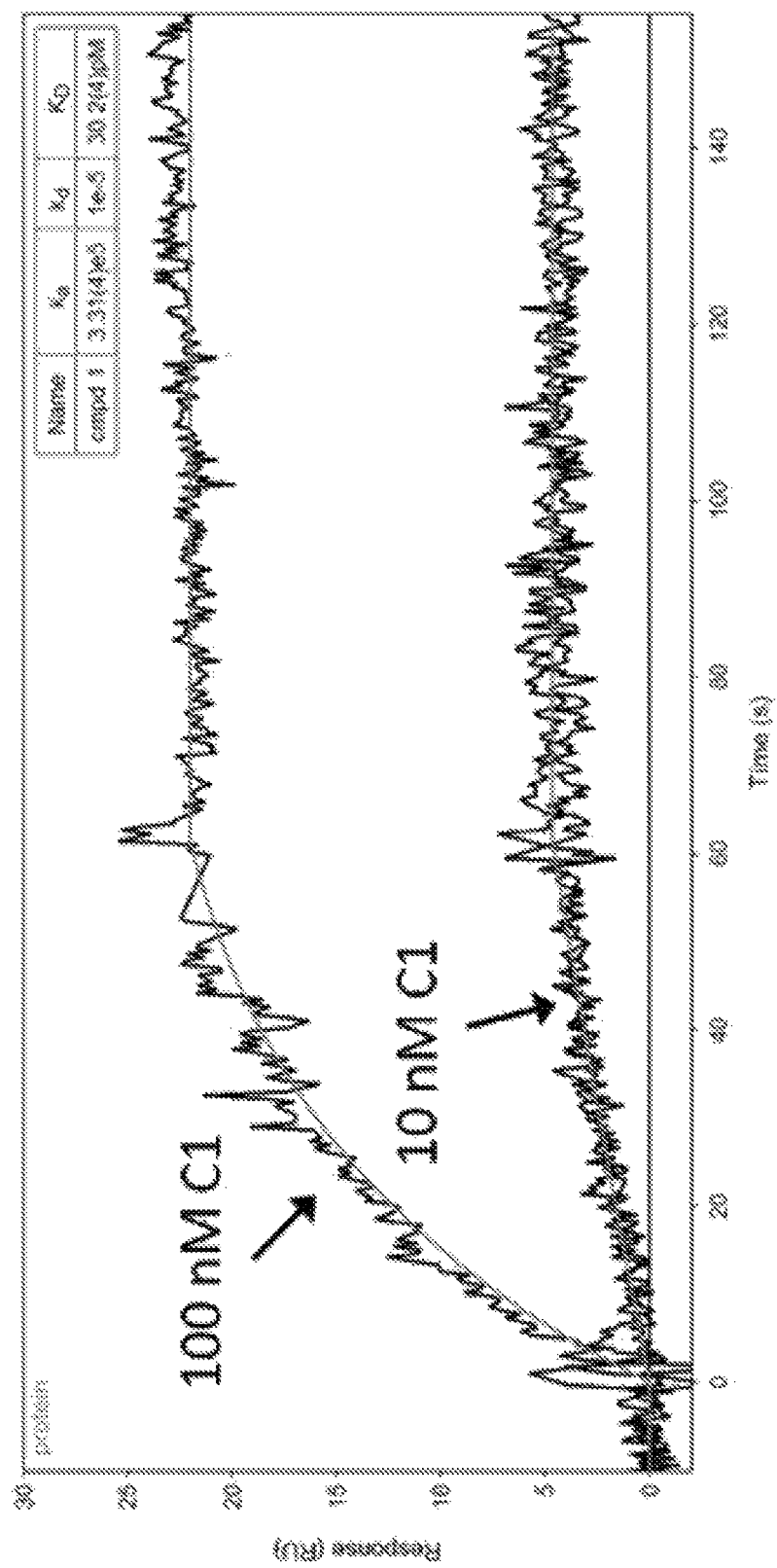
FIG. 6C show kinetics data using a small molecule compound to determine EMP005 quality and binding kinetics.

Two small molecule compounds (~450 Da) were used to determine EMP-005 quality and binding kinetics. Sensor surfaces were of sufficient densities to observe and measure the binding kinetic (Ka, Kd, KD) of both small molecule compounds (FIG. 6C). Demonstrative data for only one of the two compounds are shown in FIG. 6C. Chemically-coupled receptor was equally functional to the non-covalently captured receptor indicating that the protein tolerates coupling chemistry.

Example 8—Immunization with GPR55 EMPs™ Clone 012 Using Nanotechnology-Based DNA Delivery System Genetic Immunization and Boosting with Protein In some embodiments, EMPs™ enables generation of antibodies against wild-type or endogenous GPCR targets. Immunogenicity of GPR55 EMPs™ was tested in mice using in-vivo DNA immunization followed by a protein boost with purified EMP™ protein.

The genetic immunization work was performed using NanoTaxi® at In-Cell-Art (Nantes, France). NanoTaxi® is a DNA delivery system optimized for genetic immunization where the delivered genetic material is formulated with a mixture of different chemical families of lipids and polymers.

The cDNA corresponding to the EMP012 of the GPR55 receptor was cloned into a pCMV-based vector and cell surface expression was confirmed via transient transfection of HEK293T and HeLa cells prior to immunogen administration.

C57BL6 mice were immunized with 50 μg EMP012 cDNA construct formulated into the NanoTaxi® for the primary challenge, followed by 2 boosts of 50 μg using the same NanoTaxi®-based formulation at two-weekly intervals, followed by 1 boost using 50 μg purified EMP012 protein in IFA adjuvant. In some instances, boosting was carried out for the in-vivo affinity maturation by somatic hypermutation of the primary antibody response. The level of immune response was assessed at regular intervals by FACS analysis using Hela cells transfected with an unrelated GPCR (left panel) or WT-GPR55 (right panel) (FIG. 7).

Figure 7:
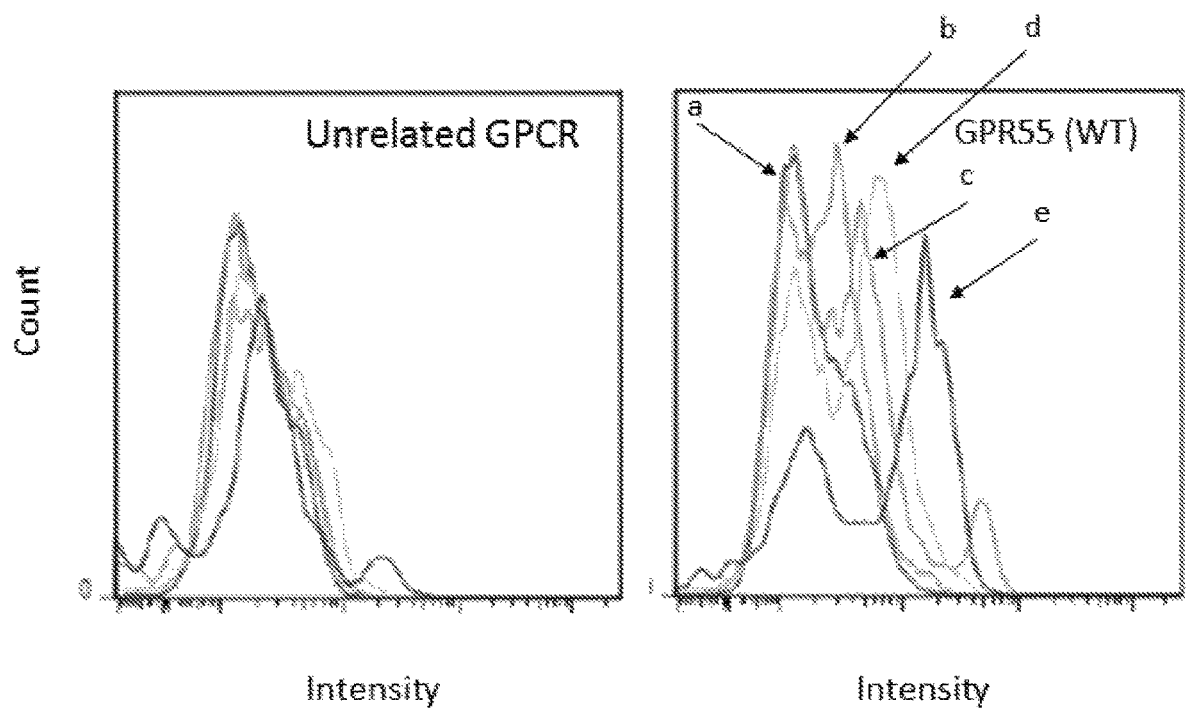
FIG. 7 illustrates FACS data of fluorescently-labeled polyclonal titers obtained from C57BL6 mice immunized with GPR55 EMP-012 DNA and purified protein against HeLa cells transfected with WT receptor. Right panel, as indicated by arrows shows: negative control (a), 3 weeks after DNA immunization (b), DNA 1st boosting (c), DNA 2nd boosting (d), purified protein boosting (e). The immunization work was performed using NanoTaxi® at In-Cell-Art (Nantes, France). Data shown are from two representative animals. FACS analysis of sera from animals immunized with GPR55 EMP-012 using Hela cells transfected with an unrelated GPCR (left panel) or WT-GPR55 (right panel).

EMP012 of the GPR55 receptor produced a robust and specific immune response against the WT-GPR55 as shown by the polyclonal antibodies specifically recognizing the wild-type GPR55 transfected HEK293 cells by FACS analysis (FIG. 7).

The sequences of the wild-type GPR55 and GPR55-EMP-012 are illustrated in FIG. 9 and FIG. 10, respectively.

Figure 8:
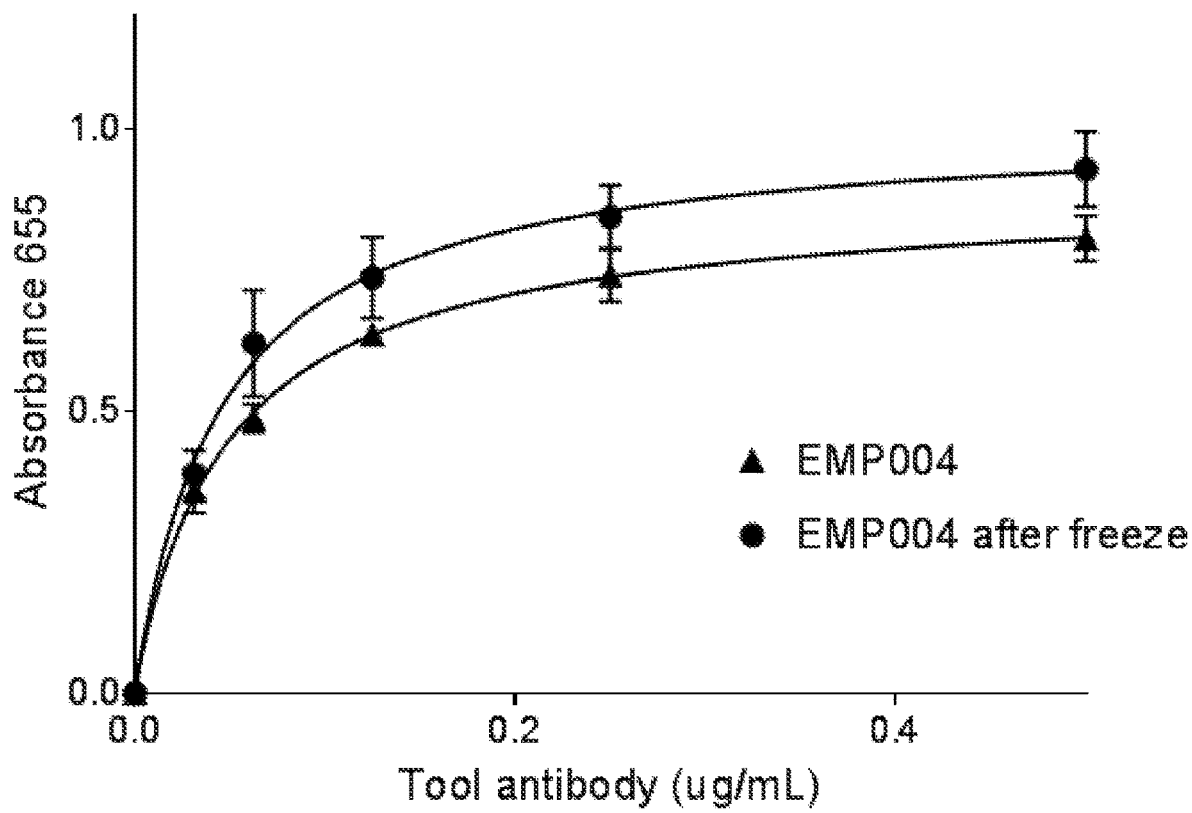
FIG. 8 illustrates purified chemokine receptor EMP004 used to test binding of an antibody specific for the WT chemokine receptor in an ELISA format. Two types of EMP receptors capture were tested: before (▲) and after a freeze thaw (●) event and they show identical signal. EMP004 purified receptor was captured using a HIS-tag.

Example 9—Immobilized EMP™ Binds Antibody Specific for WT Receptor in an ELISA Format Purified chemokine receptor (EMP™) was used to test binding of an antibody specific for WT receptor in an ELISA format. Binding of the antibody was measured before and after a freeze/thaw event and both gave an identical, excellent fluorescence signals when using fluorescently labeled antibody (FIG. 8).

Example 10—Pharmacology (Protein-Based Assays)

The binding pharmacology of multi spanning membrane proteins is assessed at the protein level by methods that directly or indirectly monitor the binding of agonistic or antagonistic ligands (small molecules, peptides, or proteins) to the expressed modified multispanning membrane protein. Preparations of cellular membranes purified from eukaryotic or prokaryotic hosts expressing the multispanning membrane protein of interest are isolated and used in a binding assay format where membranes containing the modified multispanning membrane protein of interest are incubated with a radiolabeled compound and the residually bound labeled compound is measured after thorough washing of the samples to remove excess label. Measurement of the radioactivity of the residual bound label is measured by a scintillation counter.

Binding of small molecule compounds, peptides and proteins to detergent solubilized and purified modified multispanning membrane protein is determined using the Scintillation Proximity Assay. Modified multispanning membrane protein expressed in prokaryotic or eukaryotic hosts are extracted from cellular membranes using detergents and the modified multispanning membrane protein is then purified and attached to Scintillation Proximity Beads. Radiolabeled ligands are incubated with the beads and subsequently they are washed to remove unbound ligand and the signal is read on a scintillation counter.

Example 11—Multiple Rounds of Mutagenesis

The identified modified multispanning membrane protein-encoding genes undergo a subsequent round of mutagenesis in order to identify additional mutations that confer additional benefit to the physicochemical properties of the variant multispanning membrane protein.

A number of identified modified multispanning membrane protein-encoding genes are mixed and undergo DNA shuffling and selection in order to identify cooperative mutations that were previously identified but present in different modified multispanning membrane protein genes. These cooperative mutations confer additional benefit to the physicochemical properties of the variant multispanning membrane protein.

Unnecessary mutations are eliminated from an identified modified multispanning membrane protein that contains numerous mutations by performing DNA shuffling using a mix of the modified multispanning membrane protein's gene and the wild-type gene. The selection host is again transformed with this product and a last selection round is performed in order to identify the minimal mutation set capable of maintaining the original modified multispanning membrane protein's physicochemical properties.

Example 12—Crystallization and Structure Determination

For crystallization trials, purified and concentrated samples are mixed with crystallant buffers and incubated in vapor diffusion conditions at certain temperatures. Alternatively, the protein sample is mixed with lipids in order to form lipidic cubic phases and later dispensed to a sandwich glass plate where the LCP comes into contact with the crystallant buffer prior to incubation at certain temperatures.

Crystals are harvested using a nylon loop and in the case of vapor diffusion crystallization method, the crystals are transferred and soaked with mother liquor containing cryoprotectant and flash frozen in liquid nitrogen. Alternatively, crystals are harvested from the LCP matrix and directly flash frozen in liquid nitrogen.

Datasets are collected on a synchrotron beamline and data are processed using crystallographic software, as is model building and refinement. The structure is solved by molecular replacement using atomic coordinates from known and structurally similar membrane proteins as search models obtained, for example, from the RCSB Protein Data Bank (PDB).

Example 13—Additional Immunization Methods with Modified Multispanning Membrane Protein Genetic Immunization and Boosting with Protein.

The cDNA encoding for the corresponding modified multispanning membrane protein is cloned into a specialized genetic immunization vector and cell surface expression is confirmed via transient transfection of HEK293, HEK293T, Cos-7, or HeLa cells prior to intradermal administration via the Gene Gun or others routes of immunization using other DNA delivery systems. The immunizations are conducted by a contract research organization, using their proprietary immunization and screening vectors or internally developed genetic immunization vectors.

Immunologically relevant T-helper (Th) epitopes are included in the immunization vector sequence in order to optimize the procedure for mouse immunization. In addition, immunization and screening vectors are engineered to contain detection tags thereby enabling discrimination between successful expression of immunization and expression constructs, for example, by fluorescence-activated cell sorting (FACS) analysis of sera on whole cells.

Different species including Balb-c mice and Wistar rats are immunized with 50-100 µg of multispanning membrane polypeptide cDNA construct for the primary challenge, followed by 3-6 boosts of 50-100 µm cDNA of the same multispanning membrane polypeptide at two-weekly intervals, followed by a further 1-3 immunization boosts using 50 µg purified multispanning membrane polypeptide.

Boosting immunization is required for the in vivo affinity maturation by somatic hypermutation of the primary antibody response. The level of immune response is assessed at regular intervals by FACS analysis and ELISA.

Evaluation of Sera Titer in Immune Response by FACS.

Pre-immune sera samples from mice, rats, or rabbits are compared with interim bleeds to monitor the elicited immune response in immunized animals on modified multispanning membrane protein expressing cells. Specificity of the immune response is monitored observing a significant difference in the immune response in the immunized cohorts with the modified multispanning membrane protein expressing cells vs. cells transfected with an irrelevant cDNA and untransfected cells using FACS analysis.

The mean fluorescence intensity (MFI) is plotted as a bar chart for each sera sample with the histogram profiles for the mice or rat sera sample. This demonstrates that the immune response produced a specific antibody response.

Evaluation of Sera Titers in Immune Response by ELISA.

His-tagged modified multispanning membrane proteins are immobilized on a 96-well nickel chelate plate and sera samples diluted for analysis to quantify and evaluate binding to multispanning membrane polypeptide and its WT counterpart. In mice, boosting with modified multispanning membrane protein maintains titer at the same level or increases titer.

Immunofluorescence.

The immunofluorescence data is used to demonstrate the expression and subcellular localization of the modified multispanning membrane protein in comparison to that observed with the correspondent wild-type receptor. Host cells (e.g. HEK293, HEK293T, Cos-7, or HeLa) are transiently or stably transfected with either modified multispanning membrane protein or corresponding WT encoding gene. Mouse and rat sera samples are incubated with cells expressing modified multispanning membrane protein, WT and untransfected cells and bound sera is detected using antimouse Alexa Fluor 488 and anti-rat Alexa Fluor 488, respectively.

Example 14—Modified Multispanning Membrane Protein in an Agonist or Antagonist Conformation Genetic Immunization The encoding DNA sequence of modified multispanning membrane protein selected in-vivo to retain an agonist or antagonist conformation is cloned into a genetic immunization vector and cell surface expression is confirmed via transient or stable transfection of HEK293, Cos-7, HeLa, or HEK293T cells prior to intradermal administration for example using the Gene Gun approach. Balb-c or C57Bl6 mice are immunized with 50-100 µg multispanning membrane polypeptide cDNA construct or with the WT cDNA for the primary challenge, followed by 3-6 boosts of 50-100 µg cDNA at two-weekly intervals. The level of immune response is assessed at regular intervals by FACS analysis.

Confirmation of Cell Surface Expression in HEK293, Cos-7, HeLa, or HEK293T Cells.

Modified multispanning membrane protein expression is detected by an anti-FLAG antibody and represented by a first binding curve; the negative control, an irrelevant cDNA, is represented by a second binding curve.

Evaluation of Sera Titer in Immune Response to Modified Multispanning Membrane Polypeptide Using FACS Analysis.

The first binding curve represents sera from mice immunized with modified multispanning membrane protein cDNA or purified protein binding to modified multispanning membrane protein expressing cells; a third curve represents the same sera sample binding to the corresponding wild-type membrane receptor expressing cell; a fourth curve represents cells transfected with an irrelevant cDNA.

A significant immune response in the immunized cohorts is characterized by mice polyclonal sera binding similarly to wild-type and modified multispanning membrane proteins.

Mice Immunized with Corresponding WT Receptor Using FACS Analysis.

The first binding curve represents sera from mice immunized with WT cDNA binding to modified multispanning membrane protein expressing cells; the third binding curve represents the same sera sample binding to wild-type modified multispanning membrane protein expressing cell; the fourth binding curve represents cells transfected with an irrelevant cDNA.

A significant immune response in the immunized cohorts is characterized by mice or rat polyclonal sera binding similarly to wild-type and modified multispanning membrane protein receptor.

ELISA Analysis.

Sera samples are analyzed for binding to solubilized membrane preparations of the relevant modified multispanning membrane protein immobilized to nickel chelate plate surfaces. Detection is accomplished by using anti-mouse HRP conjugate with TMB substrate and a positive control is provided by an anti-membrane protein polyclonal and using anti-guinea pig or other species HRP conjugate.

The ELISA data reflects the FACS analysis previously, e.g., that the modified multispanning membrane protein-based DNA immunization gives a similar antibody response to the WT DNA immunization, where an increasing sera titer is detected throughout the boosting period as shown by comparing pre-bleeds to interim bleeds (IB), for example: (IB1), (I132) and the final bleed. Sera samples are evaluated at different dilutions (1:50, 1:100, 1:500, 1:1000, and 1:5000).

Example 15—Functional Data to Show Use of Modified Multispanning Membrane Proteins as Vaccine Modified Multispanning Membrane Proteins as Vaccines Elicits Polyclonal Antibodies Impacting or Testing Modified Multispanning Membrane Protein Functional Activity.

The use of modified multispanning membrane protein or its encoding genetic material as an effective vaccine is demonstrated by the functional activity generated in the host's immune response, i.e., polyclonal antibodies. Different animal species are immunized primarily via Gene Gun vaccination/immunization using the modified multispanning membrane protein-encoding gene.

One read-out that is employed to assess the functional activity of the resulting sera is the impact on cAMP signaling.

The CRE-luc reporter assay is employed where the CRE response from activation of AC-cAMP-PKA pathway is the readout.

Subsequent analysis reveals that the polyclonal sera demonstrated both agonistic synergy with the correspondent agonist compound as well as agonist activity alone when the assay is conducted on WT transfected HEK293 or other cell lines. This activity is detected early on in the immunization protocol as demonstrated by the data generated from the rabbit analysis and compared to pre-immune sera. No activity is detected in any of the pre-immune sera samples. Target specificity is shown using HEK293 or other cell lines untransfected or transfected with DNA encoding for irrelevant multispanning membrane receptors.

Example 16—Enhancing the Immune Response to Modified Multispanning Membrane Proteins with Adjuvant Enhancing the Immune Response with GM-CSF.

GM-CSF or other cytokine-based molecular adjuvants (e.g., IL-4, IL-10, IL-17, IFN-γ, IFN-β etc.) are co-administered with the modified multispanning membrane protein encoding DNA, i.e., a genetic adjuvant, in order to enhance the immune response. This can be species-specific and has been demonstrated to increases mucosal and systemic immunogenicity of an H1N1 influenza DNA vaccine administered into the epidermis of Non-Human Primates. Other methods of enhancing the immune response used are, for example, tetanus and diphtheria toxoids as adjuvants, the use of Th epitopes incorporated as part of the expression construct, as has been shown for the PADRE Th epitope and the ovalbumin Th epitope in rodents. Other CD4+ epitopes have been identified from patient or immunized populations and implemented in HIV and malarial vaccine development, or even more recently developed adjuvants, such as, monophosphoryl lipid A. The strategy used for implementation of the adjuvant either takes the form of genetic components or formulations of compounds that are compatible with multispanning membrane protein integrity.

Enhancing the Immune Response Using E. coli GroEL.

The adjuvant activity of GroEL presumably involves inflammatory cytokine mediators via Toll-like receptor 4 in addition to a possible standard immune carrier effect. DNA immunization using GroEL is used as a method for producing antibodies for functional analysis or to induce antibodies to modified multispanning membrane proteins.

Modified multispanning membrane protein fused to E. coli GroEL or GroEL fragments or co-injected with a DNA sequence encoding for GroEL or GroEL fragments DNA immunization of mice or rats with a plasmid encoding for a modified multispanning membrane protein fused to Escherichia coli (E. coli) GroEL at its C-terminus is tested for the induction of specific antibody responses to WT and modified multispanning membrane protein. Co-injection of plasmids expressing the same combinations of modified multispanning membrane protein and GroEL or GroEL fragments encoding genes are also tested.

Modified Multispanning Membrane Protein Fused to Hsp70 or Fc Fragments or Co-Injected with a DNA Sequence Encoding for Hsp70 or Fc Fragments.

Modified multispanning membrane protein is fused to an Hsp70 or Fc fragment or co-injected with a DNA sequence encoding for Hsp70 or Fc fragments to enhance uptake by dendritic cells. The interaction of Fc with its FcgRs and/or Hsp proteins with CD91 activates dendritic cells by upregulating surface molecules and cytokines involved in antigen presentation. Moreover, the utilization of dendritic cell surface receptor pathways may also represent a privileged antigen internalization route for efficient MHC class I-restricted antigen presentation by dendritic cells (in addition to MHC class II) via the well-characterized mechanism of cross presentation.

Modified Multispanning Membrane Proteins Fused to sFlt-1 or Co-Injected with a DNA Sequence Encoding for sFlt-1.

Modified multispanning membrane proteins are also fused to sFlt-1 in immunotherapy/anti-antiangiogenic combination therapy. In contrast to the application of immunotherapy alone or antiangiogenic therapy alone, which may delay tumor growth, the combination of the two therapies has the opportunity to provide complete inhibition of tumor growth. The use of tumor targeting with immunotherapy in simultaneous combination with antiangiogenic therapy provides a more efficient strategy for the treatment of solid tumors.

Modified Multispanning Membrane Protein Fused to Active TLR Agonists Such Flagellin, a TLR5 Agonist or Co-Injected with a DNA Sequence Encoding for Flagellin or TLR5.

Phase 1 flagellin from *Salmonella* (called FliC) is a monomeric subunit protein, which polymerizes to form bacterial flagella. It has been extensively studied, and the regions and residues of flagellin that are required for TLR5 interaction have been defined. It has been demonstrated that it can potentiate immune responses to infectious disease using DNA-encoded Ags influencing a cascade of events inducing a Th1-like responses, although, in certain situations, the induction of Th2-like responses have also been observed. These observations indicate that FliC induces inflammatory immune response analog to TLR activation.

Modified Multispanning Membrane Protein Fused to Calreticulin (CRT) or Co-Injected with a DNA Sequence Encoding for CRT Strategies to compensate for the weak immune response generated by DCs transfected with DNA encoding the wild-type Ag: Some of these strategies include fusion of the TAA antigen to calreticulin (CRT), or to the sorting signal of the lysosome-associated membrane protein 1 (LAMP-1).

Example 17—Immunization with Modified Multispanning Membrane Protein

Testing Adjuvant/Modified Multispanning Membrane Protein Formulation Effect on Modified Multispanning Membrane Protein Stability Using Ligand Binding Assay.

The isolated modified multispanning membrane protein is combined with a number of different adjuvants and investigated for their stability at 37° C. over the course of two hours in a ligand binding assay. The adjuvants that are evaluated include, monophosphoryl lipid A (MPL), MM (marketed for generating mouse monoclonals Gerbu) and Pharma (Gerbu), TiterMax® Classic Adjuvant (TiterMax USA/Sigma-Aldrich), AdjuPrime™ Immune Modulator (Pierce). All adjuvants are tested in combination with the multispanning membrane polypeptide and show various degree of stability after 2 hours at 37° C. incubation in a ligand binding assay as compared with the control unformulated sample. The ligand binding assay testing conditions are designed to show relative compatibility of the tested immune adjuvant with purified multispanning membrane protein immunogen at body temperature.

Testing Adjuvant/Modified Multispanning Membrane Protein Formulation Effect on Induced Immune Response Using FACS and ELISA.

Modified multispanning membrane protein is formulated with a number of adjuvants using a 1:1 ratio. Balb-c mice and Wistar rats are immunized with the resulting different antigen/adjuvant formulations by intraperitoneal injection where the immunization protocol used protein priming and boosting to interim bleed 1 (4×50 µg of modified multi spanning membrane protein), followed by a shorter boosting phase using protein to interim bleed 2 (2×50 µg multispanning membrane protein). Immune response under the different experimental conditions is evaluated testing various dilutions of sera from immunized animals by FACS and ELISA.

Functional Antibody Response to Modified Multispanning Membrane Protein is Also Generated in Rabbits.

Agonistic and antagonist antibodies are also generated in a third host species (New Zealand White rabbits) using protein immunization, genetic immunization and combinations of genetic and protein immunization strategies. The initial DNA or protein challenge (immune priming) plus standard DNA or protein boosting is followed by a short interim boosting period and a final protein boost. Sera from immunized animals are assessed for binding to purified WT and to modified multispanning membrane protein WT and to modified multispanning membrane protein by ELISA and cell surface binding to mammalian cells transiently or stably transfected with WT and modified multispanning membrane encoding gene using FACS. The elicited sera agonistic activity will be also tested as functional evaluation using cell-based reporter assays. A robust immune response is seen with functional activity being detected as early as the first interim bleeds.

In some instances, immunization using modified multispanning membrane protein is used to generate an antibody with an inherently long CDR-H3 region, such as for example, similar to a CDR-H3 region of a bovine antibody, a shark antibody, a camelid antibody, a human auto-antibody or a human anti-HIV antibody. In some cases, an antibody with an extended CDR-H3 region is used for targeting difficult-to-bind epitopes, such as GPCRs, ion channels, and other multispanning membrane protein. In some cases, an antibody with an extended CDR-H3 region further undergoes a humanization process to generate a humanized antibody that target a modified multispanning membrane protein described herein.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods within the scope of these claims and their equivalents be covered thereby.

What is claimed is:

1. A modified multispanning membrane polypeptide of Formula (I):

SP2$_x$-L2$_m$-MSMP$_y$-L1$_n$-SP1$_z$     Formula I wherein:
- MSMP is a multispanning membrane polypeptide comprising at least one modification;
- SP1 is a first selection polypeptide linked to the C-terminus of MSMP, wherein SP1 confers resistance against a first selection agent;
- SP2 is a second selection polypeptide linked to the N-terminus of MSMP, wherein SP2 confers resistance against a second selection agent;
- L1 is a first linker;
- L2 is a second linker;
- x is independently 0-3;
- y is independently 1-5;
- z is independently 1-3; and
- m and n are each independently 0-60 amino acid residues.

2. The modified multispanning membrane polypeptide of claim 1, wherein the modified multispanning membrane polypeptide comprises a plasma membrane protein, a nuclear membrane protein, a peripheral membrane protein, an intracellular-membrane protein, a transporter, a channel protein, an adhesin, a translocase, or a receptor.

3. The modified multispanning membrane polypeptide of claim 1, wherein the modified multispanning membrane polypeptide is a modified ion channel protein.

4. The modified multispanning membrane polypeptide of claim 3, wherein the modified ion channel protein is a modified TRPV3, KCa3.1, or TRPC6.

5. The modified multispanning membrane polypeptide of claim 1, wherein the modified multispanning membrane polypeptide is a modified G protein coupled receptor (GPCR).

6. The modified multispanning membrane polypeptide of claim 5, wherein the modified GPCR is a modified CCR7, CCR10, GPR55, NTR1, EP2, or EP4 receptor.

7. The modified multispanning membrane polypeptide of claim 5, wherein the modified GPCR comprises about 1, 2, 3, 4, 5, 6, 7, 8, 9, 10, 15, 20, 25, 30, 35, 40, 45, 50, or more modified amino acid residues.

8. The modified multispanning membrane polypeptide of claim 5, wherein the modified GPCR comprises about 0.5%, 1%, 2%, 3%, 4%, 5%, 6%, 7%, 8%, 9%, 10%, 11%, 12%, 13%, 14%, 15%, 20%, 25%, 30%, or more modifications.

9. The modified multispanning membrane polypeptide of claim 1, wherein the at least one modification is generated through a random mutagenesis method.

10. The modified multispanning membrane polypeptide of claim 1, wherein SP1, when expressed in a host cell, is located in an intracellular portion of the host cell.

11. The modified multispanning membrane polypeptide of claim 1, wherein SP2, when expressed in a host cell, is located in an extracellular portion of the host cell.

12. The modified multispanning membrane polypeptide of claim 1, wherein the first selection polypeptide and the second selection polypeptide are each independently encoded by an antibiotic resistance gene, an auxotrophic gene, or a transcriptional activator or repressor.

13. The modified multispanning membrane polypeptide of claim 1, wherein the first selection polypeptide and the second selection polypeptide are each independently a polypeptide encoded by ampicillin resistance gene, carbenicillin resistance gene, gentamicin resistance gene, chloramphenicol resistance gene, neomycin resistance gene, kanamycin resistance gene, erythromycin resistance gene, tetracycline resistance gene, streptomycin resistance gene, pyrE gene, pyrF gene, HIS3 gene, URA3 gene, LYS2 gene, ADE1-2 gene, beta-galactosidase gene, or alkaline phosphatase gene.

14. The modified multispanning membrane polypeptide of claim 1, wherein $SP1_z$ is $SP1_{2-3}$ and each of the SP1 is different from the other.

15. The modified multispanning membrane polypeptide of claim 1, wherein $SP2_x$ is $SP2_{2-3}$ and each of the SP2 is different from the other.

16. The modified multispanning membrane polypeptide of claim 1, wherein the first selection agent and the second selection agent each independently comprises an antibiotic, a toxic metabolite, elevated temperature, reduced temperature, a lack of nutrient, or a lack of co-factor.

17. The modified multispanning membrane polypeptide of claim 1, wherein the modified multispanning membrane polypeptide further comprises a modified receptor polypeptide of Formula (II):

$$SP2_x\text{-}L2_m\text{-}RP_y\text{-}L1_n\text{-}SP1_z \qquad \text{Formula II}$$

wherein:
RP is a receptor polypeptide selected from an ion channel polypeptide or a GPCR, wherein RP comprises at least one modification;

SP1 is a first selection polypeptide linked to the C-terminus of RP, wherein SP1 confers resistance against a first selection agent;

SP2 is a second selection polypeptide linked to the N-terminus of RP, wherein SP2 confers resistance against a second selection agent;

L1 is a first linker;
L2 is a second linker;
x is independently 0-3;
y is independently 1-5;
z is independently 1-3; and
m and n are each independently 0-60 amino acid residues.

18. The modified multispanning membrane polypeptide of claim 1, wherein the modified multispanning membrane polypeptide further comprises a modified receptor polypeptide of Formula (III):

$$SP2_x\text{-}L2_m\text{-}GPCR_y\text{-}L1_n\text{-}SP1_z \qquad \text{Formula III}$$

wherein:
GPCR is a GPCR comprising at least one modification;
SP1 is a first selection polypeptide linked to the C-terminus of GPCR, wherein SP1, when expressed in a host cell, is located in the intracellular portion of the host cell and confers resistance against a first selection agent;

SP2 is a second selection polypeptide linked to the N-terminus of GPCR, wherein SP2, when expressed in a host cell, is located in the extracellular portion of the host cell and is resistant confers resistance against a second selection agent;

L1 is a first linker;
L2 is a second linker;
x is independently 0-3;
y is independently 1-5;
z is independently 1-3; and
m and n are each independently 0-60 amino acid residues.

19. The modified multispanning membrane polypeptide of claim 1, wherein the modified multispanning membrane polypeptide further comprises a modified receptor polypeptide of Formula (IV):

$$SP2_x\text{-}L2_m\text{-}ICP_y\text{-}L1_n\text{-}SP1_z \qquad \text{Formula IV}$$

wherein:
ICP is an ion channel polypeptide comprising at least one modification;
SP1 is a first selection polypeptide linked to the C-terminus of ICP, wherein SP1 confers resistance against a first selection agent;
SP2 is a second selection polypeptide linked to the N-terminus of ICP, wherein SP2 confers resistance against a second selection agent;
L1 is a first linker;
L2 is a second linker;
x is independently 0-3;
y is independently 1-5;
z is independently 1-3; and
m and n are each independently 0-60 amino acid residues.

20. A vector encoding a modified multispanning membrane polypeptide of claim 1.

21. A cell culture composition comprising a host cell expressing a modified multispanning membrane polypeptide of claim 1, and a cell culture media.

22. A method of screening a therapeutic agent against a modified multispanning membrane polypeptide of claim 1 to determine binding, comprising:
incubating the modified multispanning membrane polypeptide with the therapeutic agent; and detecting a binding between the multispanning membrane polypeptide and the therapeutic agent.

23. The method of claim 22, wherein the therapeutic agent is a small molecule or a polypeptide.

24. The method of claim 23, wherein the polypeptide is an antibody or its binding fragment thereof.

25. The method of claim 24, wherein the antibody or its binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, nanobody, single-domain antibody (sdAb), or camelid antibody or binding fragment thereof.

26. The method of claim 24, wherein the antibody or its binding fragment thereof is produced through a phage display or yeast display method.

27. The method of claim 22, wherein the incubating further comprises immobilizing the multispanning membrane polypeptide product on a nanoparticle prior to incubating with the therapeutic agent.

28. The method of claim 22, wherein the binding is detected by a flow cytometry method, by enzyme-linked immunosorbent assay (ELISA), a backscattering interferometry method, a fluorescent polarization method, a surface plasmon resonance (SPR) method, a plasmon-waveguide resonance method, a nuclear magnetic resonance (NMR) method, an isothermal titration calorimetry method, a thermal denaturation assay, a fluorescent ligand binding assay, or a radioligand binding assay.

29. The method of claim 27, wherein the flow cytometry method comprises magnetic-activated cell sorting (MACS) or fluorescence-activated cell sorting (FACS).

30. The method of claim 22, wherein the therapeutic agent further treats a disease or condition associated with a dysregulation and/or aberrant expression of a wild-type equivalent of the modified multispanning membrane polypeptide.

* * * * *

SEQUENCE LISTING

<160> NUMBER OF SEQ ID NOS: 2

<210> SEQ ID NO 1
<211> LENGTH: 321
<212> TYPE: PRT
<213> ORGANISM: Homo sapiens

<400> SEQUENCE: 1

Met Ser Gln Gln Asn Thr Ser Gly Asp Cys Leu Phe Asp Gly Val Asn
1               5                   10                  15

Glu Leu Met Lys Thr Leu Gln Phe Ala Val His Ile Pro Thr Phe Val
            20                  25                  30

Leu Gly Leu Leu Leu Asn Leu Leu Ala Ile His Gly Phe Ser Thr Phe
        35                  40                  45

Leu Lys Asn Arg Trp Pro Asp Tyr Ala Ala Thr Ser Ile Tyr Met Ile
    50                  55                  60

Asn Leu Ala Val Phe Asp Leu Leu Val Leu Ser Leu Pro Phe Lys
65                  70                  75                  80

Met Val Leu Ser Gln Val Gln Ser Pro Phe Pro Ser Leu Cys Thr Leu
                85                  90                  95

Val Glu Cys Leu Tyr Phe Val Ser Met Tyr Gly Ser Val Phe Thr Ile
            100                 105                 110

Cys Phe Ile Ser Met Asp Arg Phe Leu Ala Ile Arg Tyr Pro Leu Leu
        115                 120                 125

Val Ser His Leu Arg Ser Pro Arg Lys Ile Phe Gly Ile Cys Cys Thr
    130                 135                 140

Ile Trp Val Leu Val Trp Thr Gly Ser Ile Pro Ile Tyr Ser Phe His
145                 150                 155                 160

Gly Lys Val Glu Lys Tyr Met Cys Phe His Asn Met Ser Asp Asp Thr
                165                 170                 175

Trp Ser Ala Lys Val Phe Phe Pro Leu Glu Val Phe Gly Phe Leu Leu
            180                 185                 190

Pro Met Gly Ile Met Gly Phe Cys Cys Ser Arg Ser Ile His Ile Leu
        195                 200                 205

Leu Gly Arg Arg Asp His Thr Gln Asp Trp Val Gln Gln Lys Ala Cys
    210                 215                 220

Ile Tyr Ser Ile Ala Ala Ser Leu Ala Val Phe Val Val Ser Phe Leu
225                 230                 235                 240

Pro Val His Leu Gly Phe Phe Leu Gln Phe Leu Val Arg Asn Ser Phe
                245                 250                 255

Ile Val Glu Cys Arg Ala Lys Gln Ser Ile Ser Phe Phe Leu Gln Leu
            260                 265                 270

Ser Met Cys Phe Ser Asn Val Asn Cys Cys Leu Asp Val Phe Cys Tyr
        275                 280                 285

Tyr Phe Val Ile Lys Glu Phe Arg Met Asn Ile Arg Ala His Arg Pro
    290                 295                 300

Ser Arg Val Gln Leu Val Leu Gln Asp Thr Thr Ile Ser Arg Gly Ala
305                 310                 315                 320

Gly

<210> SEQ ID NO 2
<211> LENGTH: 321
<212> TYPE: PRT
<213> ORGANISM: Homo sapiens

<400> SEQUENCE: 2

```
Met Ser Gln Gln Asn Thr Ser Gly Asn Cys Leu Phe Asp Gly Met Asn
1               5                   10                  15

Glu Leu Met Lys Thr Leu Gln Phe Ala Val His Ile Pro Thr Phe Val
                20                  25                  30

Leu Gly Leu Leu Leu Asn Leu Leu Ala Ile His Gly Phe Ser Thr Phe
            35                  40                  45

Leu Lys Asn Arg Trp Pro Asp Tyr Ala Ala Thr Ser Ile Tyr Met Ile
50                      55                  60

Asn Leu Ala Val Phe Asp Leu Leu Leu Val Leu Ser Leu Pro Phe Lys
65                  70                      75                  80

Ile Val Leu Ser Gln Val Gln Ser Pro Phe Pro Ser Leu Cys Thr Leu
                85                  90                  95

Val Glu Cys Leu Tyr Phe Val Ser Met Tyr Gly Ser Val Phe Thr Ile
            100                 105                 110

Cys Phe Ile Ser Met Asp Arg Phe Leu Ala Ile Arg Tyr Pro Leu Leu
        115                 120                 125

Val Ser His Leu Arg Ser Pro Arg Lys Ile Phe Gly Ile Cys Cys Thr
        130                 135                 140

Ile Trp Val Leu Val Trp Thr Gly Ser Ile Pro Ile Tyr Ser Phe His
145                 150                 155                 160

Gly Lys Val Glu Lys Tyr Met Cys Phe His Asn Met Ser Asp Asp Thr
                165                 170                 175

Trp Ser Ala Lys Val Phe Phe Pro Leu Glu Val Phe Gly Phe Leu Leu
            180                 185                 190

Pro Met Gly Ile Met Gly Phe Cys Cys Ser Arg Ser Ile His Ile Leu
        195                 200                 205

Leu Gly Arg Arg Asp His Thr Gln Asp Trp Val Gln Gln Lys Ala Cys
    210                 215                 220

Ile Tyr Ser Ile Ala Ala Ser Leu Ala Val Phe Val Val Ser Phe Leu
225                 230                 235                 240

Pro Val His Leu Gly Phe Phe Leu Gln Phe Leu Val Arg Asn Ser Phe
            245                 250                 255

Ile Val Glu Cys Arg Ala Lys Gln Ser Ile Ser Phe Phe Leu Gln Leu
        260                 265                 270

Ser Lys Cys Phe Ser Asn Val Asn Cys Cys Leu Asp Val Phe Cys Tyr
    275                 280                 285

Tyr Phe Val Ile Lys Glu Phe Arg Met Asn Ile Arg Ala His Arg Pro
    290                 295                 300

Ser Arg Val Gln Leu Val Leu Gln Asp Thr Thr Ile Ser Arg Gly Ala
305                 310                 315                 320

Gly
```